US012630635B2

(12) United States Patent
Kowanetz et al.

(10) Patent No.: US 12,630,635 B2
(45) Date of Patent: *May 19, 2026

(54) POLYNUCLEOTIDES ENCODING ANTI-PD-L1 ANTIBODIES

(71) Applicant: Ventana Medical Systems, Inc., Tucson, AZ (US)

(72) Inventors: Marcin Kowanetz, San Francisco, CA (US); Hartmut Koeppen, San Mateo, CA (US); Zachary Boyd, Oakland, CA (US); Zhiming Liao, Livermore, CA (US); Yifei Zhu, San Jose, CA (US); Bharathi Vennapusa, Tucson, AZ (US); Patrick C. Roche, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 770 days.

This patent is subject to a terminal disclaimer.

(21) Appl. No.: 18/057,465

(22) Filed: Nov. 21, 2022

(65) Prior Publication Data

US 2023/0159641 A1 May 25, 2023

Related U.S. Application Data

(63) Continuation of application No. 16/872,158, filed on May 11, 2020, now Pat. No. 11,530,269, which is a continuation of application No. 15/727,388, filed on Oct. 6, 2017, now Pat. No. 10,689,445, which is a continuation of application No. 14/726,329, filed on May 29, 2015, now abandoned.

(60) Provisional application No. 62/023,741, filed on Jul. 11, 2014.

(51) Int. Cl.

| | |
|---|---|
| *C07K 16/28* | (2006.01) |
| *A61K 39/395* | (2006.01) |
| *A61K 45/06* | (2006.01) |
| *C07K 14/705* | (2006.01) |
| *G01N 33/53* | (2006.01) |
| *G01N 33/575* | (2026.01) |
| *A61N 5/10* | (2006.01) |

(52) U.S. Cl.

CPC ...... *C07K 16/2827* (2013.01); *A61K 39/3955* (2013.01); *A61K 45/06* (2013.01); *C07K 14/70532* (2013.01); *G01N 33/53* (2013.01); *G01N 33/5758* (2026.01); *A61N 2005/1021* (2013.01); *C07K 2317/34* (2013.01); *C07K 2317/54* (2013.01); *C07K 2317/55* (2013.01); *C07K 2317/622* (2013.01); *C07K 2317/76* (2013.01); *C07K 2319/30* (2013.01); *G01N 2500/10* (2013.01); *G01N 2800/52* (2013.01)

(58) Field of Classification Search

CPC .................................................. C07K 16/2827
See application file for complete search history.

(56) References Cited

U.S. PATENT DOCUMENTS

| | | | |
|---|---|---|---|
| 5,922,855 | A | 7/1999 | Liskay et al. |
| 6,803,192 | B1 | 10/2004 | Chen |
| 7,635,757 | B2 | 12/2009 | Freeman et al. |
| 7,754,208 | B2 | 7/2010 | Ledbetter et al. |
| 7,892,540 | B2 | 2/2011 | Chen et al. |
| 7,895,540 | B2 | 2/2011 | Engin et al. |
| 8,217,149 | B2 | 7/2012 | Irving et al. |
| 8,552,154 | B2 | 10/2013 | Freeman et al. |
| 8,981,063 | B2 | 3/2015 | Chen |
| 10,689,445 | B2 | 6/2020 | Kowanetz et al. |
| 2002/0028487 | A1 | 3/2002 | La Thangue et al. |
| 2006/0083744 | A1 | 4/2006 | Chen et al. |
| 2008/0299555 | A1 | 12/2008 | Nitta et al. |
| 2009/0055944 | A1 | 2/2009 | Korman et al. |
| 2009/0215084 | A1 | 8/2009 | Kwon et al. |
| 2009/0317368 | A1 | 12/2009 | Chen |
| 2010/0015642 | A1 | 1/2010 | Kwon et al. |
| 2010/0203056 | A1 | 8/2010 | Irving et al. |
| 2011/0200620 | A1 | 8/2011 | Chen et al. |
| 2011/0318839 | A1 | 12/2011 | Shiku et al. |
| 2012/0039906 | A1 | 2/2012 | Olive |
| 2013/0034559 | A1 | 2/2013 | Queva et al. |
| 2013/0260379 | A1 | 10/2013 | Alexander et al. |
| 2013/0309250 | A1 | 11/2013 | Cogswell et al. |
| 2014/0341917 | A1 | 11/2014 | Nastri et al. |
| 2014/0356353 | A1 | 12/2014 | Queva et al. |
| 2014/0357509 | A1 | 12/2014 | Ma et al. |
| 2015/0045251 | A1 | 2/2015 | Wang et al. |
| 2015/0071910 | A1 | 3/2015 | Kowanetz et al. |

(Continued)

FOREIGN PATENT DOCUMENTS

| | | |
|---|---|---|
| AU | 2012211347 A1 | 8/2012 |
| CN | 101084438 A | 12/2007 |

(Continued)

OTHER PUBLICATIONS

"A Global Study to Assess the Effects of MEDI4736 Following Concurrent Chemoradiation in Patients With Stage III Unresectable Non-Small Cell Lung Cancer (PACIFIC)," U.S. National Institutes of Health, <https://www.clinicaltrials.gov/ct2/show/NCT02125461>, last updated Mar. 25, 2015, retrieved on May 21, 2015 (4 pages).
"A Global Study to Assess the Effects of MEDI4736 Following Concurrent Chemoradiation in Patients With Stage III Unresectable Non-Small Cell Lung Cancer (PACIFIC)," U.S. National Institutes of Health, <https://clinicaltrials.gov/ct2/show/record/NCT02125461?term=medi4736+nsclc>, last updated May 1, 2017, retrieved on May 3, 2017 (7 pages).
"A Global Study to Assess the Effects of MEDI4736 Following Concurrent Chemoradition in Patients With Stage III Unresectable Non-Small Cell Lung Cancer (PACIFIC)", <https://clinicaltrials.gov/ct2/show/NCT02125461?term=medi4736+nsclc&rank=3>, dated Feb. 13, 2017, retrieved Nov. 11, 2020 (11 pages).

(Continued)

*Primary Examiner* — Elly-Gerald Stoica

(74) *Attorney, Agent, or Firm* — Clark & Elbing LLP; Thomas J. Takara

(57) ABSTRACT

The invention provides programmed death-ligand 1 (PD-L1) antibodies and methods of using the same.

21 Claims, 20 Drawing Sheets
(19 of 20 Drawing Sheet(s) Filed in Color)

Specification includes a Sequence Listing.

(56) References Cited

U.S. PATENT DOCUMENTS

| | | | |
|---|---|---|---|
| 2015/0148585 | A1 | 5/2015 | Das et al. |
| 2015/0309035 | A1 | 10/2015 | Tacha |
| 2015/0346208 | A1 | 12/2015 | Couto et al. |
| 2015/0346210 | A1 | 12/2015 | Nitta et al. |
| 2016/0009805 | A1 | 1/2016 | Kowanetz et al. |
| 2016/0222118 | A1 | 8/2016 | Chen et al. |
| 2016/0272712 | A1 | 9/2016 | Freeman et al. |
| 2016/0333085 | A1 | 11/2016 | Tacha et al. |
| 2016/0333414 | A1 | 11/2016 | Belousov et al. |
| 2016/0370370 | A1 | 12/2016 | Qi et al. |
| 2017/0023579 | A1 | 1/2017 | Nitta et al. |
| 2017/0052188 | A1 | 2/2017 | Kowanetz et al. |
| 2017/0082627 | A1 | 3/2017 | Dennis et al. |
| 2017/0101672 | A1 | 4/2017 | Luo et al. |
| 2017/0212122 | A1 | 7/2017 | Alexander et al. |
| 2018/0031567 | A1 | 2/2018 | Dennis et al. |
| 2018/0274038 | A1 | 9/2018 | Belousov et al. |
| 2018/0372747 | A1 | 12/2018 | Birch |

FOREIGN PATENT DOCUMENTS

| | | | |
|---|---|---|---|
| CN | 101104640 | A | 1/2008 |
| CN | 101248089 | A | 8/2008 |
| CN | 101355965 | A | 1/2009 |
| CN | 101622540 | A | 1/2010 |
| CN | 102250911 | A | 11/2011 |
| CN | 102428179 | A | 4/2012 |
| CN | 102740887 | A | 10/2012 |
| CN | 104470949 | A | 3/2015 |
| EP | 2420839 | A2 | 2/2012 |
| EP | 2926142 | B1 | 7/2018 |
| JP | 2006-340714 | A | 12/2006 |
| JP | 2008-544755 | A | 12/2008 |
| JP | 2012-503984 | A | 2/2012 |
| JP | 2017-514966 | A | 6/2017 |
| JP | 2017-514967 | A | 6/2017 |
| RU | 2315312 | C2 | 1/2008 |
| RU | 2395090 | C2 | 7/2010 |
| WO | WO-01/039722 | A2 | 6/2001 |
| WO | WO-2004/013632 | A1 | 2/2004 |
| WO | WO-2006/042237 | A2 | 4/2006 |
| WO | WO-2006/121168 | A1 | 11/2006 |
| WO | WO-2006/133396 | A2 | 12/2006 |
| WO | WO-2007/005874 | A2 | 1/2007 |
| WO | WO-2007/047955 | A2 | 4/2007 |
| WO | WO-2007/082154 | A2 | 7/2007 |
| WO | WO-2008/104953 | A2 | 9/2008 |
| WO | WO-2010/036959 | A2 | 4/2010 |
| WO | WO-2010/077634 | A1 | 7/2010 |
| WO | WO-2010/101249 | A1 | 9/2010 |
| WO | WO-2011/041613 | A2 | 4/2011 |
| WO | WO-2011/041613 | A3 | 4/2011 |
| WO | WO-2011/066389 | A1 | 6/2011 |
| WO | WO-2012/003476 | A2 | 1/2012 |
| WO | WO-2012/037378 | A2 | 3/2012 |
| WO | WO-2012/145493 | A2 | 10/2012 |
| WO | WO-2013/079174 | A1 | 6/2013 |
| WO | WO-2013/148498 | A1 | 10/2013 |
| WO | WO-2013/172926 | A1 | 11/2013 |
| WO | WO-2013/173223 | A1 | 11/2013 |
| WO | WO-2013/173233 | A1 | 11/2013 |
| WO | WO-2014/022758 | A1 | 2/2014 |
| WO | WO-2013/019906 | A9 | 3/2014 |
| WO | WO-2014/100079 | A1 | 6/2014 |
| WO | WO-2014/165082 | A2 | 10/2014 |
| WO | WO-2014/165422 | A1 | 10/2014 |
| WO | WO-2014/194293 | A1 | 12/2014 |
| WO | WO-2015/013388 | A2 | 1/2015 |
| WO | WO-2015/033172 | A1 | 3/2015 |
| WO | WO-2015/033173 | A1 | 3/2015 |
| WO | WO-2015/036499 | A1 | 3/2015 |
| WO | WO-2015/038538 | A1 | 3/2015 |
| WO | WO-2015/061668 | A1 | 4/2015 |
| WO | WO-2015/088930 | A1 | 6/2015 |
| WO | WO-2015/124703 | A1 | 8/2015 |
| WO | WO-2015/171588 | A1 | 11/2015 |
| WO | WO-2015/172284 | A1 | 11/2015 |
| WO | WO-2015/181342 | A1 | 12/2015 |
| WO | WO-2015/181343 | A2 | 12/2015 |
| WO | WO-2016/007235 | A1 | 1/2016 |
| WO | WO-2017/196867 | A1 | 11/2017 |

OTHER PUBLICATIONS

"A Study of Atezolizumab (an Engineered Anti-Programmed Death-Ligand 1 [PDL1] Antibody) to Evaluate Safety, Tolerability and Pharmacokinetics in Participants With Locally Advanced or Metastatic Solid Tumors," retrieved on Jan. 8, 2018, from <https://clinicaltrials.gov/ct2/show/NCT01375842> (12 pages).

"About HCDM," Human Cell Differentiation Molecules, <http://www.hcdm.org/index.php/about-hcdm>, retrieved Nov. 16, 2020 (5 pages).

"Assessment Run 36 2012, Cytokeratin, pan- (CK-PAN)," NordiQC, <https://www.nordiqc.org/downloads/assessments/36_85.pdf> last accessed Nov. 16, 2020, (6 pages).

"Breast Cancer," Wikipedia, <https://en.wikipedia.org/w/index.php?title=Brea%20st%20cancer&oldid=525497239>, retrieved on Jul. 23, 2019 (19 pages).

"Cancer Immunology: Pivotal Cancer Immunology Targets", <http://www.cellsignal.com/contents/science-cancer-research/pivotal-tumor-immunology-targets-pd-l1/pd-li-signaling>, published in 2017, retrieved Nov. 11, 2020 (5 pages).

"Catalogue d'anticorps 2011," AbD Serotec, <www.abdserotec.com/france> (2 pages).

"CD Marker Handbook," BD Biosciences, <https://www.bdbiosciences.com/documents/cd_marker_handbook.pdf>, last accessed Nov. 16, 2020 (56 pages).

"CD274 CD274 molecule [*Homo sapiens* (human)]," NCBI, <https://www.ncbi.nlm.nih.gov/gene/29126>, published 2015, retrieved Nov. 25, 2020 (10 pages).

"Estrogen Receptor," Wikipedia, <https://en.wikipedia.org/w/index.php?title=Estrogen_receptor&oldid=517956676>, retrieved Jul. 23, 2019 (7 pages).

"HER2/neu," Wikipedia, <https://en.wikipedia.org/w/index.php?title=HER2/neu&oldid=519951136>, retrieved on Jul. 23, 2019 (8 pages).

"History of Changes for Study: NCT01772004", submitted Jan. 16, 2013 (v1), <https://www.clinicaltrials.gov/ct2/history/NCT01772004?V_1=View#StudyPageTop>, retrieved Aug. 12, 2020 (5 pages).

*Immunohistochemical Staining Methods: IHC Guidebook, Sixth Edition*. Dako Denmark A/S, (2013) (218 pages).

"Investigational Immunotherapy Anti-PDL1 (MPDL3280A) Shrank Tumors in 43 Percent of People With a Specific Type of Metastatic Bladder Cancer in a Genentech Study", Roche, <www.gene.com/media/press-releases/14566/2014-05-31/investigational-immunotherapy-anti-pdl1>, published May 31, 2014, retrieved Nov. 25, 2020 (5 pages).

"Merck Serono Initiates Phase II Study of Anti-PD-L1 Antibody MSB0010718C in Metastatic Merkel Cell Carcinoma", retrieved Nov. 25, 2020, published in 2017 at <http://www.fiercebiotech.com/press-releases/merck-serono-initiates-phase-ii-study-anti-pd-l1-antibody-msb0010718c-metas> (5 pages).

"Multiplex Tissue Biomarkers in Context," PerkinElmer, Inc. (2014) (2 pages).

"NCI Drug Dictionary", National Cancer Institute, 2015, at <http://www.cancer.gov/publications/dictionaries>, retrieved Nov. 25, 2020 (33 pages).

"NCI Drug Dictionary: pembrolizumab," National Cancer Institute, published 2017 at <http:www.cancer.gov/drugdictionary?cdrid=695789> retrieved Nov. 25, 2020 (1 page).

"OptiView Detection Chemistry," Ventana Medical Systems, Inc. (2011) (4 pages).

"Pan Cytokeratin (pan CK) Monoclonal Antibody (AE1+AE3), TrueMAB™," Thermofisher Scientific, <https://www.thermofisher.com/antibody/product/pan-Cytokeratin-pan-CK-Antibody-clone-AE1-AE3-Monoclonal/CF190321>, retrieved on May 28, 2021 (7 pages).

(56)　　　　　References Cited

OTHER PUBLICATIONS

"PD-L1 (E1L3N®) XP® Rabbit mAb #13684," Cell Signaling Technology, <http://www.cellsignal.com/products/primary-antibodies/13684id=proteomics&utm_source=SalesFlyer&utm_medium=offline&utm_campaign=NPI&utm_content=PDL 1>, retrieved on May 3, 2017 (12 pages).

"PD-L1," Wikipedia, <https://en.wikipedia.org/w/index.php?title=PD-L1&oldid=451891615>, retrieved on Jul. 23, 2019 (5 pages).

"Pivotal Cancer Immunology Targets: New Rabbit mAbs for B7-H3 and B7-H4," Cell Signaling Technology, <http://www.cellsignal.com/contents/science-cancer-research/pivotal-tumor-immunology-targets-pdl1/pd-li-signaling>, retrieved on Dec. 1, 2020, printed May 21, 2015 (5 pages).

"Programmed Cell Death Protein 1," Wikipedia, <https:en.wikipedia.org/w/index.php?title=Programmed_cell_death_protein_I&oldid=519305474>, retrieved Jul. 24, 2019 (6 pages).

"Q9NZQ7—PD1L1_HUMAN," UniProt, <http://www.uniprot.org/uniprot/Q9NZQ7>, retrieved on May 21, 2015 (9 pages).

"Ruo Discovery Universal Staining procedure for Discovery Ultra Research Instrument," Ventana Medical Systems, Inc. (2014) (3 pages).

"Spring Bioscience launches highly sensitive PD-L1 (SP142) antibody for immunotherapy research," Spring Bioscience, <https://www.prnewswire.com/news-releases/spring-bioscience-launches-highly-sensitive-pd-l1-sp142-antibody-for-immunotherapy-research-272563651.html>, dated Aug. 25, 2014, retrieved on Apr. 12, 2020 (4 pages).

"Targeted Therapy," Wikipedia, <https://en.wikipedia.org/w/index.php?title=Targeted_therapy&oldid=522675520>, retrieved Aug. 2, 2019 (4 pages).

"Trastuzumab," Wikipedia, <https://en.wikipedia.org/w/index.php?title=Trastuzumab&oldid=525138397>, retrieved Jul. 23, 2019 (9 pages).

"UniProtKB—Q9NZQ7 (PD1L1_HUMAN)," UniProt, <http://www.uniprot.org/uniprot/Q9NZQ7>, retrieved on Jul. 22, 2015 (6 pages).

"Ventana Medical Systems, Inc. and MedImmune collaborate to develop a custom PD-L1 Assay for immunotherapy clincial trials," Ventana Medical Systems, Inc., dated Jun. 4, 2014 (2 pages).

Afanasiev et al., "Merkel polyomavirus-specific T cells fluctuate with Merkel cell carcinoma burden and express therapeutically targetable PD-1 and Tim-3 exhaustion markers," Clin Cancer Res. 19(19):5351-5360 (2013) (11 pages).

Ali et al., "PD-L1 protein expression in breast cancer is rare, enriched in basal-like tumours and associated with infiltrating lymphocytes," Annals of Oncology. 26(7):1488-1493 (2015).

Almagro et al., "Humanization of antibodies," Front Biosci. 13:1619-33 (2008).

Altree-Tacha et al., "Multiplex Cocktails for Immunotherapy Targets: PD-L1 with Tumor Specific Transcription Factors," Biocare Medical. Presented at USCAP 2017, Poster #297 (2017) (4 pages).

Bendig, Mary M., "Humanization of Rodent Monoclonal Antibodies by CDR Grafting," Methods: A Companion to Methods in Enzymology. 8:83-93 (1995).

Berglund et al., "The Epitope space of the human proteome," Protein Science. 17(4):606-613 (2008).

Brahmer et al., "Safety and Activity of Anti-PD-L1 Antibody in Patients with Advanced Cancer," N Engl J Med. 366(26):2455-65 (2012).

Brodská et al., "Correlation of PD-L1 Surface Expression on Leukemia Cells with the Ratio of PD-L1 mRNA Variants and with Electrophoretic Mobility," Cancer Immunol Res. 4(10):815-9 (2016).

Brown et al., "Blockade of programmed death-1 ligands on dendritic cells enhances T cell activation and cytokine production," J Immunol. 170(3):1257-66 (2003).

Brown et al., "Tolerance of single, but not multiple, amino acid replacements in antibody $V_H$ CDR2: a means of minimizing B cell wastage from somatic hypermutation?" J Immunol. 156(9):3285-91 (1996).

Butte et al., "Programmed Death-1 Ligand 1 Interacts Specifically with the B7-1 Costimulatory Molecule to Inhibit T Cell Responses," Immunity. 27(1):111-122 (2007).

Calles et al., "Differential expression of LKB1, PD-L1, and PD-L2 in KRAS-mutant non-small cell lung cancer in never-smokers," J Clin Oncol. 32(15 suppl):8032 (Abstract) (2014).

Capelozzi et al., "Role of Immunohistochemistry in the diagnosis of lung cancer," J Bras Pneumol. 35(4):375-382 (2009).

Carter et al., "PD-1/PD-L inhibitory pathway affects both CD4 and CD8 T cells and is overcome by IL-2," Eur J Immunol. 32(3):634-643 (2002).

Chakravarti et al., "Predictive factors of activity of anti-programmed death-1/programmed death ligand-1 drugs: immunohistochemistry analysis," Trans Lung Cancer Res. 4(6):743-751 (2015).

Chen et al., "Molecular pathways: next-generation immunotherapy—inhibiting programmed death-ligand 1 and programmed death-1," Clin Cancer Res. 18(24):6580-7 (2012).

Chen et al., "PD-L1 expression is characteristic of a subset of aggressive B-cell lymphomas and virus-associated malignancies," Clin Cancer Res. 19(13):3462-73 (2013).

Cheong et al., "Unexpected Epithelial Membrane Antigen (EMA) and Cytokeratin Expression in a Case of Infantile Acute Monoblastic Leukaemia," Hematology. 1(3):223-5 (1996).

Choueiri et al., "Correlation of PD-L1 Tumor Expression and Treatment Outcomes in Patients with Renal Cell Carcinoma Receiving Sunitinib or Pazopanib: Results from COMPARZ, a Randomized Controlled Trial," Clin Cancer Res. 21(5):1071-7 (2015).

Colman, "Effects of amino acid sequence changes on antibody-antigen interactions," Research in Immunology. 145:33-36 (1994).

Corada et al., "Monoclonal antibodies directed to different regions of vascular endothelial cadherin extracellular domain affect adhesion and clustering of the protein and modulate endothelial permeability," Blood. 97(6):1679-84 (2001) (7 pages).

Cunha et al., "Infiltration of a mixture of different immune cells may be related to molecular profile of differentiated thyroid cancer," Endocr Relat Cancer. 19(3):L31-6 (2012).

Curiel et al., "Blockade of B7-H1 improves myeloid dendritic cell-mediated antitumor immunity," Nat Med. 9(5):562-7 (2003).

D'Angelo et al., "Prevalence of tumor infiltrating lymphocytes and PD-L1 expression in the soft tissue sarcoma microenvironment," available in PMC Jul. 11, 2017, published in final edited form as: Hum Pathol. 46(3):357-65 (2015) (19 pages).

D'Eliseo et al., "Granzyme B is expressed in urothelial carcinoma and promotes cancer cell invasion," Int J Cancer. 127(6):1283-94 (2010).

Daoud et al., "The value of triple antibody (34betaE12 + p63 + AMACR) cocktail stain in radical prostatectomy specimens with crushed surgical margins," J Clin Pathol. 65(5):437-40 (2012) (5 pages).

Day et al., "Covalently deposited dyes: a new chromogen paradigm that facilitates analysis of multiple biomarkers in situ," Lab Invest. 97(1):104-13 (2017).

De Genst et al., "Antibody repertoire development in camelids," Dev Comp Immunol. 30(1-2):187-98 (2006).

Dong et al., "Tumor-associated B7-H1 promotes T-cell apoptosis: a potential mechanism of immune evasion," Nat Med. 8(8): 793-800 (2002).

Esteva et al., "CD40 signaling predicts response to preoperative trastuzumab and concomitant paclitaxel followed by 5-fluorouracil, epirubicin, and cyclophosphamide in HER-2-overexpressing breast cancer," Breast Cancer Res. 9(6):R87 (2007) (9 pages).

Freeman et al., "Engagement of the PD-1 Immunoinhibitory Receptor by a Novel B7 Family Member Leads to Negative Regulation of Lymphocyte Activation," J of Exp Med. 192(7):1027-1034 (2000).

Gaiser et al., "Tyramide signal amplification: an enhanced method for immunohistochemistry on methyl-methacrylate-embedded bone marrow trephine sections," Acta Haematol. 117(2):122-7 (2007).

Geng et al., "B7-H1 up-regulated expression in human pancreatic carcinoma tissue associates with tumor progression," J Cancer Res Clin Oncol. 134(9):1021-7 (2008).

(56)         References Cited

OTHER PUBLICATIONS

Ghebeh et al., "FOXP3+ Tregs and B7-H1+/PD-1+ T lymphocytes co-infiltrate the tumor tissues of high-risk breast cancer patients: Implication for immunotherapy," BMC Cancer. 8:57 (2008) (12 pages).
Ghebeh et al., "The B7-H1 (PD-L1) lymphocyte-inhibitory molecule is expressed in breast cancer patients with infiltrating ductal carcinoma: correlation with important high-risk prognostic factors," Neoplasia. 8(3):190-8 (2006).
Ginter et al., "The Minimal Carcinoma Triple Stain Is Superior to Commercially Available Multiplex Immunohistochemical Stains," Am J Clin Pathol. 144(6):869-79 (2015).
Gustmann et al., "Cytokeratin expression and vimentin content in large cell anaplastic lymphomas and other non-Hodgkin's lymphomas," Am J Pathol. 138(6):1413-22 (1991).
Hamanishi et al., "Programmed cell death 1 ligand 1 and tumor-infiltrating CD8+ T lymphocytes are prognostic factors of human ovarian cancer," Proc Natl Acad Sci U S A. 104(9):3360-5 (2007).
Hamid et al., "Anti-programmed death-1 and anti-programmed death-ligand 1 antibodies in cancer therapy," Expert Opin Biol Ther. 13(6):847-61 (2013).
Hawes et al., "Immunohistochemistry," The Surgical Pathology Laboratory. 1:48-70 (2009).
Herawi et al., "Immunohistochemical Antibody Cocktail Staining (p63/HMWCK/AMACR) of Ductal Adenocarcinoma and Gleason Pattern 4 Cribriform and Noncribriform Acinar Adenocarcinomas of the Prostate," Am J Surg Pathol. 31(6):889-94 (2007) (7 pages).
Hirsch et al., "PD-L1 Immunohistochemistry Assays for Lung Cancer: Results from Phase 1 of the Blueprint PD-L1 Ihc Assay Comparison Project," J Thorac Oncol. 12(2):208-22 (2017).
Hoyt et al., "New method for spatial-phenotypical characterization of cancer-associated infiltrating and stromal lympocytes." Poster 2014, <https://www.perkinelmer.com/CMSResources/Images/44-157025PST_USCAP_2014_Hoyt_Feldman_New_Method_Spatial_Pheno_Characterization_Cancer_Infiltrating_Stromal_Lymphocytes.pdf>. Retrieved on Dec. 10, 2021 (2 pages).
Huang et al., "Detecting cell-in-cell structures in human tumor samples by E-cadherin/CD68/CD45 triple staining," Oncotarget. 6(24):20278-87 (2015).
Iwai et al., "Involvement of PD-L1 on tumor cells in the escape from host immune system and tumor immunotherapy by PD-L1 blockade," PNAS. 99(19):12293-7 (2002).
Iwai et al., "PD-1 blockade inhibits hematogenous spread of poorly immunogenic tumor cells by enhanced recruitment of effector T cells," Int Immunol. 17(2):133-44 (2004).
Kalra et al., "Multiplex Immunohistochemistry for Mapping the Tumor Microenvironment," *Signal Transduction Immunohistochemistry: Methods and Protocols, Methods in Molecular Biology*, vol. 1554. Springer Science+Business Media LLC, 237-51 (2017).
Konishi et al., "B7-H1 expression on non-small cell lung cancer cells and its relationship with tumor-infiltrating lymphocytes and their PD-1 expression," Clin Cancer Res. 10(15):5094-100 (2004) (8 pages).
Kreienberg et al., "Interdisciplinary GoR level III Guidelines for the Diagnosis, Therapy and Follow-up Care of Breast Cancer: Short version—AWMF Registry No. 032-045OL," Geburtshilfe Frauenheilkd. 73(6):556-583 (2013) (28 pages).
Kwak et al., "A convenient method for epitope competition analysis of two monoclonal antibodies for their antigen binding," J Immunol Methods. 191(1):49-54 (1996).
Latchman et al., "PD-L2 is a second ligand for PD-1 and inhibits T cell activation," Nature Immunology. 2(3):261-268 (2001).
Lee et al., "Immunofluorescent Triple-Staining Technique to Identify Sensory Nerve Endings in Human Thumb Ligaments," Cells Tissues Organs. 195(5):456-64 (2012).
Lehr et al., "Complete Chromogen Separation and Analysis in Double Immunohistochemical Stains Using Photoshop-based Image Analysis," J Histochem Cytochem. 47(1):119-25 (1999).

Levenson et al., "Immunohistochemistry and mass spectrometry for highly multiplexed cellular molecular imaging," Lab Invest. 95(4):397-405 (2015).
Lloyd et al., "Phenotyping immune cells in-situ. An investigation of the spatial heterogeneity of specific immune cell phenotypes in the tumour microenvironment," Perkin Elmer University of Manchester. (2014) (1 page).
Lyford-Pike et al., "Evidence for a Role of the PD-1:PD-L1 Pathway in Immune Resistance of HPV-Associated Head and Neck Squamous Cell Carcinoma," Cancer Res. 73(6):1733-41 (2013).
Mahoney et al., "Antibodies to the cytoplasmic domain of PD-L1 most clearly delineate cell membranes in immunohistochemical staining," available in PMC Dec. 1, 2016, published in final edited form as: Cancer Immunol Res. 3(12):1308-15 (2015).
Mansfield et al., "Favourable diffuse prognostic pattern of FOXP3+ and CD69+ T cells in follicular lymphoma demonstrated using automated imaging and analysis." Poster 2014, <https://www.perkinelmer.com/CMSResources/Images/44-157458PST_AACR2014_TSC_FOXP3_CD69_TcellsFol-licularLymphomaAutomatedImagingAnalysis_Mansfield%20Byers.pdf>. Retrieved on Dec. 10, 2021 (2 pages).
McLaughlin et al., "Domain-specific PD-L1 protein measurement in non-small cell lung cancer (NSCLC)," 2014 ASCO Annual Meeting. J Clin Oncol. 32(15 suppl): Abstract 8064 (2014) (2 pages).
McLaughlin et al., "Domain-specific PD-L1 protein measurement in non-small cell lung cancer (NSCLC)," Journal of Clinical Oncology. 32(15_suppl):8064, Abstract 8064 (2014) (Abstract only).
Melero et al., "Clinical Development of Immunostimulatory Monocolonal Antobodies and Opportunities for Combination," Clin Cancer Res. 19(5):997-1008 (2013).
Miller, Rodney T., "Cytokeratin AE1/AE3," ProPath. Nov. 2003, <https://propath.com/cytokeratin-ae1-ae3/>, accessed May 27, 2021 (3 pages).
Mitchell, "Combinations of anticancer drugs and immunotherapy," Cancer Immunol Immunother. 52(11):686-92 (2003).
Molina et al., "Trastuzumab (herceptin), a humanized anti-Her2 receptor monoclonal antibody, inhibits basal and activated Her2 ectodomain cleavage in breast cancer cells," Cancer Res. 61(12):4744-9 (2001).
Mu et al., "High expression of PD-L1 in lung cancer may contribute to poor prognosis and tumor cells immune escape through suppressing tumor infiltrating dendritic cells maturation," Med Oncol. 28(3):682-8 (2011).
Mullane et al., "PD-L1 expression in mononuclear cells and not in tumor cells, correlated with prognosis in metastatic urothelial carcinoma," <http://meetinglibrary.asco.org/print/1736722>, retrieved on Sep. 8, 2015 (2 pages).
Nelson et al., "Automated prognostic pattern detection shows favorable diffuse pattern of FOXP3+ Tregs in follicular lymphoma," Br J Cancer. 113(8):1197-205 (2015).
Ogata et al., "Differences in blast immunophenotypes among disease types in myelodysplastic syndromes: a multicenter validation study," Leuk Res. 36(10):1229-36 (2012).
Ohigashi et al., "Clinical Significance of Programmed Death-1 Ligand-1 and Programmed Death-1 Ligand-2 Expression in Human Esophageal Cancer," Clin Cancer Res. 11(8):2947-2953 (2005) (8 pages).
Padlan, "X-ray crystallography of antibodies," Adv Protein Chem. 49:57-133 (1996).
Park et al., "V-ets erythroblastosis virus E26 oncogene homolog (avian)/Trefoil factor 3/high-molecular-weight cytokeratin triple immunostain: a novel tissue-based biomarker in prostate cancer with potential clinical application," Hum Pathol. 44:2282-92 (2013).
Parra et al., "Comparison of Different Antibody Clones for Immunohistochemistry Detection of Programmed Cell Death Ligand 1 (PD-L1) on Non-Small Cell Lung Carcinoma," Appl Immunohistochem Mol Morphol. 26(2):83-93 (2018).
Paul, Chapter 9: Structure and Function of Immunoglobulins. Fundamental Immunology, Third Edition. Raven Press, 292-295 (1993) (6 pages).
Peng et al., "PD-1 blockade enhances T-cell migration to tumors by elevating IFN-gamma inducible chemokines," Cancer Res. 72(20):5209-18 (2012).

(56)　　　　　　References Cited

OTHER PUBLICATIONS

Powderly et al., "Biomarkers and associations with the clinical activity of PD-L1 blockade in a MPDL3280A study," <https://meetinglibrary.asco.org/record/83742/abstract>, retrieved May 2, 2018 (21 pages).

Ramos-Vara, "Technical Aspects of Immunohistochemistry," Vet Pathol. 42(4):405-26 (2005).

Rebelatto et al., "Development of a PD-L1 companion diagnostic assay for treatment with MEDI4736 in NSCLC and SCCHN patients," Journal of Clinical Oncology 33(15):1-3 (2015).

Ribas et al., "The Future of Cancer Therapy: Selecting Patients Likely to Respond to PD1/L1 Blockade," Clin Cancer Res. 20(19):4982-4 (2014).

Rosenblatt et al., "Targetting the PD-L1/PD-1 axis holds promise in the treatment of malignancy," Transl Cancer Res. 1(4):283-6 (2012).

Ross et al., "The Diagnostic Utility of the Minimal Carcinoma Triple Stain in Breast Carcinomas," Am J Clin Pathol. 139(1):62-70 (2013).

Rudikoff et al., "Single amino acid substitution altering antigen-binding specificity," Proc Natl Acad Sci U S A. 79(6):1979-83 (1982).

Sasaki et al., "PD-L1 gene expression in Japanese lung cancer patients," Biomed Rep. 1(1):93-96 (2013).

Shen et al., "Impaired ICOSL in human myeloid dendritic cells promotes Th2 responses in patients with allergic rhinitis and asthma," Clin Exp Allergy. 44(6):831-41 (2014).

Shklovskaya et al., "Spatial and Temporal Changes in PD-L1 Expression in Cancer: The Role of Genetic Drivers, Tumor Microenvironment and Resistance to Therapy," Int J Mol Sci. 21(7139):1-23 (2020).

Stack et al., "Multiplexed immunohistochemistry, imaging, and quantification: A review, with an assessment of Tyramide signal amplification, multispectral imaging and multiplex analysis," Methods. 70(1):46-58 (2014).

Stagg et al., "Anti-ErbB-2 mAb therapy requires type I and II interferons and synergizes with anti-PD-1 or anti-CD137 mAb therapy," Proc Natl Acad Sci USA. 108(17):7142-7 (2011).

Stagg et al., "Supporting Information," Proc Natl Acad Sci USA. doi: 10.1073/pnas.1016569108 (2011) (5 pages).

Sung et al., "Alpha-methylacyl-CoA racemase (P504S)/34betaE12/p63 triple cocktail stain in prostatic adenocarcinoma after hormonal therapy," Hum Pathol. 38(2):332-41 (2007).

Sznol et al., "Antagonist antibodies to PD-1 and B7-H1 (PD-L1) in the treatment of advanced human cancer," Clin Cancer Res. 19(5):1021-34 (2013).

Takada et al., "An Immunohistochemical Analysis of PD-L1 Protein Expression in Surgically Resected Small Cell Lung Cancer Using Different Antibodies and Criteria," Anticancer Res. 36(7):3409-12 (2016).

Taube et al., "Association of PD-1, PD-1 Ligands, and Other Features of the Tumor Immune Microenvironment with Response to Anti-PD-1 Therapy," Clin Cancer Res. 20(19):5064-74 (2014) (12 pages).

Taube et al., "Colocalization of inflammatory response with B7-h1 expression in human melanocytic lesions supports an adaptive resistance mechanism of immune escape," available in PMC Feb. 10, 2013, published in final edited form as: Sci Transl Med. 4(127):127ra37 (2012) (22 pages).

Topalian et al., "Safety, Activity, and Immune Correlates of Anti-PD-1 Antibody in Cancer," N Engl J Med. 366(26):2443-54 (2012).

Tumeh et al., "PD-1 blockade induces responses by inhibiting adaptive immune resistance," Nature. 515(7528):568-571 (2014).

Tzartos, "Epitope Mapping by Antibody Competition: Methodology and Evaluation of the Validity of the Technique." *Methods in Molecular Biology, vol. 66. Epitope Mapping Protocols.* Humana Press, Inc., 55-66 (1996).

Tóth et al., "Simultaneous Visualization of Multiple Antigens With Tyramide Signal Amplification Using Antibodies From the Same Species," J Histochem Cytochem. 55(6):545-54 (2007).

Untch et al., "Neoadjuvant treatment with trastuzumab in HER2-positive breast cancer: results from the GeparQuattro study," J Clin Oncol. 28(12):2024-31 (2010).

Van der Loos, "Multiple Immunoenzyme Staining: Methods and Visualizations for the Obersevation With Spectral Imaging," J Histochem Cytochem. 56(4):313-28 (2008).

Van der Loos, Chris M., "Chromogens in Multiple Immunohistochemical Staining Used for Visual Assessment and Spectral Imaging: The Colorful Future," The Journal of Histotechnology. 33(1):31-40 (2010).

Vanneman et al., "Combining immunotherapy and targeted therapies in cancer treatment," Nat Rev Cancer. 12(4):237-51 (2012).

Velcheti et al., "Programmed death ligand-1 expression in non-small cell lung cancer," Lab Invest. 94(1):107-16 (2014).

Warford et al., "Antigen retrieval, blocking, detection and visualisation systems in immunohistochemistry: a review and practical evaluation of tyramide and rolling circle amplification systems," Methods. 70(1):28-33 (2014).

Weber et al., "Safety, Efficacy, and Biomarkers of Nivolumab With Vaccine in Ipilimumab- Refractory or -Naive Melanoma," J Clin Oncol. 31(34):4311-4318 (2013) (10 pages).

Weber, "Immune checkpoint proteins: a new therapeutic paradigm for cancer—preclinical background: CTLA-4 and PD-1 blockade," Semin Oncol. 37(5):430-9 (2010).

Willis et al., "SOX10: A Useful Marker for Identifying Metastatic Melanoma in Sentinel Lymph Nodes," Appl Immunohistochem Mol Morphol. 23(2):109-12 (2015) (5 pages).

Xu et al., "Loss of Lkb1 and Pten leads to lung squamous cell carcinoma with elevated PD-L1 expression," Cancer Cell. 25(5):590-604 and supplemental information (2014) (39 pages).

Yan et al., "MYC Expression in Concert with BCL2 and BCL6 Expression Predicts Outcome in Chinese Patients with Diffuse Large B-Cell Lymphoma, Not Otherwise Specified," PLoS One. 9(8):e104068 (2014) (16 pages).

Yanagita et al., "Rapid Multiplex Immunohistochemistry Using the 4-antibody Cocktail YANA-4 in Differentiating Primary Adenocarcinoma From Squamous Cell Carcinoma of the Lung," Appl Immunohistochem Mol Morphol. 19(6):509-13 (2011) (6 pages).

Yunmei et al., "VSIG4 expression on macrophages facilitates lung cancer development," Laboratory Investigation 94(7):706-715 (2014).

Zhang et al., "Chemopreventive agents induce programmed death-1-ligand 1 (PD-L1) surface expression in breast cancer cells and promote PD-L1-mediated T cell apoptosis," Mol Immunol. 45(5):1470-6 (2008).

Zhang et al., "PD-1/PD-L1 interactions inhibit antitumor immune responses in a murine acute myeloid leukemia model," Blood. 114(8):1545-52 (2009).

Zhao et al., "Prognostic value of PD-L1 expression in tumor infiltrating immune cells in cancers: A meta-analysis," PLoS One. 12(4): e0176822 (2017) (17 pages).

Communication of a notice of opposition for European Patent Application No. 15727610.6, dated Oct. 14, 2019 (46 pages).

Communication pursuant to Article 94(3) for European Patent Application No. 14714119.6, dated Feb. 17, 2017 (7 pages).

English Translation of Second Office Action for Chinese Patent Application No. 201480027406.7, dated Mar. 13, 2017 (12 pages).

English Translation of Third Office Action for Chinese Patent Application No. 201480027406.7, dated Nov. 3, 2017 (9 pages).

Examination Report No. 2 for Australian Patent Application No. 2014235453, dated Sep. 8, 2017 (4 pages).

First Office Action for Chinese Patent Application No. 201480027406. 7, dated May 20, 2016 (19 pages).

International Preliminary Report on Patentability for International Patent Application No. PCT/US2014/024746, issued Sep. 15, 2015 (13 pages).

International Preliminary Report on Patentability for International Patent Application No. PCT/US2015/033395, issued Jan. 17, 2017 (8 pages).

International Preliminary Report on Patentability for PCT/EP2016/052107, issued on Aug. 8, 2017 (8 pages).

(56)                    References Cited

OTHER PUBLICATIONS

International Search Report and Written Opinion for International Patent Application No. PCT/US2015/033395, mailed Aug. 5, 2015 (15 pages).

International Search Report and Written Opinion for PCT/EP2016/052107, mailed on Apr. 5, 2016, (7 pages).

International Search Report for International Patent Application No. PCT/US2014/024746, mailed Sep. 29, 2014 (8 pages).

International Search Report for PCT/US2014/062149, issued Feb. 23, 2015, (3 pages).

Letter of Opponent dealing with Oral proceedings for European Patent Application No. 15727610.6, dated Dec. 15, 2020 (2 pages).

Notice of opposition to a European patent for European Patent Application No. 15727610.6, dated Oct. 9, 2019 (5 pages).

Notice of Reasons for Rejection for Japanese Patent Application No. 2016-501626, dated Oct. 4, 2016 (8 pages).

Notice of Reasons for Rejection for Japanese Patent Application No. 2016-501626, dated Sep. 12, 2017 (9 pages).

Notice of Reasons for Rejection for Japanese Patent Application No. 2017-501231, issued May 7, 2019 (13 pages).

Notification of Defects for Israeli Patent Application No. 250032, dated Nov. 27, 2019 (10 pages).

Office Action for Russian Patent Application No. 2017103495, dated Aug. 5, 2019 (5 pages).

Office Action for Russian Patent Application No. 2017103495, dated Jan. 14, 2019 (9 pages).

Office Action for U.S. Appl. No. 14/725,288, mailed Apr. 6, 2017 (32 pages).

Office Action for U.S. Appl. No. 14/850,462, mailed Jan. 4, 2018 (24 pages). .

Opponent Reply to Patentee Submission for European Patent Application No. 15727610.6, dated May 27, 2020 (10 pages).

Opposition Submission to European Patent No. 3149481, dated Oct. 9, 2019 (2 pages).

Priority document for International Patent Application No. PCT/US2014/062149, received Dec. 21, 2014: U.S. Appl. No. 61/895,543, filed Oct. 25, 2013 (98 pages).

Response to Communication of Notice of Opposition for European Patent Application No. 15727610.6, dated Mar. 2, 2020 (85 pages).

Response to the Summons to attend Oral Proceedings for European Patent Application No. 15727610.6, dated Dec. 11, 2020 (43 pages).

Search Report and Written Opinion for Brazilian Patent Application No. BR112017000497-6, dated Aug. 11, 2020 (4 pages).

Search Report for Chinese Patent Application No. 201480027406.7, dated May 11, 2016 (5 pages).

Search Report for Singaporean Patent Application No. 11201507333X, dated Jul. 8, 2016 (5 pages).

Statement of Facts and Arguments for European Patent Application No. 15727610.6, dated Oct. 9, 2019 (40 pages).

Submission in opposition proceedings for European Patent Application No. 15727610.6, dated Feb. 5, 2021 (8 pages).

Submission in opposition proceedings for European Patent No. 3149481, dated Mar. 2, 2020 (3 pages).

Submission in opposition proceedings made following summons to attend oral proceedings for European Patent No. 3149481, dated Feb. 5, 2021 (9 pages).

Substantive Examination for Malaysian Patent Application No. PI 2017000043, dated Feb. 18, 2020, (5 pages).

Summons to attend oral proceedings pursuant to Rule 115(1) EPC for European Patent Application No. 15727610.6, dated Jun. 10, 2020 (13 pages).

Written Opinion for Singaporean Patent Application No. 11201507333X, dated Sep. 6, 2016 (8 pages).

Written Opinion for Singaporean Patent Application No. 11201700207W, dated Nov. 6, 2017 (8 pages).

Written Opinion for Singaporean Patent Application No. 11201700207W, dated Sep. 3, 2019 (7 pages).

Broderick, "Avelumab Fails to Improve OS in Phase III Gastric Cancer Trial," Targeted Onc. (Nov. 2017) (3 pages).

Fehrenbacher et al., "Atezolizumab versus docetaxel for patients with previously treated non-small-cell lung cancer (POPLAR): a multicentre, open-label, phase 2 randomised controlled trial" Lancet. 387: 1837-46 (Mar. 2016).

Felip et al., "Adjuvant atezolizumab after adjuvant chemotherapy in resected stage IB-IIIA non-small-cell lung cancer (IMpower010): a randomised, multicentre, open-label, phase 3 trial," The Lancet. 398: 1344-1357 (Oct. 2021) (14 pages).

Genentech, "A Phase 1b Study of Atezolizumab in Combination with Vemurafenib or Vemurafenib Plus Cobimetinib in Participants with BRAFV600-Mutation Positive Metastatic Melanoma," <https://clinicaltrials.gov/study/NCT01656642?tab=history&a=3#version-content-panel>, dated Nov. 16, 2012 (15 pages).

Naidoo et al., "Toxicities of the anti-PD-1 and anti-PD-L1 immune checkpoint antibodies," Annals of Oncology. 26(12):2375-91 (Dec. 2015) (17 pages).

Ohaegbulam et al., "Human cancer immunotherapy with antibodies to the PD-1 and PD-L1 pathway," available in PMC Jan. 1, 2016, published in final edited form as: Trends Mol Med. 21(1): 24-33 (Jan. 2015) (23 pages).

Powderly et al., "Biomarkers and associations with the clinical activity of PD-L1 blockade in a MPDL3280A study," Journal of Clinical Oncology. 31(15_suppl):3001. Published online May 20, 2013 (2013) (3 pages).

Rittmeyer et al., "Atezolizumab versus docetaxel in patients with previously treated non-small-cell lung cancer (OAK): a phase 3, open-label, multicentre randomised controlled trial," Lancet. 389(10066):255-265 (Jan. 2017).

Spigel et al., "Clinical activity, safety, and biomarkers of MPDL3280A, an engineered PD-L1 antibody in patients with locally advanced or metastatic non-small cell lung cancer (NSCLC)," Journal of Clinical Oncology. 31(15_suppl):8008 (May 2013).

West et al., "Atezolizumab in combination with carboplatin plus nab-paclitaxel chemotherapy compared with chemotherapy alone as first-line treatment for metastatic non-squamous non-small-cell lung cancer (IMpower130): a multicentre, randomised, open-label, phase 3 trial," Lancet Oncol. 20(7):924-937 (Jul. 2019).

Zitvogel et al., "Targeting PD-1/PD-L1 interactions for cancer immunotherapy," Oncoimmunology 1(8):1223-1225 (Nov. 2012).

E1L3N

SP142

Figures 12A-12C
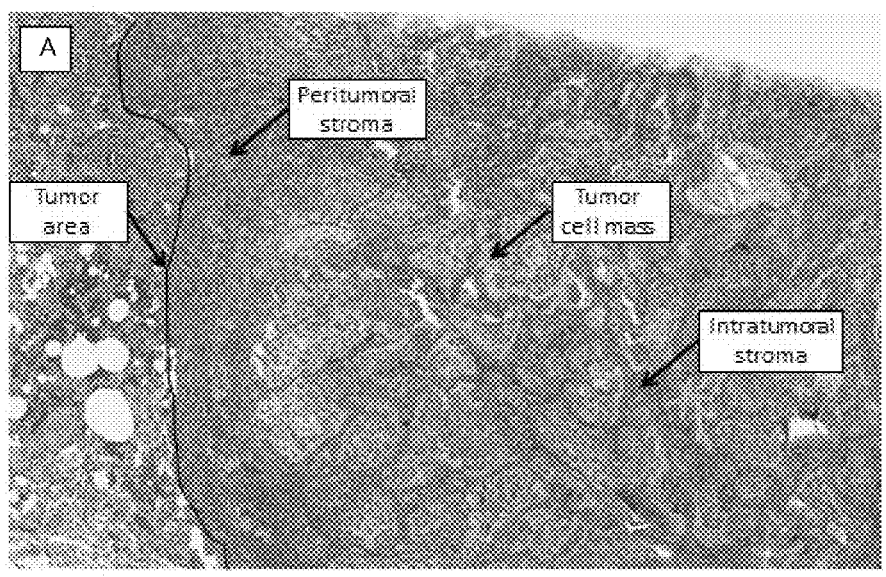
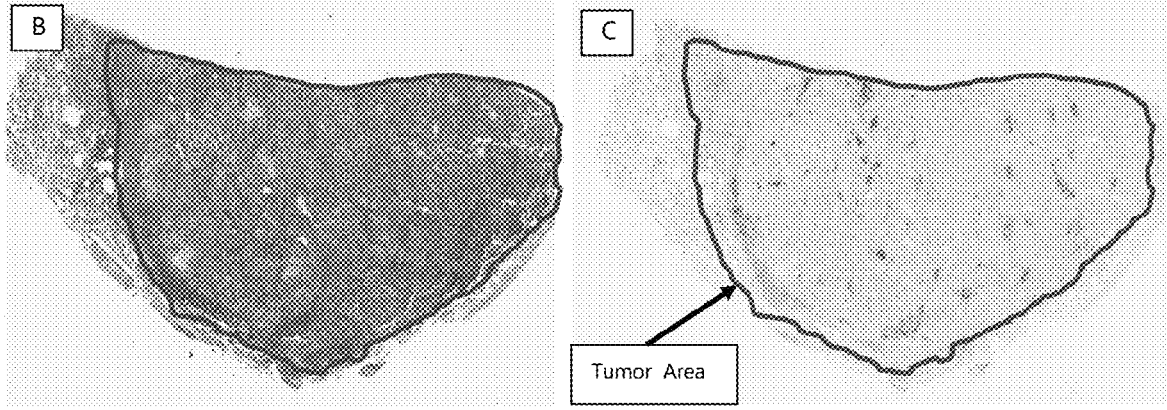

Figure 13

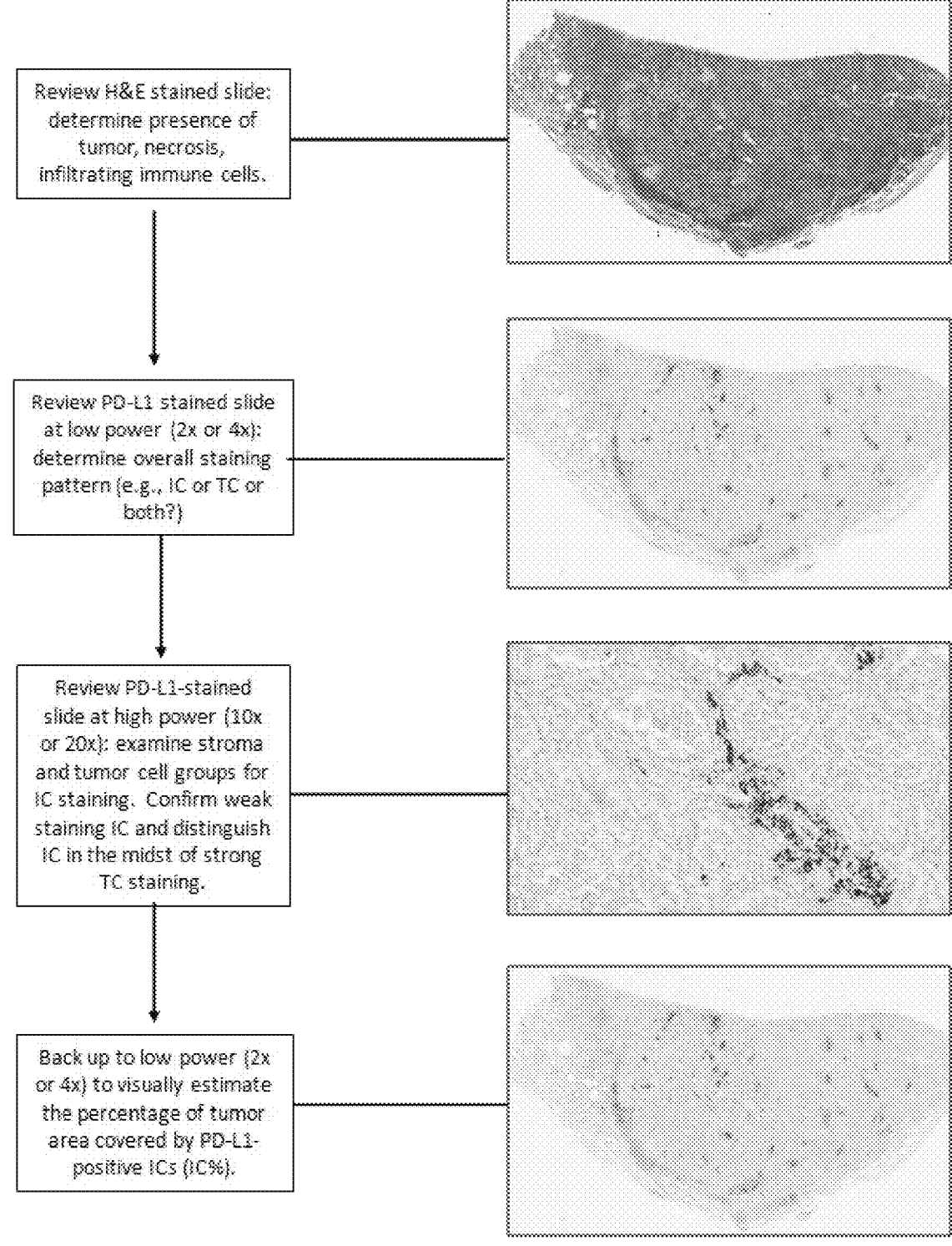

Review H&E stained slide: determine presence of tumor, necrosis, infiltrating immune cells.

Review PD-L1 stained slide at low power (2x or 4x): determine overall staining pattern (e.g., IC or TC or both?)

Review PD-L1-stained slide at high power (10x or 20x): examine stroma and tumor cell groups for IC staining. Confirm weak staining IC and distinguish IC in the midst of strong TC staining.

Back up to low power (2x or 4x) to visually estimate the percentage of tumor area covered by PD-L1-positive ICs (IC%).

A.

B.

TC <5%

TC ≥5-<50%

TC ≥50%

POLYNUCLEOTIDES ENCODING ANTI-PD-L1 ANTIBODIES

CROSS-REFERENCE TO RELATED APPLICATIONS

This application is a continuation of U.S. application Ser. No. 16/872,158, filed on May 11, 2020, which is a continuation of U.S. application Ser. No. 15/727,388, filed on Oct. 6, 2017, which is a continuation of U.S. application Ser. No. 14/726,329, filed on May 29, 2015, which claims the benefit of the filing date of U.S. Provisional Application No. 62/023,741, filed on Jul. 11, 2014, the disclosures of which are incorporated herein by reference in their entirety.

SEQUENCE LISTING

The instant application contains a Sequence Listing which has been submitted electronically in XML format and is hereby incorporated by reference in its entirety. Said XML copy, created on Nov. 10, 2022, is named 51264-002005_Sequence_Listing_11_10_22 and is 17,052 bytes in size.

FIELD OF THE INVENTION

The present invention relates to anti-programmed death-ligand 1 (PD-L1) antibodies and methods of using the same.

BACKGROUND

Programmed death-ligand 1 (PD-L1) is a protein that has been implicated in the suppression of immune system responses during chronic infections, pregnancy, tissue allografts, autoimmune diseases, and cancer. PD-L1 regulates the immune response by binding to an inhibitory receptor, known as programmed death 1 (PD-1), which is expressed on the surface of T-cells, B-cells, and monocytes. PD-L1 negatively regulates T-cell function also through interaction with another receptor, B7.1 (also known as B7-1 or CD80). Formation of the PD-L1/PD-1 and PD-L1/B7.1 complexes negatively regulates T-cell receptor signaling, resulting in the subsequent downregulation of T cell activation and suppression of anti-tumor immune activity. PD-L1 is over-expressed in many cancers, including a wide variety of solid tumors, such as bladder, breast, colon, lung, melanoma, ovarian, salivary, stomach, and thyroid tumors. PD-L1 over-expression in tumor cells may advance tumor invasion and is often associated with poor prognosis.

Given the role of PD-L1 in cancer development and immune system regulation, additional tools to detect the presence of PD-L1, for example for diagnosis and/or patient selection, are desirable.

SUMMARY

The present invention relates to anti-programmed death-ligand 1 (PD-L1) antibodies and methods of using the same.

In one aspect, the invention features an isolated antibody that specifically binds to PD-L1, wherein the antibody binds to an epitope comprising amino acid residues 279-290 of human PD-L1 polypeptide (SEQ ID NO: 1). In some embodiments, the antibody comprises the following hypervariable regions (HVRs): (a) an HVR-H1 comprising the amino acid sequence of SNGLT (SEQ ID NO: 2); (b) an HVR-H2 comprising the amino acid sequence of TINK-DASAYYASWAKG (SEQ ID NO: 3); and (c) an HVR-H3 comprising the amino acid sequence of IAFKTGTSI (SEQ ID NO: 4). In some embodiments, the antibody further comprises the following heavy chain variable domain framework regions (FRs): (a) FR-H1 comprising the amino acid sequence of QSLEESGGRLVKPDETLTITCTVSGIDLS (SEQ ID NO: 5); (b) FR-H2 comprising the amino acid sequence of WVRQAPGEGLEWIG (SEQ ID NO: 6); (c) FR-H3 comprising the amino acid sequence of RLTISKPSSTKVDLKITSPTTEDTATYFCGR (SEQ ID NO: 7); and (d) FR-H4 comprising the amino acid sequence of WGPGTLVTVSS (SEQ ID NO: 8). In some embodiments, the antibody further comprises the following HVRs: (a) an HVR-L1 comprising the amino acid sequence of QASESVYSNNYLS (SEQ ID NO: 9); (b) an HVR-L2 comprising the amino acid sequence of LASTLAS (SEQ ID NO: 10); and (c) an HVR-L3 comprising the amino acid sequence of IGGKSSSTDGNA (SEQ ID NO: 11). In some embodiments, the antibody further comprises the following light chain variable domain FRs: (a) FR-L1 comprising the amino acid sequence of AIVMTQTPSPVSAAVGGTVTINC (SEQ ID NO: 12); (b) FR-L2 comprising the amino acid sequence of WFQQKPGQPPKLLIY (SEQ ID NO: 13); (c) FR-L3 comprising the amino acid sequence of GVPSRFKGSGSGTQFTLTISGVQCDDAATYYC (SEQ ID NO: 14); and (d) FR-L4 comprising the amino acid sequence of FGGGTEVVVR (SEQ ID NO: 15). In some embodiments, the antibody comprises (a) a VH sequence having at least 95% sequence identity to the amino acid sequence of SEQ ID NO: 16; (b) a VL sequence having at least 95% sequence identity to the amino acid sequence of SEQ ID NO: 17; or (c) a VH sequence as in (a) and a VL sequence as in (b). In some embodiments, the antibody comprises a VH sequence of SEQ ID NO: 16. In some embodiments, the antibody comprises a VL sequence of SEQ ID NO: 17.

In other embodiments, the antibody comprises the following HVRs: (a) an HVR-L1 comprising the amino acid sequence of QASESVYSNNYLS (SEQ ID NO: 9); (b) an HVR-L2 comprising the amino acid sequence of LASTLAS (SEQ ID NO: 10); and (c) an HVR-L3 comprising the amino acid sequence of IGGKSSSTDGNA (SEQ ID NO: 11). In some embodiments, the antibody further comprises the following light chain variable domain FRs: (a) FR-L1 comprising the amino acid sequence of AIVMTQTPSPVSAAVGGTVTINC (SEQ ID NO: 12); (b) FR-L2 comprising the amino acid sequence of WFQQKPGQPPKLLIY (SEQ ID NO: 13); (c) FR-L3 comprising the amino acid sequence of GVPSRFKGSGSGTQFTLTISGVQCDDAATYYC (SEQ ID NO: 14); and (d) FR-L4 comprising the amino acid sequence of FGGGTEVVVR (SEQ ID NO: 15).

In another aspect, the invention features an isolated antibody that specifically binds PD-1, wherein the antibody comprises the following HVRs: (a) an HVR-H1 comprising the amino acid sequence of SNGLT (SEQ ID NO: 2); (b) an HVR-H2 comprising the amino acid sequence of TINK-DASAYYASWAKG (SEQ ID NO: 3); (c) an HVR-H3 comprising the amino acid sequence of IAFKTGTSI (SEQ ID NO: 4); (d) an HVR-L1 comprising the amino acid sequence of QASESVYSNNYLS (SEQ ID NO: 9); (e) an HVR-L2 comprising the amino acid sequence of LASTLAS (SEQ ID NO: 10); and (f) an HVR-L3 comprising the amino acid sequence of IGGKSSSTDGNA (SEQ ID NO: 11). In some embodiments, the antibody further comprises the following heavy chain variable domain and light chain variable domain FRs: (a) FR-H1 comprising the amino acid sequence of QSLEESGGRLVKPDETLTITCTVSGIDLS (SEQ ID NO: 5); (b) FR-H2 comprising the amino acid sequence of WVRQAPGEGLEWIG (SEQ ID NO: 6); (c) FR-H3 comprising the amino acid sequence of RLTISKPSSTKVDLKITSPTTEDTATYFCGR (SEQ ID NO: 7); (d) FR-H4 comprising the amino acid sequence of WGPGTLVTVSS (SEQ ID NO: 8); (e) FR-L1 comprising the amino acid sequence of AIVMTQTPSPVSAAVGGTVTINC (SEQ ID NO: 12); (f) FR-L2 comprising the amino acid sequence of WFQQKPGQPPKLLIY (SEQ ID NO: 13); (g) FR-L3 comprising the amino acid sequence of GVPSRFKGSGSGTQFTLTISGVQCDDAATYYC (SEQ ID NO: 14); and (h) FR-L4 comprising the amino acid sequence of FGGGTEVVVR (SEQ ID NO: 15). In some embodiments, the antibody comprises a VH sequence of SEQ ID NO: 16 and a VL sequence of SEQ ID NO: 17.

In another aspect, the invention features an isolated antibody that competes for binding to PD-L1 with any one of the preceding antibodies.

In another aspect, the invention features an isolated antibody that binds to the same epitope as any one of the preceding antibodies.

In some embodiments, any one of the preceding antibodies can be a monoclonal antibody. In some embodiments, the monoclonal antibody can be a rabbit monoclonal antibody.

In some embodiments, any one of the preceding antibodies can be an IgG antibody (e.g., an IgG1 antibody).

In some embodiments, any one of the preceding antibodies can be an antibody fragment that specifically binds PD-L1. In some embodiments, the antibody fragment is selected from the group consisting of Fab, single chain variable fragment (scFv), Fv, Fab', Fab'-SH, F(ab')$_2$, and diabody.

In another aspect, the invention features an immunoconjugate comprising any one of the preceding antibodies.

In another aspect, the invention features an isolated nucleic acid that encodes any of the antibodies described herein. In another aspect, the invention features a vector (e.g., an expression vector) comprising the nucleic acid for expressing the antibody. In another aspect, the invention features host cells comprising the preceding nucleic acids and/or vectors.

In some aspects, any one of the preceding antibodies can be for use in detecting the presence or expression level of PD-L1 in a biological sample. In some embodiments, the detecting is by immunohistochemistry (IHC), immunofluorescence (IF), flow cytometry, ELISA, or immunoblot. In some embodiments, the detecting is by IHC. In some embodiments, the sample comprises a fixed tissue. In some embodiments, the fixed tissue is a formalin-fixed paraffin-embedded (FFPE) tissue. In some embodiments, the sample is from a subject having, or at risk of, a cancer or an immune dysfunction. In some embodiments, the immune dysfunction is a T-cell dysfunctional disorder. In some embodiments, the T-cell dysfunctional disorder is an unresolved acute infection, chronic infection, or tumor immunity.

A further aspect of the invention is a method of detecting the presence or expression level of PD-L1 in a biological sample comprising contacting the biological sample with any one of the preceding antibodies and detecting the presence of the bound antibody. In some embodiments, the detecting is by IHC, IF, flow cytometry, ELISA, or immunoblot. In some embodiments, the detecting is by IHC. In some embodiments, the sample comprises a fixed tissue. In some embodiments, the fixed tissue is a FFPE tissue. In some embodiments, the sample is from a subject having, or at risk of, a cancer or an immune dysfunction. In some embodiments, the immune dysfunction is a T-cell dysfunctional disorder. In some embodiments, the T-cell dysfunctional disorder is an unresolved acute infection, chronic infection, or tumor immunity. In some embodiments, the sample is from a subject having a cancer. In some embodiments, the presence or expression level of PD-L1 in the sample indicates that the subject is likely to respond to treatment with an anti-cancer therapy. In some embodiments, the presence or expression level of PD-L1 in the sample indicates that the subject is more likely to respond to treatment with an anti-cancer therapy. In some embodiments, the presence or expression level of PD-L1 in the sample indicates the likelihood that the subject will exhibit benefit from treatment with an anti-cancer therapy. In some embodiments, the method further comprises selecting an anti-cancer therapy for the subject based on the presence or expression level of PD-L1 in the sample. In some embodiments, the method further comprises administering a therapeutically effective amount of an anti-cancer therapy to the subject. In some embodiments, the cancer is selected from the group consisting of non-small cell lung cancer, squamous cell cancer, small-cell lung cancer, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia, and head and neck cancer. In some embodiments, the cancer is non-small cell lung cancer (NSCLC). In some embodiments, the NSCLC is adenocarcinoma of the lung or squamous carcinoma of the lung. In some embodiments, the sample is a tumor sample. In some embodiments, the tumor sample comprises tumor-infiltrating immune cells, tumor cells, stromal cells, or any combination thereof. In some embodiments, the tumor sample has a detectable expression level of PD-L1 in tumor-infiltrating immune cells that comprise about 1% or more of the tumor sample by area. In some embodiments, the tumor sample has a detectable expression level of PD-L1 in tumor-infiltrating immune cells that comprise about 5% or more of the tumor sample by area. In some embodiments, the tumor sample has a detectable expression level of PD-L1 in tumor-infiltrating immune cells that comprise about 10% or more of the tumor sample by area. In some embodiments, the tumor sample has a detectable expression level of PD-L1 in about 1% or more of the tumor cells in the tumor sample. In some embodiments, the tumor sample has a detectable expression level of PD-L1 in about 5% or more of the tumor cells in the tumor sample. In some embodiments, the tumor sample has a detectable expression level of PD-L1 in about 10% or more of the tumor cells in the tumor sample. In some embodiments, the anti-cancer therapy comprises a PD-1 axis binding antagonist. In some embodiments, the PD-1 axis binding antagonist is selected from the group consisting of a PD-L1 binding antagonist, a PD-1 binding antagonist, and a PD-L2 binding antagonist. In some embodiments, the PD-1 axis binding antagonist is a PD-L1 binding antagonist. In some embodiments, the PD-L1 binding antagonist inhibits the binding of PD-L1 to one or more of its ligand binding partners. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody. In some embodiments, the antibody is selected from the group consisting of: YW243.55.S70, MPDL3280A (atezolizumab), MDX-1105, MEDI4736 (durvalumab), and MSB0010718C (avelumab). In some embodiments, the PD-1 axis binding antagonist is a PD-1 binding antagonist. In some embodiments, the PD-1 binding antagonist inhibits the binding of PD-1 to one or more of its ligand binding partners. In some embodiments, the PD-1 binding antagonist inhibits the binding of PD-1 to PD L1. In some embodiments, the PD-1 binding antagonist inhibits the binding of PD-1 to PD L2. In some embodiments, the PD-1 binding antagonist inhibits the binding of PD-1 to both PD-L1 and PD-L2. In some embodiments, the PD-1 binding antagonist is an antibody. In some embodiments, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some embodiments, the PD-1 binding antagonist is an Fc-fusion protein. In some embodiments, the Fc-fusion protein is AMP-224. In some embodiments, the method further comprises administering to the patient an effective amount of a second therapeutic agent. In some embodiments, the second therapeutic agent is selected from the group consisting of a cytotoxic agent, a growth-inhibitory agent, a radiation therapy agent, an anti-angiogenic agent, and combinations thereof. In some embodiments, the subject is a human.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

6

Figures 5A, 5B, 5C, 5D, 5E, 5F, 5G, 5H, 5I, 5J:
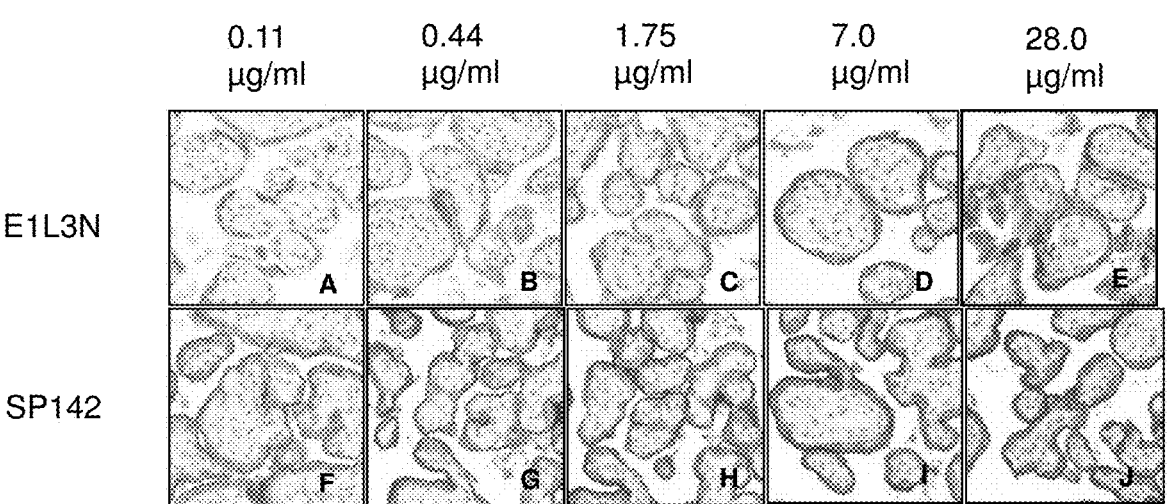
FIG. 5A is an image showing the results of IHC on a FFPE placental tissue section using anti-PD-L1 antibody E1L3N at a concentration of 0.11 µg/ml.

FIG. 5B is an image showing the results of IHC on a FFPE placental tissue section anti-PD-L1 antibody E1L3N at a concentration of 0.44 µg/ml.

FIG. 5C is an image showing the results of IHC on a FFPE placental tissue section using anti-PD-L1 antibody E1L3N at a concentration of 1.75 µg/ml.

FIG. 5D is an image showing the results of IHC on a FFPE placental tissue section using anti-PD-L1 antibody E1L3N at a concentration of 7.0 µg/ml.

FIG. 5E is an image showing the results of IHC on a FFPE placental tissue section using anti-PD-L1 antibody E1L3N at a concentration of 28.0 µg/ml.

FIG. 5F is an image showing the results of IHC on a FFPE placental tissue section using anti-PD-L1 antibody SP142 at a concentration of 0.11 µg/ml.

FIG. 5G is an image showing the results of IHC on a FFPE placental tissue section using anti-PD-L1 antibody SP142 at a concentration of 0.44 µg/ml.

FIG. 5H is an image showing the results of IHC on a FFPE placental tissue section using anti-PD-L1 antibody SP142 at a concentration of 1.75 µg/ml.

FIG. 5I is an image showing the results of IHC on a FFPE placental tissue section using anti-PD-L1 antibody SP142 at a concentration of 7.0 µg/ml.

FIG. 5J is an image showing the results of IHC on a FFPE placental tissue section using anti-PD-L1 antibody SP142 at a concentration of 28.0 µg/ml.

Figures 6A, 6T:
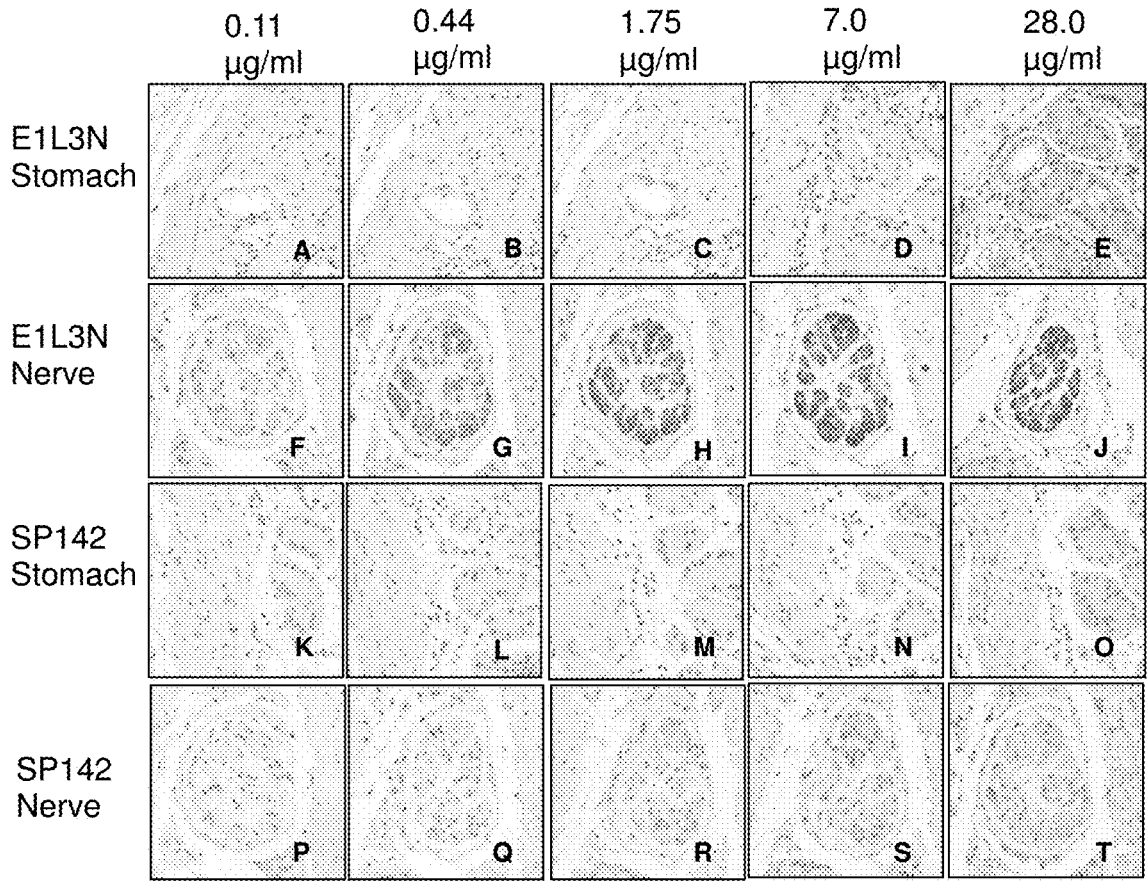

FIG. 6A is an image showing the results of IHC on a FFPE stomach epithelium tissue section using anti-PD-L1 antibody E1L3N at a concentration of 0.11 µg/ml.

FIG. 6B is an image showing the results of IHC on a FFPE stomach epithelium tissue section using anti-PD-L1 antibody E1L3N at a concentration of 0.44 µg/ml.

FIG. 6C is an image showing the results of IHC on a FFPE stomach epithelium tissue section using anti-PD-L1 antibody E1L3N at a concentration of 1.75 µg/ml.

FIG. 6D is an image showing the results of IHC on a FFPE stomach epithelium tissue section using anti-PD-L1 antibody E1L3N at a concentration of 7.0 µg/ml.

FIG. 6E is an image showing the results of IHC on a FFPE stomach epithelium tissue section using anti-PD-L1 antibody E1L3N at a concentration of 28.0 µg/ml.

FIG. 6F is an image showing the results of IHC on a FFPE nerve tissue section using anti-PD-L1 antibody E1L3N at a concentration of 0.11 µg/ml.

FIG. 6G is an image showing the results of IHC on a FFPE nerve tissue section using anti-PD-L1 antibody E1L3N at a concentration of 0.44 µg/ml.

FIG. 6H is an image showing the results of IHC on a FFPE nerve tissue section using anti-PD-L1 antibody E1L3N at a concentration of 1.75 µg/ml.

FIG. 6I is an image showing the results of IHC on a FFPE nerve tissue section using anti-PD-L1 antibody E1L3N at a concentration of 7.0 µg/ml.

FIG. 6J is an image showing the results of IHC on a FFPE nerve tissue section using anti-PD-L1 antibody E1L3N at a concentration of 28.0 µg/ml.

FIG. 6K is an image showing the results of IHC on a FFPE stomach epithelium tissue section using anti-PD-L1 antibody SP142 at a concentration of 0.11 µg/ml.

FIG. 6L is an image showing the results of IHC on a FFPE stomach epithelium tissue section using anti-PD-L1 antibody SP142 at a concentration of 0.44 µg/ml.

FIG. 6M is an image showing the results of IHC on a FFPE stomach epithelium tissue section using anti-PD-L1 antibody SP142 at a concentration of 1.75 µg/ml.

FIG. 6N is an image showing the results of IHC on a FFPE stomach epithelium tissue section using anti-PD-L1 antibody SP142 at a concentration of 7.0 µg/ml.

FIG. 6O is an image showing the results of IHC on a FFPE stomach epithelium tissue section using anti-PD-L1 antibody SP142 at a concentration of 28.0 µg/ml.

FIG. 6P is an image showing the results of IHC on a FFPE nerve tissue section using anti-PD-L1 antibody SP142 at a concentration of 0.11 µg/ml.

FIG. 6Q is an image showing the results of IHC on a FFPE nerve tissue section using anti-PD-L1 antibody SP142 at a concentration of 0.44 µg/ml.

FIG. 6R is an image showing the results of IHC on a FFPE nerve tissue section using anti-PD-L1 antibody SP142 at a concentration of 1.75 µg/ml.

FIG. 6S is an image showing the results of IHC on a FFPE nerve tissue section using anti-PD-L1 antibody SP142 at a concentration of 7.0 µg/ml.

FIG. 6T is an image showing the results of IHC on a FFPE nerve tissue section using anti-PD-L1 antibody SP142 at a concentration of 28.0 µg/ml.

Figures 7A, 7B, 7C, 7D, 7E, 7F, 7G, 7H, 7I, 7J:
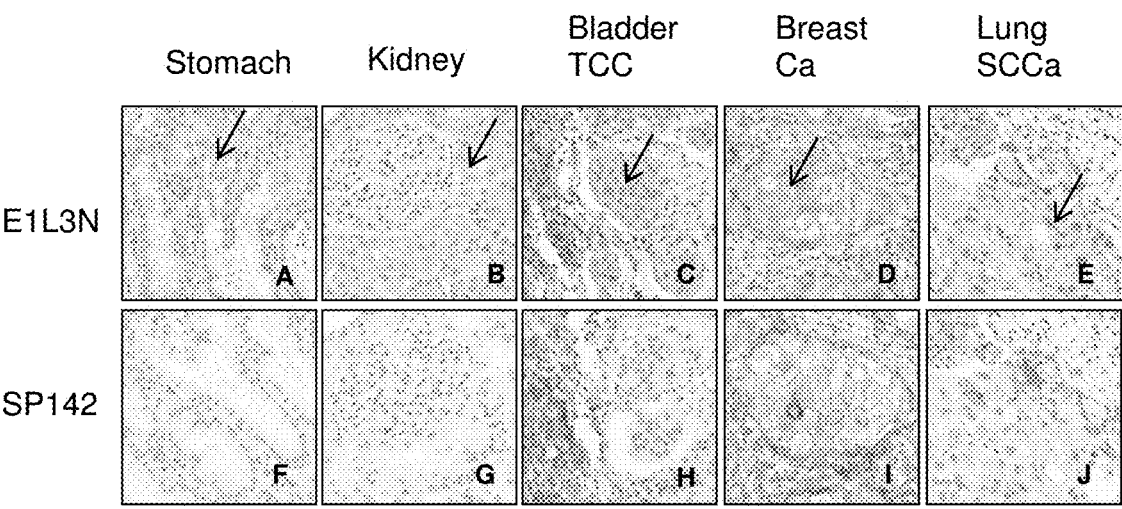

FIG. 7A is an image showing the results of IHC on a FFPE stomach epithelium tissue section using anti-PD-L1 antibody E1L3N.

FIG. 7B is an image showing the results of IHC on a FFPE kidney tissue section using anti-PD-L1 antibody E1L3N.

FIG. 7C is an image showing the results of IHC on a FFPE bladder transitional cell carcinoma (TCC) tissue section using anti-PD-L1 antibody E1L3N.

FIG. 7D is an image showing the results of IHC on a FFPE breast ductal carcinoma (Ca) tissue section using anti-PD-L1 antibody E1L3N.

FIG. 7E is an image showing the results of IHC on a FFPE lung squamous cell carcinoma tissue section using anti-PD-L1 antibody E1L3N.

FIG. 7F is an image showing the results of IHC on a FFPE stomach epithelium tissue section using anti-PD-L1 antibody SP142.

FIG. 7G is an image showing the results of IHC on a FFPE kidney tissue section using anti-PD-L1 antibody SP142.

FIG. 7H is an image showing the results of IHC on a FFPE bladder transitional cell carcinoma (TCC) tissue section using anti-PD-L1 antibody SP142.

FIG. 7I is an image showing the results of IHC on a FFPE breast ductal carcinoma (Ca) tissue section using anti-PD-L1 antibody SP142.

FIG. 7J is an image showing the results of IHC on a FFPE lung squamous cell carcinoma tissue section using anti-PD-L1 antibody SP142.

Figures 8A, 8B, 8C, 8D, 8E, 8F, 8G, 8H, 8I, 8J, 8K, 8L:
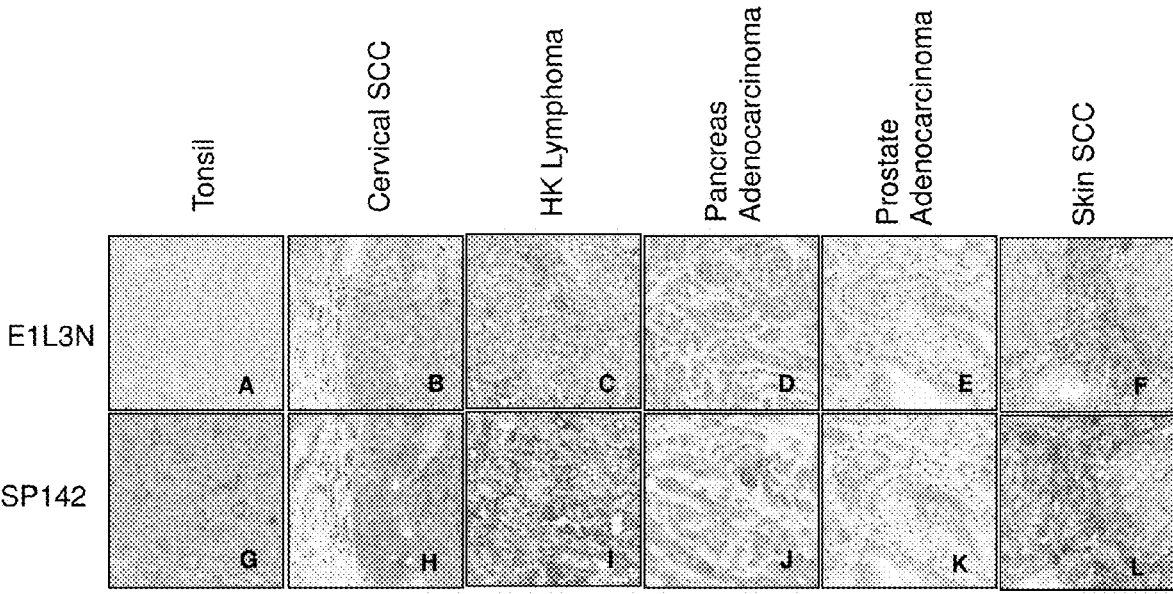

FIG. 8A is an image showing the results of IHC on a FFPE tonsil tissue section using anti-PD-L1 antibody E1L3N.

FIG. 8B is an image showing the results of IHC on a FFPE cervical squamous cell carcinoma (SCC) tissue section using anti-PD-L1 antibody E1L3N.

FIG. 8C is an image showing the results of IHC on a FFPE Hodgkin Lymphoma (HK lymphoma) tissue section using anti-PD-L1 antibody E1L3N.

FIG. 8D is an image showing the results of IHC on a FFPE pancreatic adenocarcinoma tissue section using anti-PD-L1 antibody E1L3N.

FIG. 8E is an image showing the results of IHC on a FFPE prostate adenocarcinoma tissue section using anti-PD-L1 antibody E1L3N.

FIG. 8F is an image showing the results of IHC on a FFPE skin SCC tissue section using anti-PD-L1 antibody E1L3N.

FIG. 8G is an image showing the results of IHC on a FFPE tonsil tissue section using anti-PD-L1 antibody SP142.

FIG. 8H is an image showing the results of IHC on a FFPE cervical squamous cell carcinoma (SCC) tissue section using anti-PD-L1 antibody SP142.

FIG. 8I is an image showing the results of IHC on a FFPE Hodgkin Lymphoma (HK lymphoma) tissue section using anti-PD-L1 antibody SP142.

FIG. 8J is an image showing the results of IHC on a FFPE pancreatic adenocarcinoma tissue section using anti-PD-L1 antibody SP142.

FIG. 8K is an image showing the results of IHC on a FFPE prostate adenocarcinoma tissue section using anti-PD-L1 antibody SP142.

FIG. 8L is an image showing the results of IHC on a FFPE skin SCC tissue section using anti-PD-L1 antibody SP142.

Figures 9A, 9B, 9C, 9D, 9E, 9F, 9G, 9H, 9I, 9J:
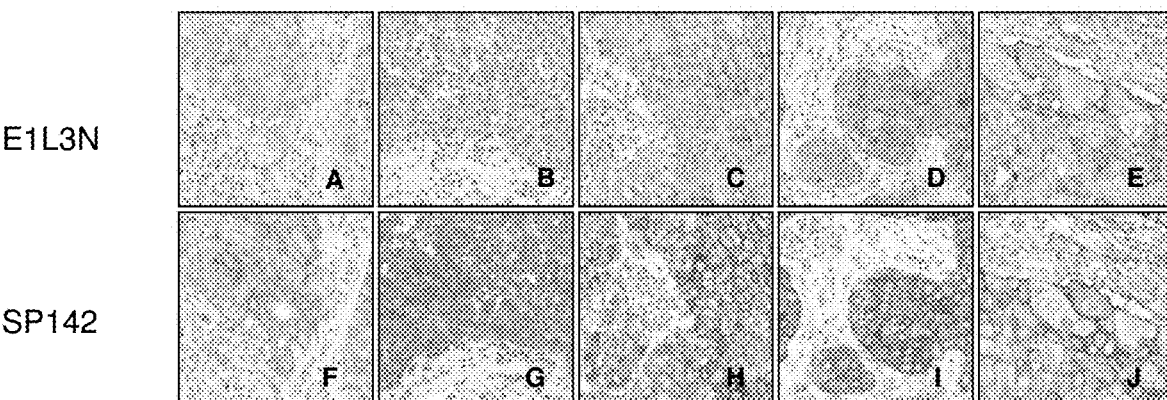

FIG. 9A is an image showing the results of IHC on a FFPE tissue section from a NSCLC patient using anti-PD-L1 antibody E1L3N.

FIG. 9B is an image showing the results of IHC on a FFPE tissue section from a NSCLC patient using anti-PD-L1 antibody E1L3N.

FIG. 9C is an image showing the results of IHC on a FFPE tissue section from a NSCLC patient using anti-PD-L1 antibody E1L3N.

FIG. 9D is an image showing the results of IHC on a FFPE tissue section from a NSCLC patient using anti-PD-L1 antibody E1L3N.

FIG. 9E is an image showing the results of IHC on a FFPE tissue section from a NSCLC patient using anti-PD-L1 antibody E1L3N.

FIG. 9F is an image showing the results of IHC on a FFPE tissue section from a NSCLC patient using anti-PD-L1 antibody SP142.

FIG. 9G is an image showing the results of IHC on a FFPE tissue section from a NSCLC patient using anti-PD-L1 antibody SP142.

FIG. 9H is an image showing the results of IHC on a FFPE tissue section from a NSCLC patient using anti-PD-L1 antibody SP142.

FIG. 9I is an image showing the results of IHC on a FFPE tissue section from a NSCLC patient using anti-PD-L1 antibody SP142.

FIG. 9J is an image showing the results of IHC on a FFPE tissue section from a NSCLC patient using anti-PD-L1 antibody SP142.

Figure 10:
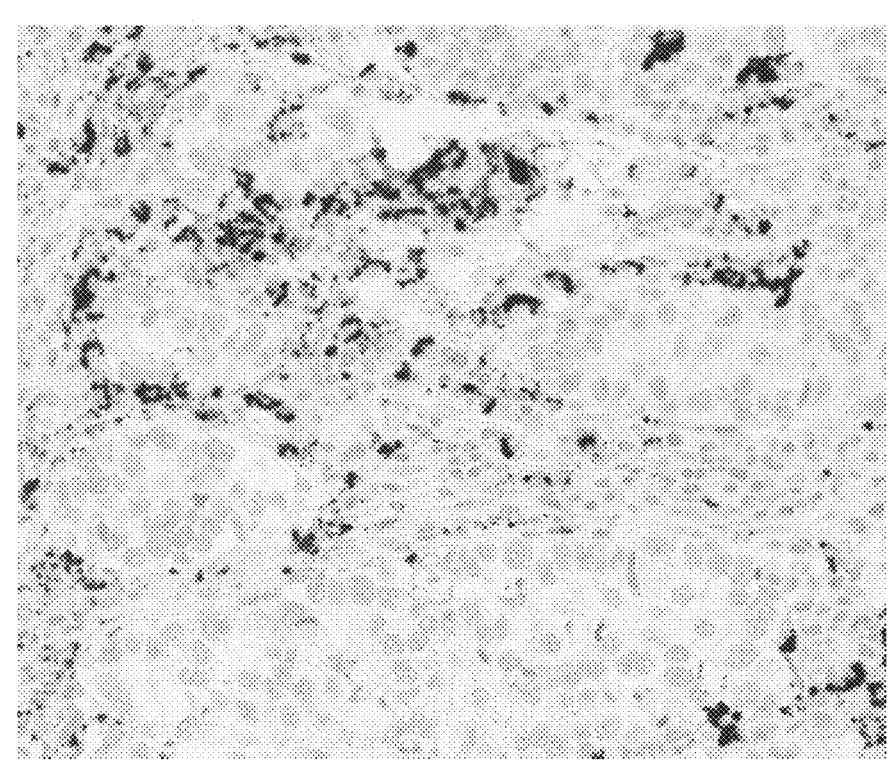

FIG. 10 is an image showing the results of IHC on a FFPE tissue section from a NSCLC patient using anti-PD-L1 antibody SP142. The image shows PD-L1-positive tumor-infiltrating immune cells (ICs, dark brown staining) present as aggregates in the tumor stroma. The tissue section was counter-stained with hematoxylin (blue).

Figure 11:
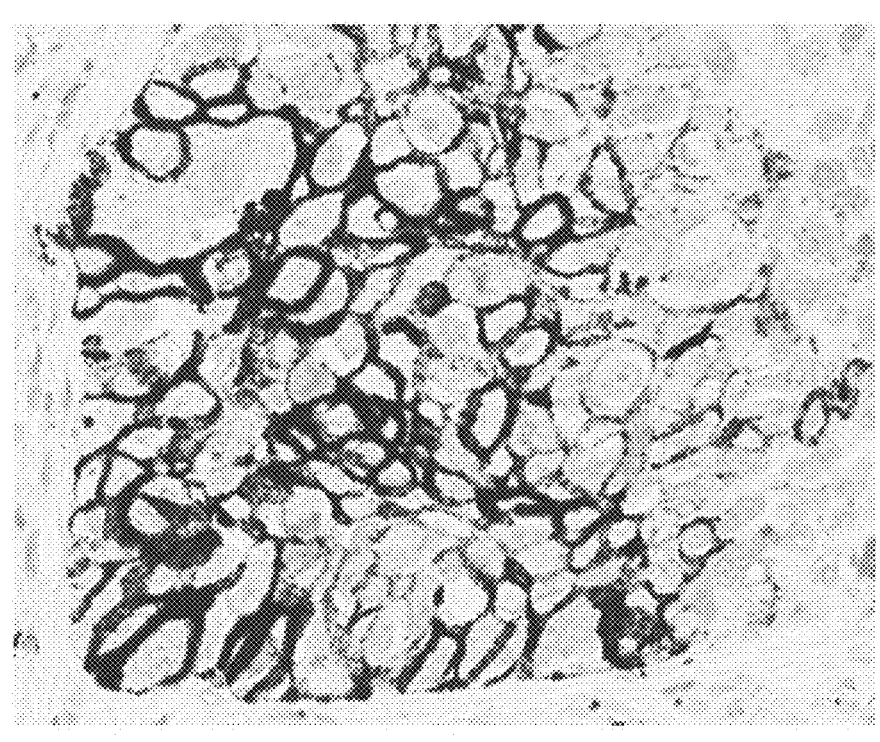

FIG. 11 is an image showing the results of IHC on a FFPE tissue section from a NSCLC patient using anti-PD-L1 antibody SP142. The image shows PD-L1-positive tumor cell (TC) staining. PD-L1 signal is shown in dark brown. The tissue section was counter-stained with hematoxylin (blue).

FIG. 12A is an image showing regions of stroma and tumor area in an H&E-stained NSCLC tumor resection specimen. Arrows indicate peritumoral stroma, tumor cell mass, and intratumoral stroma. The black line outlines the edge of the tumor area. The image was taken at a higher magnification power.

FIGS. 12B-12C are images showing tumor area of an NSCLC resection specimen. Serial sections of the tumor specimen were stained with H&E (FIG. 12B) or by PD-L1 IHC using the SP142 antibody (FIG. 12C). PD-L1 signal in FIG. 12C is shown as dark brown. The blue line outlines the tumor area (see Example 5). These images correspond to the same specimen shown in FIG. 12A but were taken at a lower magnification power.

FIG. 13 is a schematic showing an exemplary workflow for determining the percentage of tumor area covered by PD-L1-positive tumor-infiltrating immune cells (IC %). In this example, the IC % was estimated visually to be 10%.

Figure 14A:
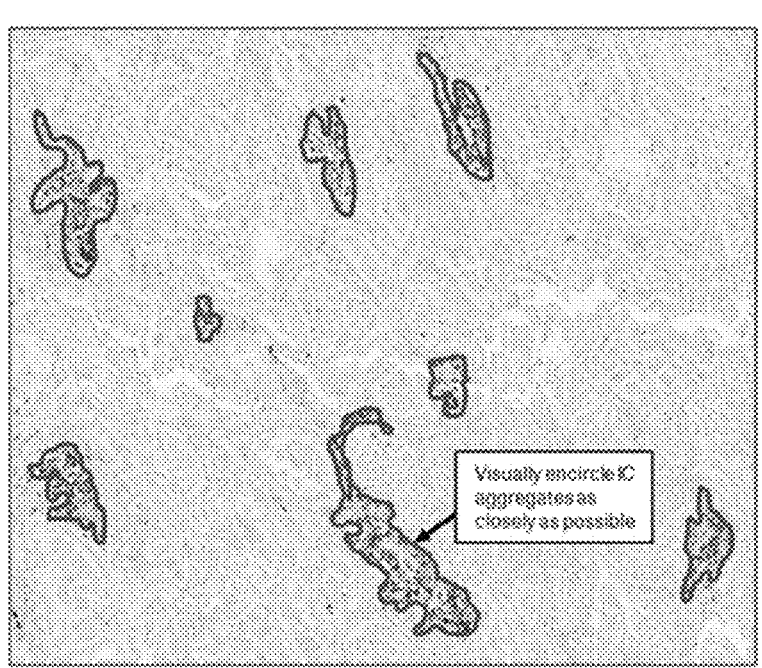
Figure 14B:
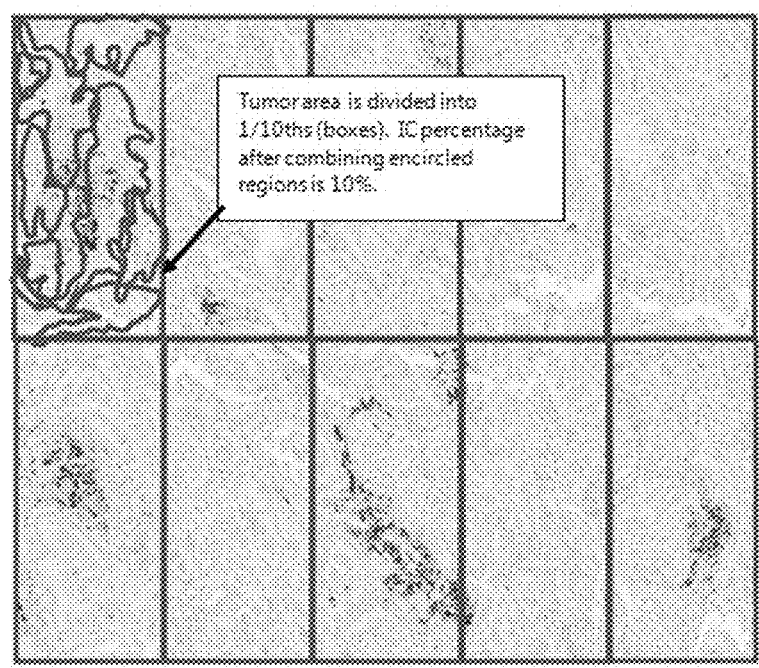

FIGS. 14A-14B show an exemplary scoring method for PD-L1 IHC with a PD-L1-positive IC aggregate staining pattern. FIG. 14A shows that the PD-L1-positive IC aggregates (dark brown signal) were visually encircled as closely as possible, generating outlines of each PD-L1-positive IC aggregate (blue outlines). These regions were combined, and the combined area as a percentage of tumor area was estimated (FIG. 14B). In FIG. 14B, the tumor area was divided into $\frac{1}{10}^{ths}$ (boxes), and the outlines of PD-L1-positive IC aggregates from FIG. 14A were combined. The outlines filled one of the boxes, and therefore in this example, the percentage of tumor area covered by PD-L1-positive ICs was estimated to be 10%. The images show the results of IHC on FFPE tissue sections from NSCLC patients using anti-PD-L1 antibody SP142.

Figure 15A:
Figure 15B:
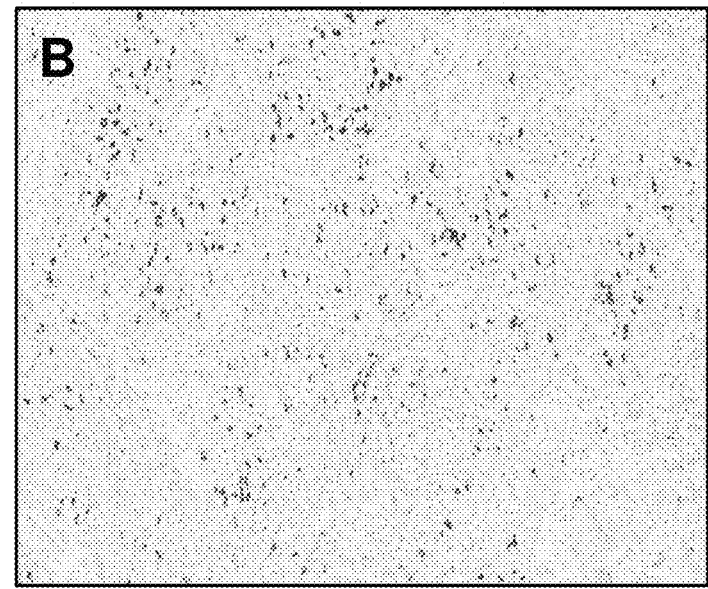

FIGS. 15A-15B show images with a single cell spread PD-L1-positive IC staining pattern. In this example, the images were scored based on the density of single cell spread by comparison to reference images (see, e.g., FIG. 16). FIG. 15A shows an image in which the cell density for single cell spread PD-L1-positive ICs was 1%. FIG. 15B shows an image in which the cell density for single cell spread PD-L1-positive ICs was 5%. The images show the results of IHC on FFPE tissue sections from NSCLC patients using anti-PD-L1 antibody SP142.

Figures 16A, 16B, 16C, 16D, 16E, 16F, 16G, 16H:
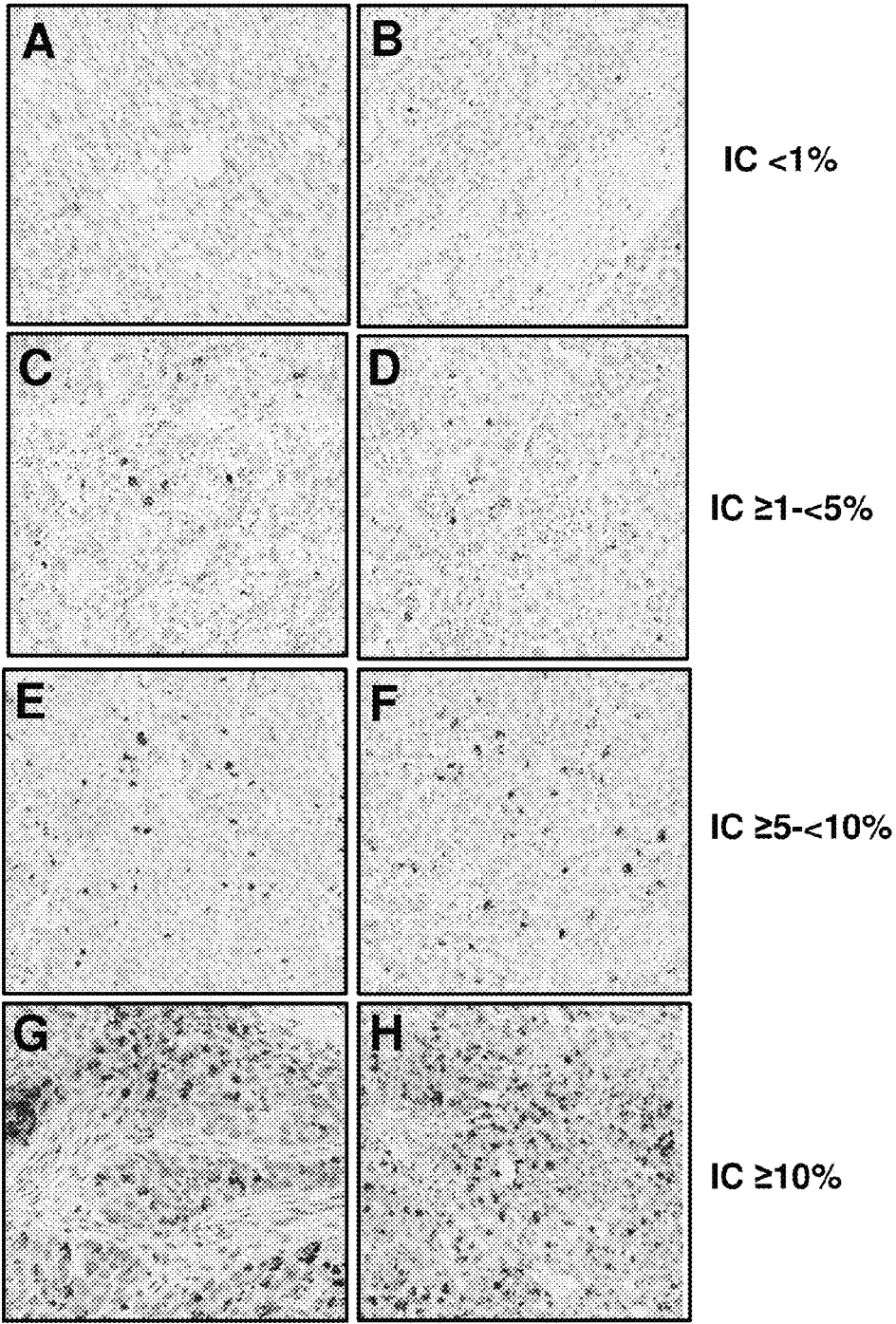

FIGS. 16A-16H show exemplary reference images for single cell spread PD-L1-positive IC staining pattern at the indicated PD-L1 IC expression cutoffs. The images show the results of IHC on FFPE tissue sections from NSCLC patients using anti-PD-L1 antibody SP142. FIGS. 16A-16B show images in which the PD-L1-positive IC % was less than 1%. FIGS. 16C-16D show images in which the PD-L1-positive IC % was greater than or equal to 1% to less than 5%. FIGS. 16E-16F show images in which the PD-L1-positive IC % was greater than or equal to 5% to less than 10%. FIGS. 16G-16H show images in which the PD-L1-positive IC % was greater than or equal to 10%.

Figure 17A:
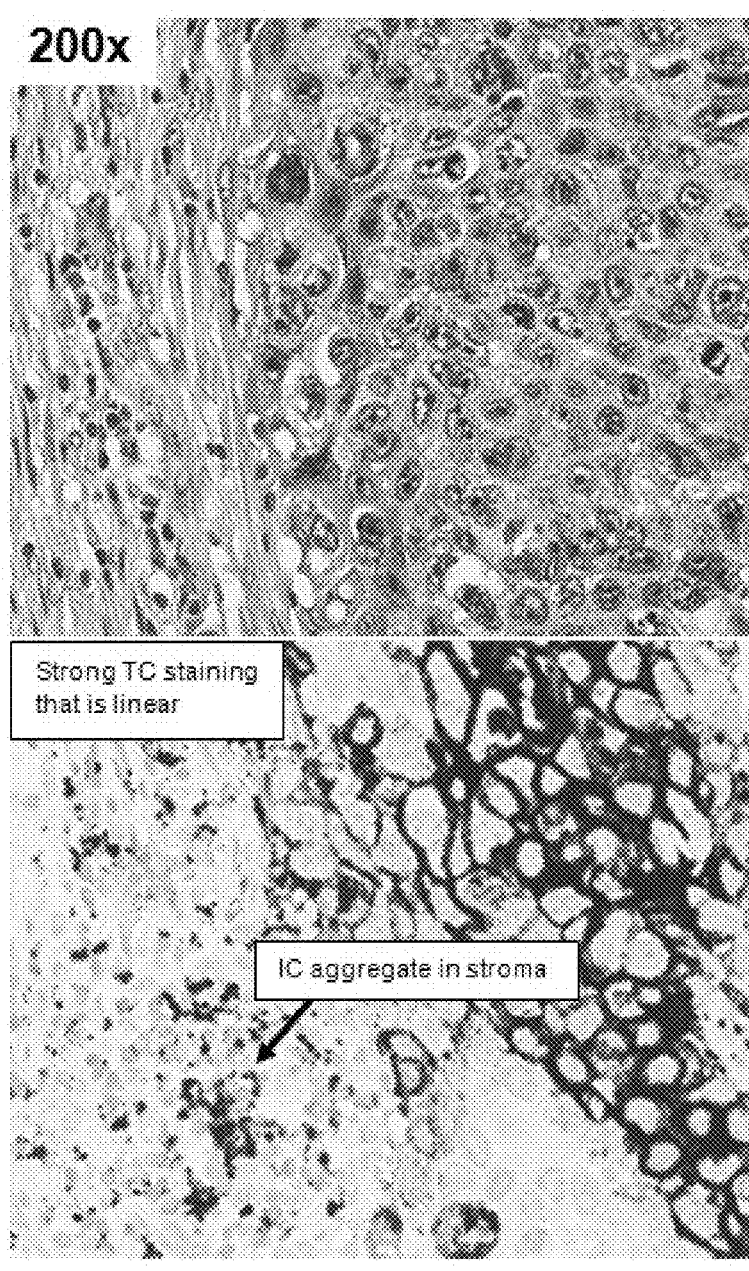

FIG. 17A shows images of FFPE tissue serial sections from NSCLC patients that were H&E-stained (top) or processed for IHC using anti-PD-L1 antibody SP142 (bottom). In this example, no intratumoral ICs were detected in the H&E-stained section, and strong TC PD-L1 staining was detected by IHC. ICs were scored in stroma (arrow).

Figure 17B:
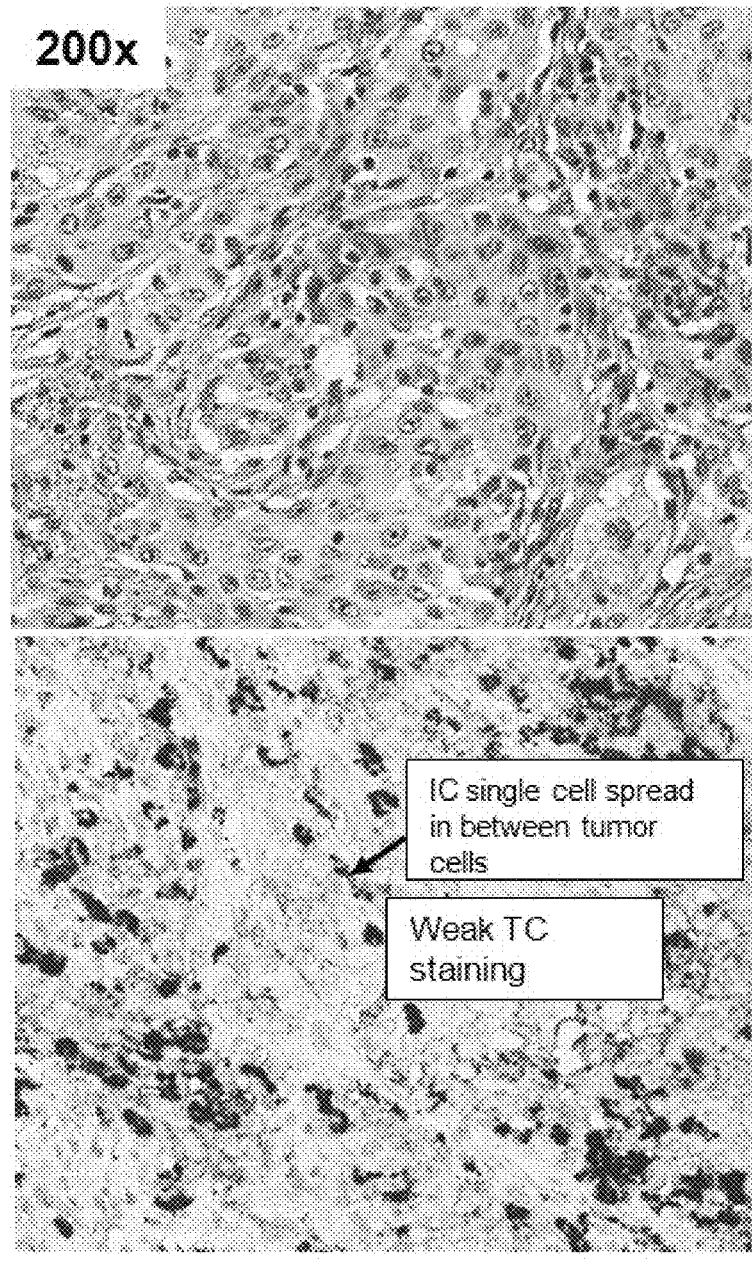

FIG. 17B show images of FFPE tissue serial sections from NSCLC patients that were H&E-stained (top) or processed for IHC using anti-PD-L1 antibody SP142 (bottom). In this example, intratumoral ICs were detected in the H&E-stained section, and weak-to-moderate TC PD-L1 staining was detected by IHC. ICs were scored in both stroma and tumor cell groups.

Figure 17C:
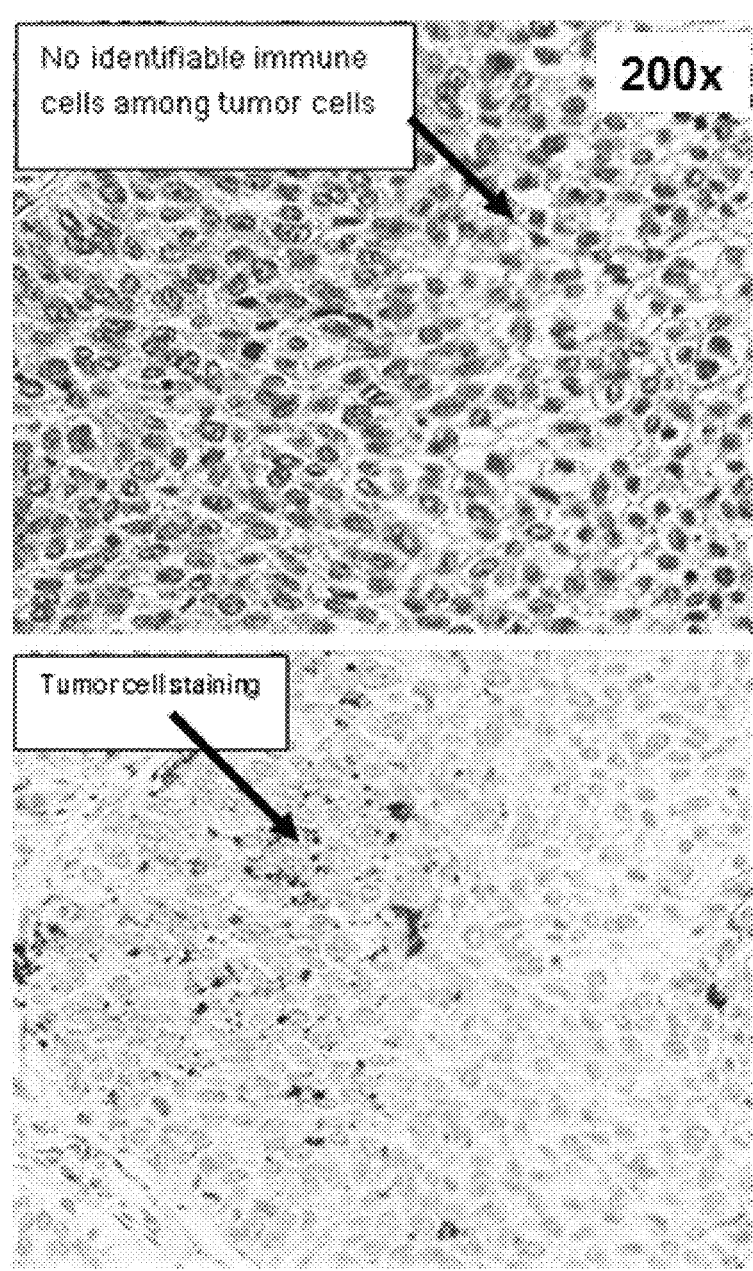

FIG. 17C shows images of FFPE tissue serial sections from NSCLC patients that were H&E-stained (top) or processed for IHC using anti-PD-L1 antibody SP142 (bottom). In this example, no intratumoral ICs were detected in the H&E stained section, and granular PD-L1 TC staining was detected by IHC. The granular staining was scored as PD-L1-positive TCs as long as the staining was arranged in a linear fashion (i.e., along the outline of the cell membrane).

Figures 18A, 18B, 18C, 18D, 18E, 18F:
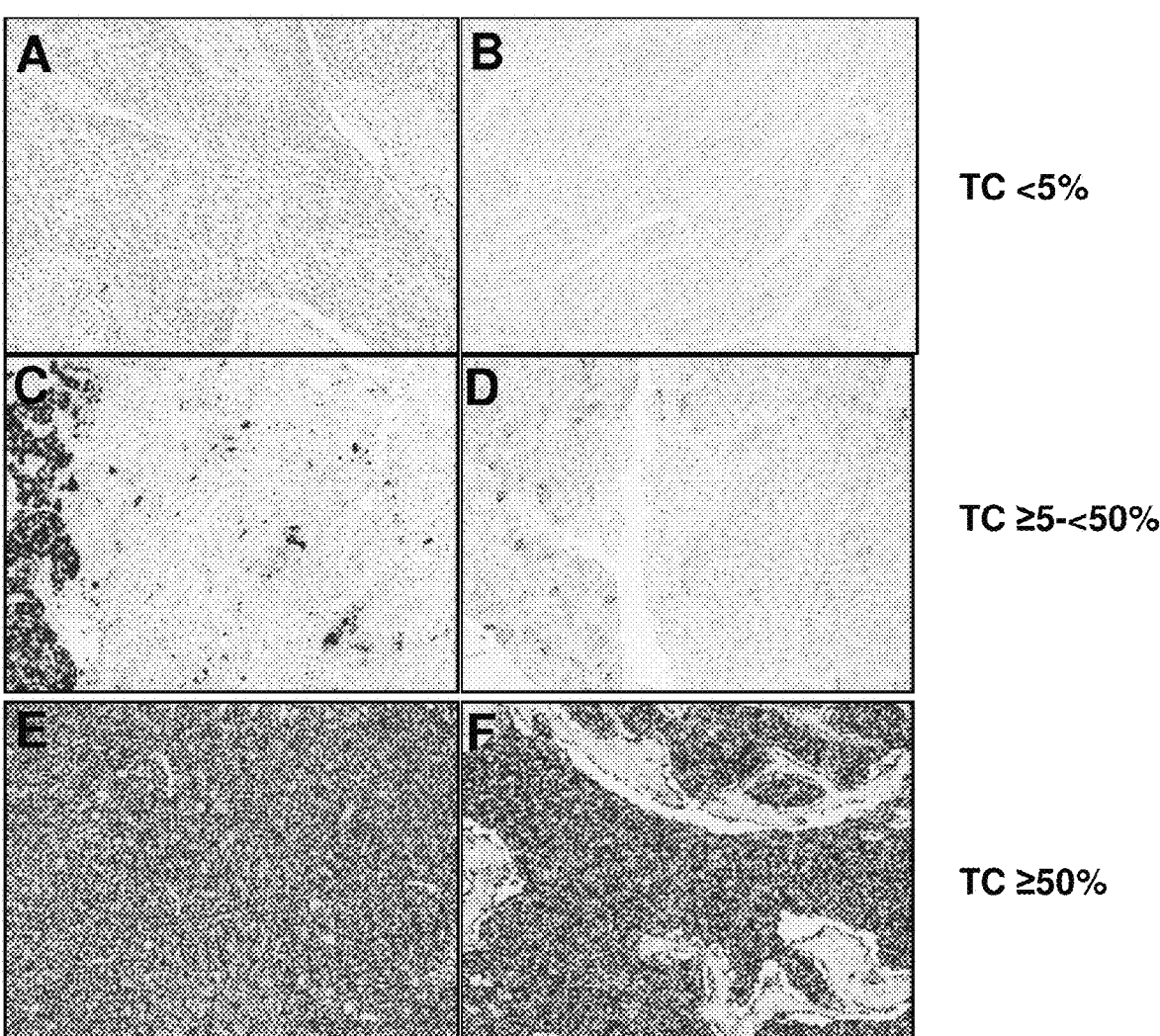

FIGS. 18A-18F show exemplary images for PD-L1-positive TC staining pattern at the indicated PD-L1 TC % cutoffs. The images show the results of IHC on FFPE tissue sections from NSCLC patients using anti-PD-L1 antibody SP142. FIGS. 18A-18B show images in which the TC % was less than 5%. FIGS. 18C-18D show images in which the TC % was greater than or equal to 5% to less than 50%. FIGS. 18E-18F show images in which the TC % was greater than or equal to 50%.

DETAILED DESCRIPTION OF EMBODIMENTS OF THE INVENTION

I. Definitions

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "anergy" refers to the state of unresponsiveness to antigen stimulation resulting from incomplete or insufficient signals delivered through the T-cell receptor (e.g., increase in intracellular $Ca^{+2}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overriden by the presence of interleukin-2. Anergic T-cells do not undergo clonal expansion and/or acquire effector functions.

The term "anti-cancer therapy" refers to a therapy useful in treating cancer. Examples of anti-cancer therapeutic agents include, but are limited to, cytotoxic agents, chemotherapeutic agents, growth inhibitory agents, agents used in radiation therapy, anti-angiogenesis agents, apoptotic agents, anti-tubulin agents, and other agents to treat cancer, for example, PD-1 axis binding antagonists, anti-CD20 antibodies, platelet derived growth factor inhibitors (e.g., GLEEVEC™ (imatinib mesylate)), a COX-2 inhibitor (e.g., celecoxib), interferons, cytokines, antagonists (e.g., neutralizing antibodies) that bind to one or more of the following targets PDGFR-β, BlyS, APRIL, BCMA receptor(s), TRAIL/Apo2, other bioactive and organic chemical agents, and the like. Combinations thereof are also included in the invention.

The terms "anti-PD-L1 antibody," "anti-PD-L1 antibody," "antibody that specifically binds to PD-L1," and "antibody that binds to PD-L1" refer to an antibody that is capable of binding PD-L1 with sufficient affinity such that the antibody is useful as a diagnostic and/or therapeutic agent in targeting PD-L1. In one embodiment, the extent of binding of an anti-PD-L1 antibody to an unrelated, non-PD-L1 protein is less than about 10% of the binding of the antibody to PD-L1 as measured, e.g., by a radioimmunoassay (RIA). In certain embodiments, an antibody that binds to PD-L1 has a dissociation constant (Kd) of $\leq 1$ $\mu$M, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-PD-L1 antibody binds to an epitope of PD-L1 that is conserved among PD-L1 from different species.

The terms "anti-PD-1 antibody" and "an antibody that binds to PD-1" refer to an antibody that is capable of binding PD-1 with sufficient affinity such that the antibody is useful as a diagnostic and/or therapeutic agent in targeting PD-1. In one embodiment, the extent of binding of an anti-PD-1 antibody to an unrelated, non-PD-1 protein is less than about 10% of the binding of the antibody to PD-1 as measured, for example, by a radioimmunoassay (RIA). In certain embodiments, an antibody that binds to PD-1 has a dissociation constant (Kd) of $\leq 1$ $\mu$M, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, e.g., from $10^{-9}$ M to $10^{-13}$ M). In certain embodiments, an anti-PD-1 antibody binds to an epitope of PD-1 that is conserved among PD-1 from different species. Exemplary anti-PD-1 antibodies include, but are not limited to, MDX 1106 (nivolumab), MK-3475 (pembrolizumab), and CT-011 (pidilizumab).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')₂; diabodies; linear antibodies; single-chain antibody molecules (e.g. scFv); and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')₂ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen)

has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')₂ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

An "autoimmune disease" is a disease or disorder arising from and directed against an individual's own tissues or organs or a co-segregation or manifestation thereof or resulting condition therefrom. Autoimmune diseases can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease that can affect multiple organ systems (for example, systemic lupus erythematosus (SLE), rheumatoid arthritis (RA), polymyositis, etc.). Non-limiting exemplary autoimmune diseases include autoimmune rheumatologic disorders (such as, for example, RA, Sjogren's syndrome, scleroderma, lupus such as SLE and lupus nephritis, polymyositis-dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-negative vasculitis and ANCA-associated vasculitis, including Churg-Strauss vasculitis, Wegener's granulomatosis, and microscopic polyangiitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, RA, ulcerative colitis, ANCA-associated vasculitis, lupus, multiple sclerosis, Sjogren's syndrome, Graves' disease, IDDM, pernicious anemia, thyroiditis, and glomerulonephritis.

The phrase "based on" when used herein means that the information about one or more biomarkers (e.g., PD-L1) is used to inform a treatment decision, information provided on a package insert, or marketing/promotional guidance, for example.

By "biological sample" is meant a collection of similar cells obtained from a subject or patient. A biological sample can be a tissue or a cell sample. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The biological sample can also be obtained from in vitro tissue or cell culture. The tissue sample may contain compounds which are not naturally intermixed with the tissue in nature such as preservatives, anticoagulants, buffers, fixatives, nutrients, antibiotics, or the like. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

The term "biomarker" as used herein refers to an indicator, e.g., predictive, diagnostic, and/or prognostic, which can be detected in a sample, for example, PD-L1. The biomarker may serve as an indicator of a particular subtype of a disease or disorder (e.g., cancer) characterized by certain, molecular, pathological, histological, and/or clinical features. In some embodiments, a biomarker is a gene. Biomarkers include, but are not limited to, polynucleotides (e.g., DNA and/or RNA), polynucleotide copy number alterations (e.g., DNA copy numbers), polypeptides, polypeptide and polynucleotide modifications (e.g., post-translational modifications), carbohydrates, and/or glycolipid-based molecular markers.

A "blocking" antibody or an "antagonist" antibody is one which inhibits or reduces biological activity of the antigen it binds. Preferred blocking antibodies or antagonist antibodies substantially or completely inhibit the biological activity of the antigen.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include non-small cell lung cancer (NSCLC) (including adenocarcinoma of the lung and squamous carcinoma of the lung), squamous cell cancer, small-cell lung cancer, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer. In particular embodiments, the cancer is NSCLC. In some embodiments, the NSCLC is adenocarcinoma of the lung or squamous carcinoma of the lung. The NSCLC may be squamous NSCLC or non-squamous NSCLC.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Illinois), and TAXOTERE® docetaxel (Rhône-Poulenc Rorer, Antony, France); chlorambucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called $\alpha$, $\delta$, $\varepsilon$, $\gamma$, and $\mu$, respectively.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression analysis or protocol to determine whether a specific therapeutic regimen should be performed. With respect to the embodiment of polynucleotide analysis or protocol, one may use the results of the polynucleotide expression analysis or protocol to determine whether a specific therapeutic regimen should be performed.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

The term "detection" includes any means of detecting, including direct and indirect detection.

The term "diagnosis" is used herein to refer to the identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathologi-cal criteria, or by molecular features (e.g., a subtype char-acterized by expression of one or a combination of biomark-ers (e.g., particular genes or proteins encoded by said genes)).

A "disorder" is any condition that would benefit from treatment including, but not limited to, chronic and acute disorders or diseases including those pathological conditions which predispose the mammal to the disorder in question.

"Effector functions" refer to those biological activities attributable to the Fc region of an antibody, which vary with the antibody isotype. Examples of antibody effector func-tions include: C1q binding and complement dependent cyto-toxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest.* 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full-length antibody," "intact antibody," and "whole antibody" are used herein interchangeably to refer to an antibody having a structure substantially similar to a native antibody structure or having heavy chains that contain an Fc region as defined herein.

The terms "level of expression" or "expression level" in general are used interchangeably and generally refer to the amount of a polynucleotide, mRNA, or an amino acid product or protein in a biological sample. "Expression" generally refers to the process by which gene-encoded information is converted into the structures present and operating in the cell. Therefore, according to the invention "expression" of a gene (e.g., the PD-L1 gene) may refer to transcription into a polynucleotide, translation into a protein, or even posttranslational modification of the protein. Frag-ments of the transcribed polynucleotide, the translated pro-tein, or the post-translationally modified protein shall also be regarded as expressed whether they originate from a tran-script generated by alternative splicing or a degraded tran-script, or from a post-translational processing of the protein, e.g., by proteolysis. In some embodiments, "expression level" refers to amount of a protein (e.g., PD-L1) in a biological sample as determined using methods known in the art or described herein, including but not limited to immunohistochemistry (IHC), immunoblotting (e.g., West-ern blotting), immunofluorescence (IF), flow cytometry, for example Fluorescence-Activated Cell Sorting (FACS™), or Enzyme-Linked Immunosorbant Assay (ELISA).

"Increased expression," "increased expression level," "increased levels," "elevated expression," "elevated expres-sion levels," or "elevated levels" refers to an increased expression or increased levels of a biomarker in an indi-vidual relative to a control, such as an individual or indi-viduals who are not suffering from the disease or disorder (e.g., cancer) or an internal control (e.g., a housekeeping biomarker).

"Decreased expression," "decreased expression level," "decreased levels," "reduced expression," "reduced expres-sion levels," or "reduced levels" refers to a decrease expres-sion or decreased levels of a biomarker in an individual relative to a control, such as an individual or individuals who are not suffering from the disease or disorder (e.g., cancer) or an internal control (e.g., a housekeeping biomarker). In some embodiments, reduced expression is little or no expression.

The terms "host cell," "host cell line," and "host cell culture" are used interchangeably and refer to cells into which exogenous nucleic acid has been introduced, includ-ing the progeny of such cells. Host cells include "transfor-mants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This defini-tion of a human antibody specifically excludes a humanized antibody comprising non-human antigen-binding residues.

A "human consensus framework" is a framework which represents the most commonly occurring amino acid resi-dues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest.* Fifth Edition, NIH Pub-lication 91-3242, Bethesda MD, Vols. 1-3, 1991. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodi-ments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia et al. *J. Mol. Biol.* 196: 901-917, 1987);

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest.* 5th Ed. Public Health Service, National Institutes of Health, Bethesda, MD, 1991);

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745, 1996); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3). Unless otherwise indicated, HVR residues and other residues in the variable domain (e.g., FR residues) are numbered herein according to Kabat et al., supra.

An "immune dysfunction" is a disorder or condition affecting the immune system and includes, for example, autoimmune diseases and T-cell dysfunctional disorders.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG1, IgG2 (including IgG2A and IgG2B), IgG3, or IgG4 subtypes, IgA (including IgA1 and IgA2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130. For example, useful immunoadhesins as medicaments useful for therapy herein include polypeptides that comprise the extracellular domain (ECD) or PD-1-binding portions of PD-L1 or PD-L2, or the extracellular or PD-L1- or PD-L2-binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, and the like. The two portions may be linked directly by a single peptide bond or through a peptide linker but are in reading frame with each other.

An "immunoconjugate" is an antibody conjugated to one or more heterologous molecule(s), including but not limited to a cytotoxic agent.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al. *J. Chromatogr. B.* 848: 79-87, 2007.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-PD-L1 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The word "label" when used herein refers to a compound or composition that is conjugated or fused directly or indirectly to a reagent such as a polynucleotide probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. The term is intended to encompass direct labeling of a probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "programmed cell death 1 ligand 1," "PD-L1," "programmed death-ligand 1," "cluster of differentiation 274," "CD274," or "B7 homolog 1," as used herein, refers to any native PD-L1 from any vertebrate source, including mammals such as primates (e.g., humans) and rodents (e.g., mice and rats), unless otherwise indicated. The term encompasses "full-length," unprocessed PD-L1 as well as any form of PD-L1 that results from processing in the cell. PD-L1 can exist as a transmembrane protein or as a soluble protein. The term also encompasses naturally occurring variants of PD-L1, e.g., splice variants or allelic variants. The basic structure of PD-L1 comprises 4 domains: extracellular Ig-like V-type and Ig-like C2-type domains, a transmembrane domain, and a cytoplasmic domain. Additional information on the human PD-L1 gene, including the genomic DNA sequence, can be found under NCBI Gene ID No. 29126. Additional information on the mouse PD-L1 gene, including the genomic DNA sequence, can be found under NCBI Gene ID No. 60533. The amino acid sequence of an exemplary full-length human PD-L1 protein is shown in SEQ ID NO: 18. The amino acid sequence of an exemplary full-length human PD-L1 protein can be found, e.g., under NCBI Accession No. NP_001254653 or UniProt Accession No. Q9NZQ7, while the exemplary full-length mouse PD-L1 protein sequence can be found, e.g., under NCBI Accession No. NP_068693 or Uniprot Accession No. Q9EP73.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, and/or target cell killing). As used herein, a PD-1 axis binding antagonist includes a PD-1 binding antagonist, a PD-L1 binding antagonist, and a PD-L2 binding antagonist.

As used herein, a "PD-L1 binding antagonist" is a molecule that decreases, blocks, inhibits, abrogates or interferes with signal transduction resulting from the interaction of PD-L1 with either one or more of its binding partners, such as PD-1 and/or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, PD-L1 binding antagonists include anti-PD-L1 antibodies and antigen-binding fragments thereof, immunoadhesins, fusion proteins, oligopeptides, small molecule antagonist, polynucleotide antagonists, and other molecules that decrease, block, inhibit, abrogate or interfere with signal transduction resulting from the interaction of PD-L1 with one or more of its binding partners, such as PD-1 and/or B7-1. In one embodiment, a PD-L1 binding antagonist reduces the negative signal mediated by or through cell surface proteins expressed on T lymphocytes, and other cells, mediated signaling through PD-L1 or PD-1 so as render a dysfunctional T-cell less dysfunctional. In some embodiments, a PD-L1 binding antagonist is an anti-PD-L1 antibody. In a specific aspect, an anti-PD-L1 antibody is YW243.55.S70. In another specific aspect, an anti-PD-L1 antibody is MDX-1105. In still another specific aspect, an anti-PD-L1 antibody is MPDL3280A (atezolizumab). In still another specific aspect, an anti-PD-L1 antibody is MEDI4736 (durvalumab). In still another specific aspect, an anti-PD-L1 antibody is MSB0010718C (avelumab). MDX-1105, also known as BMS-936559, is an anti-PD-L1 antibody described in WO2007/005874. Antibody YW243.55.S70 is an anti-PD- L1 antibody described in WO 2010/077634 and U.S. Pat. No. 8,217,149, the entirety of each of which is incorporated herein by reference.

As used herein, a "PD-1 binding antagonist" is a molecule that decreases, blocks, inhibits, abrogates or interferes with signal transduction resulting from the interaction of PD-1 with one or more of its binding partners, such as PD-L1 and/or PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies and antigen-binding fragments thereof, immunoadhesins, fusion proteins, oligopeptides, small molecule antagonist, polynucleotide antagonists, and other molecules that decrease, block, inhibit, abrogate or interfere with signal transduction resulting from the interaction of PD-1 with PD-L1 and/or PD-L2. In one embodiment, a PD-1 binding antagonist reduces the negative signal mediated by or through cell surface proteins expressed on T lymphocytes, and other cells, mediated signaling through PD-1 or PD-L1 so as render a dysfunctional T-cell less dysfunctional. In some embodiments, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is CT-011 (pidilizumab). In another specific aspect, a PD-1 binding antagonist is MEDI-0680 (AMP-514). In another specific aspect, a PD-1 binding antagonist is PDR001. In another specific aspect, a PD-1 binding antagonist is REGN2810. In another specific aspect, a PD-1 binding antagonist is BGB-108. In another specific aspect, a PD-1 binding antagonist is AMP-224. MDX-1106, also known as MDX-1106-04, ONO-4538, BMS-936558, or nivolumab, is an anti-PD-1 antibody described in WO2006/121168. AMP-224, also known as B7-DCIg, is a PD-L2-Fc fusion soluble receptor described in WO2010/027827 and WO2011/066342.

A "reference sample," "reference cell," "reference tissue," "control sample," "control cell," or "control tissue," as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, the reference sample, reference cell, reference tissue, control sample, control cell, or control tissue may be healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

"Individual response" or "response" can be assessed using any endpoint indicating a benefit to the individual, including, without limitation, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival and progression free survival; and/or (9) decreased mortality at a given point of time following treatment.

An "effective response" of a patient or a patient's "responsiveness" to treatment with a medicament and similar wording refers to the clinical or therapeutic benefit imparted to a patient at risk for, or suffering from, a disease or disorder, such as cancer. In one embodiment, such benefit includes any one or more of: extending survival (including overall survival and progression-free survival); resulting in an objective response (including a complete response or a partial response); or improving signs or symptoms of cancer. In one embodiment, the biomarker (e.g., PD-L1 expression, for example, as determined using IHC) is used to identify the patient who is predicted to have an increased likelihood of being responsive to treatment with a medicament (e.g., treatment comprising an anti-cancer therapy), relative to a patient who does not express the biomarker. In one embodiment, the biomarker (e.g., PD-L1 expression, for example, as determined using IHC) is used to identify the patient who is predicted to have an increase likelihood of being responsive to treatment with a medicament (e.g., an anti-cancer therapy), relative to a patient who does not express the biomarker at the same level. In one embodiment, the presence of the biomarker is used to identify a patient who is more likely to respond to treatment with a medicament, relative to a patient that does not have the presence of the biomarker. In another embodiment, the presence of the biomarker is used to determine that a patient will have an increased likelihood of benefit from treatment with a medicament, relative to a patient that does not have the presence of the biomarker.

An "objective response" refers to a measurable response, including complete response (CR) or partial response (PR). In some embodiments, the "objective response rate (ORR)" refers to the sum of complete response (CR) rate and partial response (PR) rate.

By "complete response" or "CR" is intended the disappearance of all signs of cancer (e.g., disappearance of all target lesions) in response to treatment. This does not always mean the cancer has been cured.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration, or longer.

As used herein, "reducing or inhibiting cancer relapse" means to reduce or inhibit tumor or cancer relapse or tumor or cancer progression. As disclosed herein, cancer relapse and/or cancer progression include, without limitation, cancer metastasis.

As used herein, "partial response" or "PR" refers to a decrease in the size of one or more tumors or lesions, or in the extent of cancer in the body, in response to treatment. For example, in some embodiments, PR refers to at least a 30% decrease in the sum of the longest diameters (SLD) of target lesions, taking as reference the baseline SLD.

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

The term "survival" refers to the patient remaining alive, and includes overall survival as well as progression-free survival As used herein, "progression-free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall survival" (OS) refers to the percentage of individuals in a group who are likely to be alive after a particular duration of time.

By "extending survival" is meant increasing overall or progression-free survival in a treated patient relative to an untreated patient (i.e. relative to a patient not treated with the medicament), or relative to a patient who does not express a biomarker at the designated level, and/or relative to a patient treated with an approved anti-tumor agent.

For the purposes herein a "section" of a tissue sample is meant a single part or piece of a tissue sample, for example, a thin slice of tissue or cells cut from a tissue sample (e.g., a tumor sample). It is to be understood that multiple sections of tissue samples may be taken and subjected to analysis, provided that it is understood that the same section of tissue sample may be analyzed at both morphological and molecular levels, or analyzed with respect to polypeptides (e.g., by immunohistochemistry) and/or polynucleotides (e.g., by in situ hybridization).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope, e.g., amino acid residues 279-290 of human PD-L1 (SEQ ID NO: 1)) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of $\leq 1$ μM, $\leq 100$ nM, $\leq 10$ nM, $\leq 1$ nM, or $\leq 0.1$ nM. In certain embodiments, an antibody specifically binds to an epitope on a protein that is conserved among the protein from different species. In another embodiment, specific binding can include, but does not require exclusive binding.

A "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "substantially the same," as used herein, denotes a sufficiently high degree of similarity between two numeric values, such that one of skill in the art would consider the difference between the two values to be of little or no biological and/or statistical significance within the context of the biological characteristic measured by said values (e.g., Kd values or expression levels). The difference between said two values is, for example, less than about 50%, less than about 40%, less than about 30%, less than about 20%, and/or less than about 10%, as a function of the reference/comparator value.

The phrase "substantially different," as used herein, denotes a sufficiently high degree of difference between two numeric values such that one of skill in the art would consider the difference between the two values to be of statistical significance within the context of the biological characteristic measured by said values (e.g., Kd values or expression levels). The difference between said two values is, for example, greater than about 10%, greater than about 20%, greater than about 30%, greater than about 40%, and/or greater than about 50%, as a function of the value for the reference/comparator molecule.

A "T-cell dysfunctional disorder" is a disorder or condition of T-cells characterized by increased or decreased responsiveness to antigenic stimulation. In a particular embodiment, a T-cell dysfunctional disorder is a disorder that is specifically associated with inappropriate increased signaling through PD-1/PD-L1 and/or PD-L1/B7.1. In another embodiment, a T-cell dysfunctional disorder is one in which T-cells are anergic or have decreased ability to secrete cytokines, proliferate, or execute cytolytic activity. In another embodiment, a T cell dysfunction is one in which T cell exhaustion arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.). In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies (e.g., anti-PD-1 antibodies and/or anti-PD-L1 antibodies) are used to delay development of a disease or to slow the progression of a disease.

The term "tumor," as used herein, refers to all neoplastic cell growth and proliferation, whether malignant or benign, and all pre-cancerous and cancerous cells and tissues. The terms "cancer," "cancerous," and "tumor" are not mutually exclusive as referred to herein.

A "tumor-infiltrating immune cell," as used herein, refers to any immune cell present in a tumor or a sample thereof. Tumor-infiltrating immune cells include, but are not limited to, intratumoral immune cells, peritumoral immune cells, other tumor stroma cells (e.g., fibroblasts), or any combination thereof. Such tumor-infiltrating immune cells can be, for example, T lymphocytes (such as CD8+ T lymphocytes and/or CD4+ T lymphocytes), B lymphocytes, or other bone marrow-lineage cells, including granulocytes (e.g., neutrophils, eosinophils, and basophils), monocytes, macrophages, dendritic cells (e.g., interdigitating dendritic cells), histiocytes, and natural killer cells.

A "tumor cell" as used herein, refers to any tumor cell present in a tumor or a sample thereof. Tumor cells may be distinguished from other cells that may be present in a tumor sample, for example, stromal cells and tumor-infiltrating immune cells, using methods known in the art and/or described herein.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), response rates (e.g., CR and PR), duration of response, and/or quality of life.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al. *Kuby Immunology.* 6th ed., page 91, W.H. Freeman and Co., 2007. A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al. *J. Immunol.* 150: 880-887, 1993 and Clarkson et al. *Nature.* 352: 624-628, 1991.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "growth inhibitory agent" when used herein refers to a compound or composition which inhibits growth and/or proliferation of a cell (e.g., a cell whose growth is dependent on PD-L1 expression) either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as the anthracycline antibiotic doxorubicin ((8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione), epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in "*The Molecular Basis of Cancer,*" Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, the terms "patient" or "subject" are used interchangeably and refer to any single animal, more preferably a mammal (including such non-human animals as, for example, dogs, cats, horses, rabbits, zoo animals, cows, pigs, sheep, and non-human primates) for which treatment is desired. In particular embodiments, the patient herein is a human.

As used herein, "administering" is meant a method of giving a dosage of a compound (e.g., an anti-cancer therapeutic agent) or a pharmaceutical composition (e.g., a pharmaceutical composition including an anti-cancer therapeutic agent) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

II. Compositions and Methods

The invention provides novel antibodies that bind to PD-L1. Antibodies of the invention are useful, for example, for detecting the presence of PD-L1 or the expression level of PD-L1 (e.g., in biological samples, including tumor samples).

A. Exemplary Anti-PD-L1 Antibodies

The invention provides anti-PD-L1 antibodies useful for, e.g., diagnostic applications (e.g., immunohistochemistry (IHC), immunofluorescence (IF), and immunoblot (e.g., Western blot)). In one example, the invention provides anti-PD-L1 antibodies that bind to an epitope including amino acid residues 279-290 of PD-L1 (e.g., amino acid residues 279-290 of human PD-L1 SKKQSDTHLEET (SEQ ID NO: 1)), which is part of the N-terminal cytoplasmic region of human PD-L1. The epitope on PD-L1 may be recognized in a manner that is conformation-dependent or conformation-independent.

In some instances, the anti-PD-L1 antibodies that bind to amino acid residues 279-290 of PD-L1 include at least one, two, three, four, five, or six HVRs selected from (a) HVR-H1 comprising the amino acid sequence of SEQ ID NO: 2; (b) HVR-H2 comprising the amino acid sequence of SEQ ID NO: 3; (c) HVR-H3 comprising the amino acid sequence of SEQ ID NO: 4; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11. For example, in some instances, the anti-PD-L1 antibodies include (a) an HVR-H1 comprising the amino acid sequence of SEQ ID NO: 2; (b) an HVR-H2 comprising the amino acid sequence of SEQ ID NO: 3; and (c) an HVR-H3 comprising the amino acid sequence of SEQ ID NO: 4. In some instances, the anti-PD-L1 antibodies include (a) an HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In some instances wherein the anti-PD-L1 antibodies bind to amino acid residues 279-290 of PD-L1 and include (a) an HVR-H1 comprising the amino acid sequence of SEQ ID NO: 2; (b) an HVR-H2 comprising the amino acid sequence of SEQ ID NO: 3; and (c) an HVR-H3 comprising the amino acid sequence of SEQ ID NO: 4, the anti-PD-L1 antibodies further include the following heavy chain variable domain framework regions (FRs): (a) FR-H1 comprising the amino acid sequence of QSLEESGGRLVKPDE-TLTITCTVSGIDLS (SEQ ID NO: 5); (b) FR-H2 comprising the amino acid sequence of WVRQAPGEGLEWIG (SEQ ID NO: 6); (c) FR-H3 comprising the amino acid sequence of RLTISKPSSTKVDLKITSPTTEDTATYFCGR (SEQ ID NO: 7); or (d) FR-H4 comprising the amino acid sequence of WGPGTLVTVSS (SEQ ID NO: 8). In some instances wherein the anti-PD-L1 antibodies bind to amino acid residues 279-290 of PD-L1 and include (a) an HVR-H1 comprising the amino acid sequence of SEQ ID NO: 2; (b) an HVR-H2 comprising the amino acid sequence of SEQ ID NO: 3; and (c) an HVR-H3 comprising the amino acid sequence of SEQ ID NO: 4, the anti-PD-L1 antibodies further include the following heavy chain variable domain framework regions (FRs): (a) FR-H1 comprising the amino acid sequence of QSLEESGGRLVKPDE-TLTITCTVSGIDLS (SEQ ID NO: 5); (b) FR-H2 comprising the amino acid sequence of WVRQAPGEGLEWIG (SEQ ID NO: 6); (c) FR-H3 comprising the amino acid sequence of RLTISKPSSTKVDLKITSPTTEDTATYFCGR (SEQ ID NO: 7); and (d) FR-H4 comprising the amino acid sequence of WGPGTLVTVSS (SEQ ID NO: 8).

In some instances wherein the anti-PD-L1 antibodies bind to amino acid residues 279-290 of PD-L1, the antibodies include (a) an HVR-H1 comprising the amino acid sequence of SEQ ID NO: 2; (b) an HVR-H2 comprising the amino acid sequence of SEQ ID NO: 3; (c) an HVR-H3 comprising the amino acid sequence of SEQ ID NO: 4; (d) an HVR-L1 comprising the amino acid sequence of QASESVYSN-NYLS (SEQ ID NO: 9); (e) an HVR-L2 comprising the amino acid sequence of LASTLAS (SEQ ID NO: 10); and (f) an HVR-L3 comprising the amino acid sequence of IGGKSSSTDGNA (SEQ ID NO: 11). In some instances, these anti-PD-L1 antibodies include the following FRs: (a) FR-H1 comprising the amino acid sequence of QSLEESG-GRLVKPDETLTITCTVSGIDLS (SEQ ID NO: 5); (b) FR-H2 comprising the amino acid sequence of WVRQAPGEGLEWIG (SEQ ID NO: 6); (c) FR-H3 comprising the amino acid sequence of RLTISKPSSTKVDLKITSPTTEDTATYFCGR (SEQ ID NO: 7); and (d) FR-H4 comprising the amino acid sequence of WGPGTLVTVSS (SEQ ID NO: 8) and may additionally or alternatively include (e) FR-L1 comprising the amino acid sequence of AIVMTQTPSPVSAAVGGTVTINC (SEQ ID NO: 12); (f) FR-L2 comprising the amino acid sequence of WFQQKPGQPPKLLIY (SEQ ID NO: 13); (g) FR-L3 comprising the amino acid sequence of GVPSRFKGSGSGTQFTLTISGVQCDDAATYYC (SEQ ID NO: 14); and (h) FR-L4 comprising the amino acid sequence of FGGGTEVVVR (SEQ ID NO: 15).

In some instances, the anti-PD-L1 antibodies that bind to amino acid residues 279-290 of PD-L1 may also include a heavy chain variable domain (VH) sequence having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 16. In certain embodiments, a VH sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 16), but an anti-PD-L1 antibody including that sequence retains the ability to bind to PD-L1. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 16. In certain embodiments, substitutions, insertions, or deletions occur in regions outside the HVRs (i.e., in the FRs). Optionally, the anti-PD-L1 antibodies include the VH sequence in SEQ ID NO: 16, including post-translational modifications of that sequence. In a particular embodiment, the VH comprises one, two, or three HVRs selected from: (a) HVR-H1 comprising the amino acid sequence of SEQ ID NO: 2, (b) HVR-H2 comprising the amino acid sequence of SEQ ID NO: 3, and (c) HVR-H3 comprising the amino acid sequence of SEQ ID NO: 4.

In some instances, the anti-PD-L1 antibodies that bind to amino acid residues 279-290 of PD-L1 may also include a light chain variable domain (VL) having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequence of, the amino acid sequence of SEQ ID NO: 17. In certain embodiments, a VL sequence having at least 80%, 81%, 82%, 83%, 84%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence (SEQ ID NO: 17), but an anti-PD-L1 antibody including that sequence retains the ability to bind to PD-L1. In certain embodiments, a total of 1 to 10 amino acids (e.g., 1, 2, 3, 4, 5, 6, 7, 8, 9, or 10 amino acids) have been substituted, inserted, and/or deleted in SEQ ID NO: 17. In certain embodiments, the substitutions, insertions, or deletions occur in regions outside the HVRs (i.e., in the FRs). Optionally, the anti-PD-L1 antibody comprises the VL sequence in SEQ ID NO: 17, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In some instances, the anti-PD-L1 antibodies that bind to amino acid residues 279-290 of PD-L1 include both VH and VL sequences having at least 80% (e.g., at least 81%, 82%, 83%, 84%, 85%, 86%, 87%, 88%, or 89%), at least 90% (e.g., at least 91%, 92%, 93%, or 94%), or at least 95% (e.g., at least 96%, 97%, 98%, or 99%) sequence identity to, or the sequences of, the amino acid sequences of SEQ ID NOs: 16 and 17, respectively, and may or may not include post-translational modifications of those sequences.

In other instances, the invention provides antibodies that specifically bind PD-L1, wherein the antibodies include (a) an HVR-H1 comprising the amino acid sequence of SEQ ID NO: 2; (b) an HVR-H2 comprising the amino acid sequence of SEQ ID NO: 3; (c) an HVR-H3 comprising the amino acid sequence of SEQ ID NO: 4; (d) an HVR-L1 comprising the amino acid sequence of QASESVYSNNYLS (SEQ ID NO: 9); (e) an HVR-L2 comprising the amino acid sequence of LASTLAS (SEQ ID NO: 10); and (f) an HVR-L3 comprising the amino acid sequence of IGGKSSSTDGNA (SEQ ID NO: 11). In some instances, these anti-PD-L1 antibodies include the following FRs: (a) FR-H1 comprising the amino acid sequence of QSLEESGGRLVKPDE-TLTITCTVSGIDLS (SEQ ID NO: 5); (b) FR-H2 comprising the amino acid sequence of WVRQAPGEGLEWIG (SEQ ID NO: 6); (c) FR-H3 comprising the amino acid sequence of RLTISKPSSTKVDLKITSPTTEDTATYFCGR (SEQ ID NO: 7); and (d) FR-H4 comprising the amino acid sequence of WGPGTLVTVSS (SEQ ID NO: 8) and may additionally or alternatively include (e) FR-L1 comprising the amino acid sequence of AIVMTQTPSPVSAAVGGTVTINC (SEQ ID NO: 12); (f) FR-L2 comprising the amino acid sequence of WFQQKPGQPPKLLIY (SEQ ID NO: 13); (g) FR-L3 comprising the amino acid sequence of GVPSRFKGSGSGTQFTLTISGVQCDDAATYYC (SEQ ID NO: 14); and (h) FR-L4 comprising the amino acid sequence of FGGGTEVVVR (SEQ ID NO: 15). In some embodiments, for example, the anti-PD-L1 antibodies include both a VH and a VL sequence including the sequences of the amino acid sequences of SEQ ID NOs: 16 and 17, respectively, and may or may not include post-translational modifications.

For example, the invention features anti-PD-L1 antibodies, such as the anti-PD-L1 antibody SP142, with the following heavy and light chain variable region sequences.

The amino acid sequence of the heavy chain variable region of SP142 is the following:

```
                                    (SEQ ID NO: 16)
QSLEESGGRLVKPDETLTITCTVSGIDLSSNGLTWV
                            HVR-H1

RQAPGEGLEWIGTINKDASAYYASWAKGRLTISKP
              HVR-H2

SSTKVDLKITSPTTEDTATYFCGRIAFKTGTSIW
                          HVR-H3

GPGTLVTVSS.

The amino acid sequence of the light
chain variable region of SP142 is the
following:
                                    (SEQ ID NO: 17)
AIVMTQTPSPVSAAVGGTVTINCQASESVYSNNYLSWF
                        HVR-L1

QQKPGQPPKLLIYLASTLASGVPSRFKGSGSGTQFTLT
             HVR-L2

ISGVQCDDAATYYCIGGKSSSTDGNAFGGGTEVVVR.
              HVR-L3
```

In some instances, anti-PD-L1 antibodies of the invention are antibodies that compete for binding to PD-L1 with any one or more of the anti-PD-L1 antibodies described above. In some instances, anti-PD-L1 antibodies of the invention are antibodies that bind to the same epitope or substantially the same epitope as any one or more of the anti-PD-L1 antibodies described above.

In some instances, an anti-PD-L1 antibody according to any of the above embodiments may be a monoclonal antibody, comprising a chimeric, humanized, or human antibody. In one embodiment, an anti-PD-L1 antibody is an antibody fragment, for example, a Fv, Fab, Fab', scFv, diabody, or F(ab')$_2$ fragment. In another embodiment, the antibody is a full-length antibody, e.g., an intact IgG antibody (e.g., an intact IgG1 antibody) or other antibody class or isotype as defined herein.

It should be understood that the anti-PD-L1 antibodies of the invention, although useful for the detection of the presence or the expression level of PD-L1 in a biological sample as exemplified by the Examples below, may also be used or adapted for therapeutic use.

In further aspects, the anti-PD-L1 antibodies according to any of the above embodiments may incorporate any of the features, singly or in combination, as described in Sections 1-5 below.

1. Antibody Affinity

In certain embodiments, an antibody provided herein has a dissociation constant (Kd) of $\le 1$ µM, $\le 100$ nM, $\le 10$ nM, $\le 1$ nM, $\le 0.1$ nM, $\le 0.01$ nM, or $\le 0.001$ nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293: 865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57: 4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20™) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$)

are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al. *J. Mol. Biol.* 293: 865-881, 1999. If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9: 129-134, 2003. For a review of scFv fragments, see, e.g., Pluckthun. *The Pharmacology of Monoclonal Antibodies.* Vol. 113, pp. 269-315, Rosenburg and Moore eds. Springer-Verlag, New York, 1994; see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134, 2003; and Hollinger et al. *Proc. Natl. Acad. Sci. USA.* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Nat. Acad. Sci. USA.* 81: 6851-6855, 1984. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro et al. *Front. Biosci.* 13: 1619-1633, 2008, and are further described, e.g., in Riechmann et al. *Nature.* 332: 323-329, 1988; Queen et al. *Proc. Natl. Acad. Sci. USA.* 86: 10029-10033, 1989; U.S. Pat. Nos. 5,821,337, 7,527,791, 6,982,321, and 7,087,409; Kashmiri et al. *Methods.* 36: 25-34, 2005 (describing SDR (a-CDR) grafting); Padlan. *Mol. Immunol.* 28: 489-498, 1991 (describing "resurfacing"); DaU'Acqua et al. *Methods.* 36: 43-60, 2005 (describing "FR shuffling"); and Osbourn et al. *Methods* 36: 61-68, 2005 and Klimka et al. *Br. J. Cancer.* 83: 252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151: 2296, 1993); framework regions derived from the consensus sequence of human antibodies of a particular subgroup of light or heavy chain variable regions (see, e.g., Carter et al. *Proc. Nat. Acad. Sci. USA.* 89: 4285, 1992; and Presta et al. *J. Immunol.* 151: 2623, 1993); human mature (somatically mutated) framework regions or human germline framework regions (see, e.g., Almagro et al. *Front. Biosci.* 13: 1619-1633, 2008); and framework regions derived from screening FR libraries (see, e.g., Baca et al. *J. Biol. Chem.* 272:10678-10684, 1997 and Rosok et al. *J. Biol. Chem.* 271: 22611-22618, 1996).

4. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for PD-L1 and the other is for any other antigen. In certain embodiments, bispecific antibodies may bind to two different epitopes of PD-L1. Bispecific antibodies may also be used to localize cytotoxic agents to cells which express PD-L1. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein et al. *Nature.* 305: 537, 1983, WO 93/08829, and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. *Science.* 229: 81, 1985); using leucine zippers to produce bi-specific antibodies (see, e.g., Kostelny et al. *J. Immunol.* 148(5): 1547-1553, 1992); using "diabody" technology for making bispecific antibody fragments (see, e.g., Hollinger et al. *Proc. Natl. Acad. Sci. USA.,* 90: 6444-6448, 1993); and using single-chain Fv (sFv) dimers (see, e.g. Gruber et al. *J. Immunol.* 152: 5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to PD-L1 as well as another, different antigen (see, e.g., US 2008/0069820).

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |

TABLE 1-continued

| Exemplary and Preferred Amino Acid Substitutions | | |
| --- | --- | --- |
| Original Residue | Exemplary Substitutions | Preferred Substitutions |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, lie;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury. *Methods Mol. Biol.* 207: 179-196, 2008), and/or SDRs (a-CDRs), with the resulting variant VH or VL being tested for binding affinity. Affinity maturation by constructing and reselecting from secondary libraries has been described, e.g., in Hoogenboom et al. *Methods in Molecular Biology.* 178:1-37, O'Brien et al. eds., Human Press, Totowa, NJ, 2001. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science.* 244: 1081-1085, 1989. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH.* 15: 26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249, 2004; and Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem. Biophys.* 249: 533-545, 1986; US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an anti-PD-L1 antibody of the invention (e.g., SP142) provided herein, thereby generating an Fc region variant. The Fc region variant may comprise a human Fc region sequence (e.g., a human IgG$_1$, IgG$_2$, IgG$_3$ or IgG$_4$ Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch et al. *Annu. Rev. Immunol.* 9: 457-492, 1991. Non-limiting examples of in vitro assays to assess ADCC activity of a molecule of interest is described in U.S. Pat. Nos. 5,500,362 and 5,821,337; Hellstrom et al. *Proc. Natl. Acad. Sci. USA.* 83: 7059-7063, 1986; Hellstrom et al. *Proc. Natl Acad. Sci. USA.* 82:1499-1502, 1985; and Bruggemann et al. *J. Exp. Med.* 166: 1351-1361, 1987. Alternatively, non-radioactive assays methods may be employed (see, for example, ACTI™ non-radioactive cytotoxicity assay for flow cytometry (CellTechnology, Inc. Mountain View, CA; and Cyto-Tox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Natl. Acad. Sci. USA.* 95:652-656, 1998. C1q binding assays may also be carried out to confirm that the antibody is unable to bind C1 q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods.* 202:163, 1996; Cragg et al. *Blood.* 101: 1045-1052, 2003; and Cragg et al. *Blood* 103: 2738-2743, 2004. FcRn binding and in vivo clearance/half life determinations can also be performed using methods known in the art (see, e.g., Petkova et al. *Intl. Immunol.* 18(12): 1759-1769, 2006).

Antibodies with reduced effector function include those with substitution of one or more of Fc region residues 238, 265, 269, 270, 297, 327, and 329 (U.S. Pat. No. 6,737,056). Such Fc mutants include Fc mutants with substitutions at two or more of amino acid positions 265, 269, 270, 297, and 327, including the so-called "DANA" Fc mutant with substitution of residues 265 and 297 to alanine (U.S. Pat. No. 7,332,581).

Certain antibody variants with improved or diminished binding to FcRs are described. See, e.g., U.S. Pat. No. 6,737,056; WO 2004/056312; and Shields et al. *J. Biol. Chem.* 9(2): 6591-6604, 2001.

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184, 2000.

Antibodies with increased half lives and improved binding to the neonatal Fc receptor (FcRn), which is responsible for the transfer of maternal IgGs to the fetus (Guyer et al. *J. Immunol.* 117: 587,1976 and Kim et al, *J. Immunol.* 24: 249, 1994), are described in US Patent Application No. 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424, or 434, e.g., substitution of Fc region residue 434 (U.S. Pat. No. 7,371,826). See also Duncan et al. *Nature.* 322:738-740, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an anti-PD-L1 antibody of the invention (e.g., SP142) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA.* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-PD-L1 antibody described herein (e.g., SP142) is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-PD-L1 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-PD-L1 antibody (e.g., SP142), nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton. *Methods in Molecular Biology. Vol.* 248, pp. 245-254, B. K. C. Lo, ed., Humana Press, Totowa, NJ, 2003, describing expression of antibody fragments in *E. coli.* After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross. *Nat. Biotech.* 22: 1409-1414, 2004 and Li et al. *Nat. Biotech.* 24: 210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59, 1977); baby hamster kidney cells (BHK); mouse Sertoli cells (TM4 cells as described, e.g., in Mather. *Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3 A); human lung cells (W138); human liver cells (Hep G2); mouse mammary tumor (MMT 060562); TRI cells, as described, e.g., in Mather et al. *Annals N.Y. Acad.*

*Sci.* 383:44-68, 1982; MRC 5 cells; and FS4 cells. Other useful mammalian host cell lines include Chinese hamster ovary (CHO) cells, including DHFR" CHO cells (Urlaub et al. *Proc. Natl. Acad. Sci. USA.* 77: 4216, 1980); and myeloma cell lines such as Y0, NS0 and Sp2/0. For a review of certain mammalian host cell lines suitable for antibody production, see, e.g., Yazaki et al. *Methods in Molecular Biology. Vol.* 248, pp. 255-268, B. K. C. Lo, ed., Humana Press, Totowa, NJ, 2003.

C. Assays

Anti-PD-L1 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, for example, by known methods such as Enzyme-Linked Immunosorbant Assay (ELISA), immunoblotting (e.g., Western blotting), flow cytometry (e.g., FACS™), immunohistochemistry, immunofluorescence, etc.

In another aspect, competition assays may be used to identify an antibody that competes with any one of the antibodies of the invention for binding to PD-L1 (e.g., anti-PD-L1 antibody SP142). In certain embodiments, such a competing antibody binds to the same epitope (e.g., a linear or a conformational epitope) that is bound by any one of the antibodies of the invention (e.g., anti-PD-L1 antibody SP142). Detailed exemplary methods for mapping an epitope to which an antibody binds are provided in Morris "Epitope Mapping Protocols," in *Methods in Molecular Biology* Vol. 66 (Humana Press, Totowa, NJ, 1996).

In an exemplary competition assay, immobilized PD-L1 is incubated in a solution comprising a first labeled antibody that binds to PD-L1 (e.g., anti-PD-L1 antibody SP142) and a second unlabeled antibody that is being tested for its ability to compete with the first antibody for binding to PD-L1. The second antibody may be present in a hybridoma supernatant. As a control, immobilized PD-L1 is incubated in a solution comprising the first labeled antibody but not the second unlabeled antibody. After incubation under conditions permissive for binding of the first antibody to PD-L1, excess unbound antibody is removed, and the amount of label associated with immobilized PD-L1 is measured. If the amount of label associated with immobilized PD-L1 is substantially reduced in the test sample relative to the control sample, then that indicates that the second antibody is competing with the first antibody for binding to PD-L1. See, e.g., Harlow et al. *Antibodies: A Laboratory Manual.* Ch.14 (Cold Spring Harbor Laboratory, Cold Spring Harbor, NY, 1988).

2. Detection Assays

In one aspect, assays are provided for identifying anti-PD-L1 antibodies useful for detecting the presence of PD-L1, e.g., in immunohistochemistry (IHC), immunofluorescence (IF), immunoblotting (e.g., Western blotting), flow cytometry (e.g., FACS™), or Enzyme-Linked Immunosorbant Assay (ELISA) assays. In certain embodiments, an antibody of the invention is tested for such activity.

D. Immunoconjugates

The invention also provides immunoconjugates comprising an anti-PD-L1 antibody herein conjugated to one or more labels and/or agents, such as radioactive isotopes.

In one embodiment, an immunoconjugate comprises an antibody as described herein conjugated to a radioactive atom to form a radioconjugate. A variety of radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an anti-PD-L1 antibody and label or agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the label or agent. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

E. Methods and Compositions for Diagnostics and Detection

In certain embodiments, the anti-PD-L1 antibodies provided herein (e.g., SP142 or any other anti-PD-L1 antibody described, for example, above in Section A, "Exemplary Anti-PD-L1 Antibodies") are useful for detecting the presence of PD-L1 in a biological sample. The term "detecting" as used herein encompasses quantitative or qualitative detection.

In one instance, an anti-PD-L1 antibody (e.g., SP142) for use in a method of diagnosis or detection is provided. In another instance, the invention provides for the use of an anti-PD-L1 antibody (e.g., SP142) in the manufacture of a reagent for use in a method of diagnosis or detection. In one instance, for example, a method of detecting the presence of PD-L1 in a biological sample, described below, is provided. In certain embodiments, the method comprises contacting the biological sample with an anti-PD-L1 antibody as described herein under conditions permissive for binding of the anti-PD-L1 antibody to PD-L1, and detecting whether a complex is formed between the anti-PD-L1 antibody and PD-L1. Such method may be an in vitro or in vivo method. Anti-PD-L1 antibodies of the invention (e.g., SP142) can be used, for example, in immunoassays, including, for example, immunohistochemistry (IHC), immunofluorescence (IF), immunoblotting (e.g., Western blotting), flow cytometry (e.g., FACS™), and Enzyme-linked Immunosorbant Assay (ELISA). In one embodiment, an anti-PD-L1 antibody is used to select subjects eligible for therapy with an anti-PD-L1 antibody, for example, where PD-L1 is a biomarker for selection of patients. The invention further provides for the use of an anti-PD-L1 antibody in a method of diagnosing a subject suffering from a disorder (e.g., a cancer or an immune dysfunction), the method comprising: determining the presence or expression level of PD-L1 in a sample obtained from the subject by contacting the sample with an anti-PD-L1 antibody of the invention (e.g., SP142) and detecting the presence of the bound antibody.

For example, the method provides for the use of an anti-PD-L1 antibody in a method of diagnosing a subject suffering from a cancer, the method comprising: determining the presence or expression level of PD-L1 in a sample obtained from the subject by contacting the sample with an anti-PD-L1 antibody of the invention (e.g., SP142) and detecting the presence of the bound antibody. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof.

The invention yet further provides for the use of an anti-PD-L1 antibody in the manufacture of a reagent for use in a method of diagnosing a subject suffering from a disorder (e.g., a cancer or an immune dysfunction), the method comprising: determining the presence or expression level of PD-L1 in a sample obtained from the subject by contacting the sample with an anti-PD-L1 antibody of the invention (e.g., SP142) and detecting the presence of the bound antibody.

For example, the method provides for the use of an anti-PD-L1 antibody in the manufacture of a reagent for use in a method of diagnosing a subject suffering from a cancer, the method comprising: determining the presence or expression level of PD-L1 in a sample obtained from the subject by contacting the sample with an anti-PD-L1 antibody of the invention (e.g., SP142) and detecting the presence of the bound antibody. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof.

In another instance, the invention provides a method for identifying a subject suffering from a disorder (e.g., cancer or an immune dysfunction) who is likely to respond to a treatment, the method including: determining the presence or expression level of PD-L1 in a sample obtained from the subject by contacting the sample with an anti-PD-L1 antibody of the invention (e.g., SP142) and detecting the presence of the bound antibody, wherein the presence or expression level of PD-L1 in the sample indicates that the subject is likely to respond to the treatment.

For example, the invention provides a method for identifying a subject suffering from a cancer who is likely to respond to treatment with an anti-cancer therapy, the method comprising: determining the presence or expression level of PD-L1 in a sample obtained from the subject by contacting the sample with an anti-PD-L1 antibody of the invention (e.g., SP142) and detecting the presence of the bound antibody, wherein the presence or expression level of PD-L1 in the sample indicates that the subject is likely to respond to treatment with the anti-cancer therapy. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof.

In yet another instance, the invention provides a method for predicting responsiveness of an individual suffering from a disorder (e.g., cancer or an immune dysfunction) to a treatment, the method including: determining the presence or expression level of PD-L1 in a sample obtained from the subject by contacting the sample with an anti-PD-L1 antibody of the invention (e.g., SP142) and detecting the presence of the bound antibody, wherein the presence or expression level of PD-L1 in the sample indicates that the subject is more likely to respond to the treatment.

For example, the invention provides a method for predicting responsiveness of an individual suffering from a cancer to treatment with an anti-cancer therapy, the method comprising: determining the presence or expression level of PD-L1 in a sample obtained from the subject by contacting the sample with an anti-PD-L1 antibody of the invention (e.g., SP142) and detecting the presence of the bound antibody, wherein the presence or expression level of PD-L1 in the sample indicates that the subject is more likely to respond to treatment with the anti-cancer therapy. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof.

In a still further instance, the invention provides a method for determining the likelihood that a subject suffering from a disorder (e.g., cancer or an immune dysfunction) will exhibit benefit from a treatment, the method including: determining the presence or expression level of PD-L1 in a sample obtained from the subject by contacting the sample with an anti-PD-L1 antibody of the invention (e.g., SP142) and detecting the presence of the bound antibody, wherein the presence or expression level of PD-L1 in the sample indicates the likelihood that the subject will exhibit benefit from treatment with the treatment.

For example, the invention provides a method for determining the likelihood that a subject suffering from a cancer will exhibit benefit from treatment with an anti-cancer therapy, the method including: determining the presence or expression level of PD-L1 in a sample obtained from the subject by contacting the sample with an anti-PD-L1 antibody of the invention (e.g., SP142) and detecting the presence of the bound antibody, wherein the presence or expression level of PD-L1 in the sample indicates the likelihood that the subject will exhibit benefit from treatment with the anti-cancer therapy. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof.

In another instance, the invention provides a method for selecting a therapy for a subject suffering from a disorder (e.g., cancer or an immune dysfunction), the method including: determining the presence or expression level of PD-L1 in a sample obtained from the subject by contacting the sample with an anti-PD-L1 antibody of the invention (e.g., SP142) and detecting the presence of the bound antibody; and selecting an anti-cancer therapy for the subject based on the presence or expression level of PD-L1 in the sample.

For example, the invention provides a method for selecting a therapy for a subject suffering from a cancer, the method comprising: determining the presence or expression level of PD-L1 in a sample obtained from the subject by contacting the sample with an anti-PD-L1 antibody of the invention (e.g., SP142) and detecting the presence of the bound antibody; and selecting an anti-cancer therapy for the subject based on the presence or expression level of PD-L1 in the sample. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof.

In any of the preceding methods, the tumor sample may have a detectable expression level of PD-L1 in tumor-infiltrating immune cells that comprise about 1% or more (e.g., about 1% or more, about 2% or more, about 3% or more, about 4% or more, about 5% or more, about 10% or more, about 15% or more, about 20% or more, about 25% or more, about 30% or more, about 35% or more, about 40% or more, about 50% or more, about 55% or more, about 60% or more, about 65% or more, about 70% or more, about 80% or more, about 85% or more, about 90% or more, about 95% or more, or about 99% or more) of the tumor sample, for example, by area. For example, in some instances, the tumor sample may have a detectable expression level of PD-L1 in tumor-infiltrating immune cells that comprise about 1% to less than about 99% (e.g., about 1% to less than about 95%, about 1% to less than about 90%, about 1% to less than about 85%, about 1% to less than about 80%, about 1% to less than about 75%, about 1% to less than about 70%, about 1% to less than about 65%, about 1% to less than about 60%, about 1% to less than about 55%, about 1% to less than about 50%, about 1% to less than about 40%, about 1% to less than about 35%, about 1% to less than about 30%, about 1% to less than about 25%, about 1% to less than about 20%, about 1% to less than about 15%, about 1% to less than about 10%, about 1% to less than about 5%, about 5% to less than about 95%, about 5% to less than about 90%, about 5% to less than about 85%, about 5% to less than about 80%, about 5% to less than about 75%, about 5% to less than about 70%, about 5% to less than about 65%, about 5% to less than about 60%, about 5% to less than about 55%, about 5% to less than about 50%, about 5% to less than about 40%, about 5% to less than about 35%, about 5% to less than about 30%, about 5% to less than about 25%, about 5% to less than about 20%, about 5% to less than about 15%, about 5% to less than about 10%, about 10% to less than about 95%, about 10% to less than about 90%, about 10% to less than about 85%, about 10% to less than about 80%, about 10% to less than about 75%, about 10% to less than about 70%, about 10% to less than about 65%, about 10% to less than about 60%, about 10% to less than about 55%, about 10% to less than about 50%, about 10% to less than about 40%, about 10% to less than about 35%, about 10% to less than about 30%, about 10% to less than about 25%, about 10% to less than about 20%, about 10% to less than about 15%) of the tumor sample, for example, by area. For example, in some instances, the tumor may have a detectable expression level of PD-L1 in tumor-infiltrating immune cells that comprise about 1% or more to less than 5% of the tumor sample, for example, by area. In other instances, the tumor may have a detectable expression level of PD-L1 in tumor-infiltrating immune cells that comprise about 5% or more to less than 10% of the tumor sample, for example, by area. In other instances, the tumor may have a detectable expression level of PD-L1 in tumor-infiltrating immune cells that comprise about 10% or more of the tumor sample, for example, by area.

In any of the preceding methods, the tumor sample may have a detectable expression level of PD-L1 in about 1% or more (e.g., about 1% or more, about 2% or more, about 3% or more, about 4% or more, about 5% or more, about 10% or more, about 15% or more, about 20% or more, about 25% or more, about 30% or more, about 35% or more, about 40% or more, about 50% or more, about 55% or more, about 60% or more, about 65% or more, about 70% or more, about 80% or more, about 85% or more, about 90% or more, about 95% or more, or about 99% or more) of the tumor cells in the tumor sample. For example, in some instances, the tumor sample may have a detectable expression level of PD-L1 in about 1% to less than about 99% (e.g., about 1% to less than about 95%, about 1% to less than about 90%, about 1% to less than about 85%, about 1% to less than about 80%, about 1% to less than about 75%, about 1% to less than about 70%, about 1% to less than about 65%, about 1% to less than about 60%, about 1% to less than about 55%, about 1% to less than about 50%, about 1% to less than about 40%, about 1% to less than about 35%, about 1% to less than about 30%, about 1% to less than about 25%, about 1% to less than about 20%, about 1% to less than about 15%, about 1% to less than about 10%, about 1% to less than about 5%, about 5% to less than about 95%, about 5% to less than about 90%, about 5% to less than about 85%, about 5% to less than about 80%, about 5% to less than about 75%, about 5% to less than about 70%, about 5% to less than about 65%, about 5% to less than about 60%, about 5% to less than about 55%, about 5% to less than about 50%, about 5% to less than about 40%, about 5% to less than about 35%, about 5% to less than about 30%, about 5% to less than about 25%, about 5% to less than about 20%, about 5% to less than about 15%, about 5% to less than about 10%, about 10% to less than about 95%, about 10% to less than about 90%, about 10% to less than about 85%, about 10% to less than about 80%, about 10% to less than about 75%, about 10% to less than about 70%, about 10% to less than about 65%, about 10% to less than about 60%, about 10% to less than about 55%, about 10% to less than about 50%, about 10% to less than about 40%, about 10% to less than about 35%, about 10% to less than about 30%, about 10% to less than about 25%, about 10% to less than about 20%, about 10% to less than about 15%) of the tumor cells in the tumor sample. For example, in some instances, the tumor sample may have a detectable expression level of PD-L1 in about 1% or more to less than 5% of the tumor cells in the tumor sample. In other instances, the tumor may have a detectable expression level of PD-L1 in about 5% or more to less than 10% of the tumor cells in the tumor sample. In other instances, the tumor may have a detectable expression level of PD-L1 in about 10% or more of the tumor cells in the tumor sample.

In any of the preceding methods, the cancer may be non-small cell lung cancer (NSCLC), squamous cell cancer (including adenocarcinoma of the lung and squamous carcinoma of the lung), small-cell lung cancer, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia, and head and neck cancer. In some instances, the cancer is NSCLC. In some embodiments, the NSCLC is adenocarcinoma of the lung or squamous carcinoma of the lung. In some embodiments, the NSCLC is squamous NSCLC or non-squamous NSCLC.

The benefit and/or response of any of the preceding methods may be any known in the art and/or described herein, for example, (1) inhibition, to some extent, of disease progression (e.g., cancer progression), including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e. reduction, slowing down or complete stopping) of metastasis; (5) relief, to some extent, of one or more symptoms associated with the disease or disorder (e.g., cancer); (6) increase or extend in the length of survival, including overall survival and progression free survival; and/or (9) decreased mortality at a given point of time following treatment. In some instances, such benefit includes any one or more of: extending survival (including overall survival and progression-free survival); resulting in an objective response (including a complete response or a partial response); or improving signs or symptoms of cancer.

Any of the preceding methods may further include administering to the subject a therapeutically effective amount of an anti-cancer therapy based on the expression level of PD-L1 in the sample. In some instances, the anti-cancer therapy comprises a PD-1 axis binding antagonist. The PD-1 axis binding antagonist may be any PD-1 axis binding antagonist known in the art or described herein.

For example, in some instances, the PD-1 axis binding antagonist is selected from the group consisting of a PD-L1 binding antagonist, a PD-1 binding antagonist, and a PD-L2 binding antagonist. In some instances, the PD-1 axis binding antagonist is a PD-L1 binding antagonist. In some instances, the PD-L1 binding antagonist inhibits the binding of PD-L1 to one or more of its ligand binding partners. In other instances, the PD-L1 binding antagonist inhibits the binding of PD-L1 to PD-1. In yet other instances, the PD-L1 binding antagonist inhibits the binding of PD-L1 to B7-1. In some instances, the PD-L1 binding antagonist inhibits the binding of PD-L1 to both PD-1 and B7-1. In some instances, the PD-L1 binding antagonist is an antibody. In some embodiments, the antibody is selected from the group consisting of: YW243.55.S70, MPDL3280A (atezolizumab), MDX-1105, MED14736 (durvalumab), and MSB0010718C (avelumab).

In some instances, the PD-1 axis binding antagonist is a PD-1 binding antagonist. For example, in some instances, the PD-1 binding antagonist inhibits the binding of PD-1 to one or more of its ligand binding partners. In some instances, the PD-1 binding antagonist inhibits the binding of PD-1 to PD-L1. In other instances, the PD-1 binding antagonist inhibits the binding of PD-1 to PD-L2. In yet other instances, the PD-1 binding antagonist inhibits the binding of PD-1 to both PD-L1 and PD-L2. In some instances, the PD-1 binding antagonist is an antibody. In some instances, the antibody is selected from the group consisting of: MDX 1106 (nivolumab), MK-3475 (pembrolizumab), CT-011 (pidilizumab), MEDI-0680 (AMP-514), PDR001, REGN2810, and BGB-108. In some instances, the PD-1 binding antagonist is an Fc-fusion protein. For example, in some instances, the Fc-fusion protein is AMP-224.

In some instances, the method further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof.

The sample used in any of the preceding embodiments may be as described below in Section F, "Biological Samples." In some embodiments, the tumor sample comprises tumor cells, tumor-infiltrating immune cells, stromal cells, or any combinations thereof. In any of the preceding embodiments, the tumor sample may be a formalin-fixed and paraffin-embedded (FFPE) tumor sample, an archival tumor sample, a fresh tumor sample, or a frozen tumor sample.

In certain embodiments, the presence and/or expression level/amount of PD-L1 in a sample may be determined using IHC and staining protocols. IHC staining of tissue sections has been shown to be a reliable method of determining or detecting the presence of proteins in a sample. In one embodiment, expression level of PD-L1 is determined using a method comprising: (a) performing IHC analysis of a sample (such as a tumor sample obtained from a subject) with an anti-PD-L1 antibody of the invention, e.g., SP142; and (b) determining the presence and/or expression level of PD-L1 in the sample. In some embodiments, IHC staining intensity is determined relative to a reference. In some embodiments, the reference is a reference value. In some embodiments, the reference is a reference sample (e.g., a control cell line staining sample, a tissue sample from non-cancerous patient, a reference sample known to have a pre-determined level of PD-L1 expression (e.g., a reference sample with a defined IC % or TC %), or a PD-L1-negative tumor sample).

IHC may be performed in combination with additional techniques such as morphological staining and/or in situ hybridization (e.g., FISH). Two general methods of IHC are available; direct and indirect assays. According to the first assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody. The primary and/or secondary antibody used for IHC typically will be labeled with a detectable moiety. Numerous labels are available which can be generally grouped into the following categories: (a) radioisotopes, such as $^{35}S$, $^{14}C$, $^{125}I$, $^{3}H$, and $^{131}I$; (b) colloidal gold particles; (c) fluorescent labels including, but are not limited to, rare earth chelates (europium chelates), Texas Red, rhodamine, fluorescein, dansyl, lissamine, umbelliferone, phycocrytherin, phycocyanin, or commercially-available fluorophores such as SPECTRUM ORANGE7 and SPECTRUM GREEN7 and/or derivatives of any one or more of the above; (d) various enzyme-substrate labels are available and U.S. Pat. No. 4,275,149 provides a review of some of these. Examples of enzymatic labels include luciferases (e.g., firefly luciferase and bacterial luciferase; see, e.g., U.S. Pat. No. 4,737,456), luciferin, 2,3-dihydrophthalazinediones, malate dehydrogenase, urease, peroxidase such as horseradish peroxidase (HRPO), alkaline phosphatase, p-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example, horseradish peroxidase (HRPO) with hydrogen peroxidase as a substrate; alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). For a general review of these, see, for example, U.S. Pat. Nos. 4,275,149 and 4,318,980.

Specimens may be prepared, for example, manually, or using an automated staining instrument (e.g., a Ventana BenchMark XT or Benchmark ULTRA instrument). Specimens thus prepared may be mounted and coverslipped. Slide evaluation is then determined, for example, using a microscope, and staining intensity criteria, routinely used in the art, may be employed. In one embodiment, it is to be understood that when cells and/or tissue from a tumor is examined using IHC, staining is generally determined or assessed in tumor cell(s) and/or tissue (as opposed to stromal or surrounding tissue that may be present in the sample). In some embodiments, it is understood that when cells and/or tissue from a tumor is examined using IHC, staining includes determining or assessing in tumor-infiltrating immune cells, including intratumoral or peritumoral immune cells. In some embodiments, the presence of PD-L1 is detected by IHC in >0% of the sample, in at least 1% of the sample, in at least 5% of the sample, in at least 10% of the sample, in at least 15% of the sample, in at least 15% of the sample, in at least 20% of the sample, in at least 25% of the sample, in at least 30% of the sample, in at least 35% of the sample, in at least 40% of the sample, in at least 45% of the sample, in at least 50% of the sample, in at least 55% of the sample, in at least 60% of the sample, in at least 65% of the sample, in at least 70% of the sample, in at least 75% of the sample, in at least 80% of the sample, in at least 85% of the sample, in at least 90% of the sample, in at least 95% of the sample, or more. Samples may be scored using any of the criteria described herein, for example, by a pathologist or using automated image analysis.

In some embodiments of any of the preceding methods, the expression level of PD-L1 is detected in tumor cells, tumor-infiltrating immune cells, or combinations thereof, for example, using IHC. Tumor-infiltrating immune cells include, but are not limited to, intratumoral immune cells, peritumoral immune cells or any combinations thereof, and other tumor stroma cells (e.g., fibroblasts). Such tumor infiltrating immune cells may be T lymphocytes (such as CD8+ T lymphocytes and/or CD4+ T lymphocytes), B lymphocytes, or other bone marrow-lineage cells including granulocytes (neutrophils, eosinophils, basophils), monocytes, macrophages, dendritic cells (e.g., interdigitating dendritic cells), histiocytes, and natural killer cells. In some embodiments, the staining for PD-L1 is detected as membrane staining, cytoplasmic staining and combinations thereof. In other embodiments, the absence of PD-L1 is detected as absent or no staining in the sample. In some embodiments, the method comprises determining the percentage of tumor area covered by tumor-infiltrating immune cells expressing a detectable amount of PD-L1, for example, as described herein (see, e.g., IC % as described in Example 5). In some embodiments, the method comprises determining the percentage of tumor cells in the tumor sample that express a detectable amount of PD-L1, for example, as described herein (see, e.g., Example 5).

In certain instances, labeled anti-PD-L1 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, for example, through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

It is also understood that any of the above methods for diagnosis and/or detection may be carried out using an immunoconjugate of the invention, as described above, in place of or in addition to an unconjugated anti-PD-L1 antibody.

F. Biological Samples

In certain embodiments, the anti-PD-L1 antibodies of the invention (e.g., SP142 or any other anti-PD-L1 antibody described, for example, above in Section A, "Exemplary Anti-PD-L1 Antibodies") can be used to detect the presence of PD-L1 in biological samples using methods known in the art or described herein.

In some instances a biological sample includes a tissue or a cell sample. For example, a biological sample may include a cell or tissue from normal or cancer patients, such as, for example, normal and cancerous tissue of breast, colon, lung, kidney, bone, brain, muscle, stomach, pancreas, bladder, ovary, uterus, as well as heart, embryonic, and placental tissue.

In certain instances the source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments the biological sample is obtained from in vitro tissue or cell culture. Examples of biological samples herein include, but are not limited to, tumor biopsies, circulating tumor cells, serum or plasma, circulating plasma proteins, ascitic fluid, primary cell cultures or cell lines derived from tumors or exhibiting tumor-like properties, as well as preserved tumor samples, such as formalin-fixed, paraffin-embedded (FFPE) tumor samples or frozen tumor samples.

In some embodiments the biological sample contains compounds which are not naturally intermixed with the tissue in nature such as preservatives, anticoagulants, buffers, nutrients, antibiotics, or the like. In certain embodiments the biological sample has been exposed to and/or contains one or more fixatives. Fixatives that can be used with methods and compositions of the invention include formalin, glutaraldehyde, osmium tetraoxide, acetic acid, ethanol, acetone, picric acid, chloroform, potassium dichromate and mercuric chloride and/or stabilizing by microwave heating or freezing.

In some embodiments, the biological sample is from a subject having, predisposed to, or being tested for an immune dysfunction. In certain embodiments, the immune dysfunction is a T-cell dysfunctional disorder. In some embodiments, the T cell dysfunctional disorder is unresolved acute infection, chronic infection or tumor immunity. In certain embodiments, the immune dysfunction is an autoimmune disease. In some embodiments, the autoimmune disease is an autoimmune rheumatologic disorder (including rheumatoid arthritis, Sjogren's syndrome, scleroderma, lupus such as SLE and lupus nephritis, polymyositis-dermatomyositis, cryoglobulinemia, anti-phospholipid antibody syndrome, and psoriatic arthritis), an autoimmune gastrointestinal and liver disorder (including inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (including ANCA-negative vasculitis and ANCA-associated vasculitis, including Churg-Strauss vasculitis, Wegener's granulomatosis, and microscopic polyangiitis), an autoimmune neurological disorder (including multiple sclerosis, opsoclonus myoclonus syndrome, myasthenia gravis, neuromyelitis optica, Parkinson's disease, Alzheimer's disease, and autoimmune polyneuropathies), a renal disorder (including glomerulonephritis, Goodpasture's syndrome, and Berger's disease), an autoimmune dermatologic disorder (including psoriasis, urticaria, hives, pemphigus vulgaris, bullous pemphigoid, and cutaneous lupus erythematosus), a hematologic disorder (including thrombocytopenic purpura, thrombotic thrombocytopenic purpura, post-transfusion purpura, and autoimmune hemolytic anemia), atherosclerosis, uveitis, an autoimmune hearing disease (including inner ear disease and hearing loss), Behcet's disease, Raynaud's syndrome, organ transplant, or an autoimmune endocrine disorder (including diabetic-related autoimmune diseases such as insulin-dependent diabetes mellitus (IDDM), Addison's disease, and autoimmune thyroid disease (including Graves' disease and thyroiditis)).

In other embodiments, the biological sample is from a subject having, predisposed to, or being tested for cancer. In certain embodiments the cancer is non-small cell lung cancer (NSCLC) (including adenocarcinoma of the lung and squamous carcinoma of the lung), carcinoma, lymphoma (including Hodgkin's and non-Hodgkin's lymphoma), blastoma, sarcoma, leukemia, squamous cell cancer, small-cell lung cancer, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, or various types of head and neck cancer. In particular embodiments, the cancer is NSCLC. In some embodiments, the NSCLC is adenocarcinoma of the lung or squamous carcinoma of the lung. In some embodiments, the NSCLC is non-squamous NSCLC or squamous NSCLC.

G. Therapeutic Methods Based on PD-L1 Presence and/or Expression Level

The invention provides methods of treating a subject suffering from a disorder (e.g., a cancer or an immune dysfunction) based on the presence and/or expression level of PD-L1 in a sample obtained from the subject, as determined using an anti-PD-L1 antibody of the invention. In some cases, the methods involve administration of a treatment (e.g., an anti-cancer therapy) based on the presence and/or expression level of PD-L1 in a sample obtained from the subject, as determined using an anti-PD-L1 antibody of the invention. In some instances, the therapeutic methods involve correlating the presence and/or expression level of PD-L1, as determined using an anti-PD-L1 antibody of the invention, with the subject's likelihood of benefiting or responding to the anti-cancer therapy, for example, as described herein.

The method provides a method of treating a subject suffering from a disorder (e.g., a cancer or an immune dysfunction), the method comprising: determining the presence or expression level of PD-L1 in a sample obtained from the subject by contacting the sample with an anti-PD-L1 antibody of the invention (e.g., SP142) and detecting the presence of the bound antibody; and administering a therapeutically effective amount of a therapy to the subject.

For example, the method provides a method of treating a subject suffering from a cancer, the method comprising: determining the presence or expression level of PD-L1 in a sample obtained from the subject by contacting the sample with an anti-PD-L1 antibody of the invention (e.g., SP142) and detecting the presence of the bound antibody; and administering a therapeutically effective amount of an anti-cancer therapy to the subject. In some instances, the sample is selected from the group consisting of a tissue sample, a whole blood sample, a serum sample, and a plasma sample. In some instances, the tissue sample is a tumor sample. In some instances, the tumor sample comprises tumor-infiltrating immune cells, tumor cells, stromal cells, and any combinations thereof. In any of the preceding methods, the tumor sample may have a detectable expression level of PD-L1 in tumor-infiltrating immune cells that comprise about 1% or more (e.g., about 1% or more, about 2% or more, about 3% or more, about 4% or more, about 5% or more, about 10% or more, about 15% or more, about 20% or more, about 25% or more, about 30% or more, about 35% or more, about 40% or more, about 50% or more, about 55% or more, about 60% or more, about 65% or more, about 70% or more, about 80% or more, about 85% or more, about 90% or more, about 95% or more, or about 99% or more) of the tumor sample, for example, by area. For example, in some instances, the tumor sample may have a detectable expression level of PD-L1 in tumor-infiltrating immune cells that comprise about 1% to less than about 99% (e.g., about 1% to less than about 95%, about 1% to less than about 90%, about 1% to less than about 85%, about 1% to less than about 80%, about 1% to less than about 75%, about 1% to less than about 70%, about 1% to less than about 65%, about 1% to less than about 60%, about 1% to less than about 55%, about 1% to less than about 50%, about 1% to less than about 45%, about 1% to less than about 40%, about 1% to less than about 35%, about 1% to less than about 30%, about 1% to less than about 25%, about 1% to less than about 20%, about 1% to less than about 15%, about 1% to less than about 10%, about 1% to less than about 5%, about 5% to less than about 95%, about 5% to less than about 90%, about 5% to less than about 85%, about 5% to less than about 80%, about 5% to less than about 75%, about 5% to less than about 70%, about 5% to less than about 65%, about 5% to less than about 60%, about 5% to less than about 55%, about 5% to less than about 50%, about 5% to less than about 40%, about 5% to less than about 35%, about 5% to less than about 30%, about 5% to less than about 25%, about 5% to less than about 20%, about 5% to less than about 15%, about 5% to less than about 10%, about 10% to less than about 95%, about 10% to less than about 90%, about 10% to less than about 85%, about 10% to less than about 80%, about 10% to less than about 75%, about 10% to less than about 70%, about 10% to less than about 65%, about 10% to less than about 60%, about 10% to less than about 55%, about 10% to less than about 50%, about 10% to less than about 40%, about 10% to less than about 35%, about 10% to less than about 30%, about 10% to less than about 25%, about 10% to less than about 20%, about 10% to less than about 15%) of the tumor sample, for example, by area. For example, in some instances, the tumor may have a detectable expression level of PD-L1 in tumor-infiltrating immune cells that comprise about 1% or more to less than 5% of the tumor sample, for example, by area. In other instances, the tumor may have a detectable expression level of PD-L1 in tumor-infiltrating immune cells that comprise about 5% or more to less than 10% of the tumor sample, for example, by area. In other instances, the tumor may have a detectable expression level of PD-L1 in tumor-infiltrating immune cells that comprise about 10% or more of the tumor sample, for example, by area.

In any of the preceding methods, the tumor sample may have a detectable expression level of PD-L1 in about 1% or more (e.g., about 1% or more, about 2% or more, about 3% or more, about 4% or more, about 5% or more, about 10% or more, about 15% or more, about 20% or more, about 25% or more, about 30% or more, about 35% or more, about 40% or more, about 50% or more, about 55% or more, about 60% or more, about 65% or more, about 70% or more, about 80% or more, about 85% or more, about 90% or more, about 95% or more, or about 99% or more) of the tumor cells in the tumor sample. For example, in some instances, the tumor sample may have a detectable expression level of PD-L1 in about 1% to less than about 99% (e.g., about 1% to less than about 95%, about 1% to less than about 90%, about 1% to less than about 85%, about 1% to less than about 80%, about 1% to less than about 75%, about 1% to less than about 70%, about 1% to less than about 65%, about 1% to less than about 60%, about 1% to less than about 55%, about 1% to less than about 50%, about 1% to less than about 40%, about 1% to less than about 35%, about 1% to less than about 30%, about 1% to less than about 25%, about 1% to less than about 20%, about 1% to less than about 15%, about 1% to less than about 10%, about 1% to less than about 5%, about 5% to less than about 95%, about 5% to less than about 90%, about 5% to less than about 85%, about 5% to less than about 80%, about 5% to less than about 75%, about 5% to less than about 70%, about 5% to less than about 65%, about 5% to less than about 60%, about 5% to less than about 55%, about 5% to less than about 50%, about 5% to less than about 40%, about 5% to less than about 35%, about 5% to less than about 30%, about 5% to less than about 25%, about 5% to less than about 20%, about 5% to less than about 15%, about 5% to less than about 10%, about 10% to less than about 95%, about 10% to less than about 90%, about 10% to less than about 85%, about 10% to less than about 80%, about 10% to less than about 75%, about 10% to less than about 70%, about 10% to less than about 65%, about 10% to less than about 60%, about 10% to less than about 55%, about 10% to less than about 50%, about 10% to less than about 40%, about 10% to less than about 35%, about 10% to less than about 30%, about 10% to less than about 25%, about 10% to less than about 20%, about 10% to less than about 15%) of the tumor cells in the tumor sample. For example, in some instances, the tumor sample may have a detectable expression level of PD-L1 in about 1% or more to less than 5% of the tumor cells in the tumor sample. In other instances, the tumor may have a detectable expression level of PD-L1 in about 5% or more to less than 10% of the tumor cells in the tumor sample. In other instances, the tumor may have a detectable expression level of PD-L1 in about 10% or more of the tumor cells in the tumor sample.

In any of the preceding methods, the cancer may be non-small cell lung cancer (NSCLC) (including adenocarcinoma of the lung and squamous carcinoma of the lung), squamous cell cancer, small-cell lung cancer, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia, and head and neck cancer. In some instances, the cancer is NSCLC. In some embodiments, the NSCLC is adenocarcinoma of the lung or squamous carcinoma of the lung. In some embodiments, the NSCLC is non-squamous NSCLC or squamous NSCLC.

In any of the preceding methods, the anti-cancer therapy may include a PD-1 axis binding antagonist. In some instances, the method may include administering to the patient a therapeutically effective amount of a PD-1 axis binding antagonist based on the expression level of PD-L1 in tumor cells and/or in tumor-infiltrating immune cells in a tumor sample. The PD-1 axis binding antagonist may be any PD-1 axis binding antagonist known in the art or described herein.

For example, in some instances, the PD-1 axis binding antagonist includes a PD-1 binding antagonist, a PD-L1 binding antagonist, and a PD-L2 binding antagonist. PD-1 (programmed death 1) is also referred to in the art as "programmed cell death 1," "PDCD1," "CD279," and "SLEB2." An exemplary human PD-1 is shown in UniProtKB/Swiss-Prot Accession No. Q15116. PD-L1 (programmed death ligand 1) is also referred to in the art as "programmed cell death 1 ligand 1," "PDCD1 LG1," "CD274," "B7-H," and "PDL1." An exemplary human PD-L1 is shown in UniProtKB/Swiss-Prot Accession No. Q9NZQ7.1. PD-L2 (programmed death ligand 2) is also referred to in the art as "programmed cell death 1 ligand 2," "PDCD1 LG2," "CD273," "B7-DC," "Btdc," and "PDL2." An exemplary human PD-L2 is shown in UniProtKB/Swiss-Prot Accession No. Q9BQ51. In some embodiments, PD-1, PD-L1, and PD-L2 are human PD-1, PD-L1 and PD-L2.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding ligands. In a specific aspect, PD-L1 binding partners are PD-1 and/or B7-1. In another embodiment, the PD-L2 binding antagonist is a molecule that inhibits the binding of PD-L2 to its ligand binding partners. In a specific aspect, the PD-L2 binding ligand partner is PD-1. The antagonist may be an antibody, an antigen binding fragment thereof, an immunoadhesin, a fusion protein, or oligopeptide.

In some embodiments, the PD-1 binding antagonist is an anti-PD-1 antibody (e.g., a human antibody, a humanized antibody, or a chimeric antibody), for example, as described below. In some embodiments, the anti-PD-1 antibody is selected from the group consisting of MDX-1106 (nivolumab), MK-3475 (pembrolizumab), CT-011 (pidilizumab). MEDI-0680 (AMP-514), PDR001, REGN2810, and BGB-108. MDX-1106, also known as MDX-1106-04, ONO-4538, BMS-936558, or nivolumab, is an anti-PD-1 antibody described in WO2006/121168. MK-3475, also known as pembrolizumab or lambrolizumab, is an anti-PD-1 antibody described in WO 2009/114335. CT-011, also known as hBAT, hBAT-1 or pidilizumab, is an anti-PD-1 antibody described in WO 2009/101611. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. AMP-224, also known as B7-DCIg, is a PD-L2-Fc fusion soluble receptor described in WO 2010/027827 and WO 2011/066342.

In some embodiments, the anti-PD-1 antibody is MDX-1106. Alternative names for "MDX-1106" include MDX-1106-04, ONO-4538, BMS-936558, and nivolumab. In some embodiments, the anti-PD-1 antibody is nivolumab (CAS Registry Number: 946414-94-4).

In some embodiments, the PD-1 axis binding antagonist is a PD-L2 binding antagonist. In some embodiments, the PD-L2 binding antagonist is an anti-PD-L2 antibody (e.g., a human antibody, a humanized antibody, or a chimeric antibody). In some embodiments, the PD-L2 binding antagonist is an immunoadhesin.

In some embodiments, the PD-L1 binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody. In some embodiments, the anti-PD-L1 antibody is selected from the group consisting of YW243.55.S70, MPDL3280A (atezolizumab), MDX-1105, MEDI4736 (durvalumab), and MSB0010718C (avelumab). Antibody YW243.55.S70 is an anti-PD-L1 described in WO 2010/077634 and U.S. Pat. No. 8,217,149, the entirety of each of which is incorporated herein by reference. MDX-1105, also known as BMS-936559, is an anti-PD-L1 antibody described in WO 2007/005874. MEDI4736 is an anti-PD-L1 monoclonal antibody described in WO 2011/066389 and US 2013/034559. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559, the entirety of each of which is incorporated herein by reference.

In any of the preceding embodiments, the isolated anti-PD-L1 antibody can bind to a human PD-L1, for example a human PD-L1 as shown in UniProtKB/Swiss-Prot Accession No. Q9NZQ7.1, or a variant thereof.

In a still further embodiment, provided is an isolated nucleic acid encoding any of the antibodies described herein. In some embodiments, the nucleic acid further comprises a vector suitable for expression of the nucleic acid encoding any of the previously described anti-PD-L1 antibodies. In a still further specific aspect, the vector is in a host cell suitable for expression of the nucleic acid. In a still further specific aspect, the host cell is a eukaryotic cell or a prokaryotic cell. In a still further specific aspect, the eukaryotic cell is a mammalian cell, such as Chinese hamster ovary (CHO) cell.

The antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment. It is expressly contemplated that such PD-1 axis binding antagonist antibodies (e.g., anti-PD-L1 antibodies, anti-PD-1 antibodies, and anti-PD-L2 antibodies), or other antibodies described herein (e.g., anti-PD-L1 antibodies for detection of PD-L1 expression levels) for use in any of the embodiments enumerated above may have any of the features, singly or in combination, described in Subsections 1-5 of Section A, "Exemplary Anti-PD-L1 Antibodies."

In some instances, any of the preceding methods further includes administering to the patient an effective amount of a second therapeutic agent. In some instances, the second therapeutic agent is selected from the group consisting of a cytotoxic agent, a growth-inhibitory agent, a radiation therapy agent, an anti-angiogenic agent, and combinations thereof.

The compositions utilized in the methods described herein (e.g., anti-cancer therapeutic agents) can be administered by any suitable method, including, for example, intravenously, intramuscularly, subcutaneously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subconjunctivally, intravesicularly, mucosally, intrapericardially, intraumbilically, intraocularly, intraorbitally, orally, topically, transdermally, intravitreally (e.g., by intravitreal injection), by eye drop, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). In some embodiments, the anti-cancer therapy (e.g., a PD-1 axis binding antagonist) is administered intravenously, intramuscularly, subcutaneously, topically, orally, transdermally, intraperitoneally, intraorbitally, by implantation, by inhalation, intrathecally, intraventricularly, or intranasally. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Therapeutic agents (e.g., PD-1 axis binding antagonists (e.g., an antibody, binding polypeptide, and/or small molecule)) described herein may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutic agent (e.g., a PD-1 axis binding antagonist) need not be, but is optionally formulated with and/or administered concurrently with one or more agents currently used to prevent or treat the disorder in question. The effective amount of such other agents depends on the amount of the therapeutic agent (e.g., a PD-1 axis binding antagonist) present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of a cancer (e.g., a non-small cell lung cancer), the appropriate dosage of a therapeutic agent (e.g., a PD-1 axis binding antagonist) described herein (when used alone or in combination with one or more other additional therapeutic agents) will depend on the type of disease to be treated, the severity and course of the disease, whether the therapeutic agent (e.g., PD-1 axis binding antagonist) is administered for preventive or therapeutic purposes, previous therapy, the patient's clinical history and response to the therapeutic agent (e.g., PD-1 axis binding antagonist), and the discretion of the attending physician. The therapeutic agent (e.g., PD-1 axis binding antagonist) is suitably administered to the patient at one time or over a series of treatments. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g., every week or every three weeks (e.g., such that the patient receives, for example, from about two to about twenty, or e.g., about six doses of the therapeutic agent (e.g., PD-1 axis binding antagonist)). An initial higher loading dose, followed by one or more lower doses may be administered. However, other dosage regimens may be useful. The progress of this therapy is easily monitored by conventional techniques and assays.

For example, as a general proposition, the therapeutically effective amount of an antagonist antibody (e.g., a PD-1 axis binding antagonist antibody) administered to human will be in the range of about 0.01 to about 50 mg/kg of patient body weight, whether by one or more administrations. In some embodiments, the antibody used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg administered daily, weekly, every two weeks, every three weeks, or monthly, for example. In some embodiments, the antibody is administered at 15 mg/kg. However, other dosage regimens may be useful. In one embodiment, an antagonist antibody (e.g., a PD-1 axis binding antagonist antibody) described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, or about 1800 mg on day 1 of 21-day cycles (every three weeks, q3w). The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some embodiments, the methods further involve administering to the patient an effective amount of a second therapeutic agent. In some embodiments, the second therapeutic agent is selected from the group consisting of a cytotoxic agent, a chemotherapeutic agent, a growth-inhibitory agent, a radiation therapy agent, an anti-angiogenic agent, and combinations thereof. In some embodiments, a therapeutic agent (e.g., PD-1 axis binding antagonist) may be administered in conjunction with a chemotherapy or chemotherapeutic agent. In some embodiments, a therapeutic agent (e.g., PD-1 axis binding antagonist) may be administered in conjunction with a radiation therapy agent. In some embodiments, a therapeutic agent (e.g., PD-1 axis binding antagonist) may be administered in conjunction with a targeted therapy or targeted therapeutic agent. In some embodiments, a therapeutic agent (e.g., PD-1 axis binding antagonist) may be administered in conjunction with an immunotherapy or immunotherapeutic agent, for example a monoclonal antibody.

Such combination therapies noted above encompass combined administration (where two or more therapeutic agents are included in the same or separate formulations), and separate administration, in which case, administration of a therapeutic agent (e.g., PD-1 axis binding antagonist) can occur prior to, simultaneously, and/or following, administration of the additional therapeutic agent or agents. In one embodiment, administration of a therapeutic agent (e.g., PD-1 axis binding antagonist) and administration of an additional therapeutic agent occur within about one month, or within about one, two or three weeks, or within about one, two, three, four, five, or six days, of each other Therapeutic formulations of the therapeutic agents (e.g., PD-1 axis binding antagonists) used in accordance with the present invention are prepared for storage by mixing the antagonist having the desired degree of purity with optional pharmaceutically acceptable carriers, excipients, or stabilizers in the form of lyophilized formulations or aqueous solutions. For general information concerning formulations, see, e.g., Gilman et al. (eds.) *The Pharmacological Bases of Therapeutics,* 8th Ed., Pergamon Press, 1990; A. Gennaro (ed.), *Remington's Pharmaceutical Sciences,* 18th Edition, Mack Publishing Co., Pennsylvania, 1990; Avis et al. (eds.) *Pharmaceutical Dosage Forms: Parenteral Medications* Dekker, New York, 1993; Lieberman et al. (eds.) *Pharmaceutical Dosage Forms: Tablets* Dekker, New York, 1990; Lieberman et al. (eds.), *Pharmaceutical Dosage Forms: Disperse Systems* Dekker, New York, 1990; and Walters (ed.) *Dermatological and Transdermal Formulations* (Drugs and the Pharmaceutical Sciences), Vol 119, Marcel Dekker, 2002.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

The formulation herein may also contain more than one active compound, preferably those with complementary activities that do not adversely affect each other. The type and effective amounts of such medicaments depend, for example, on the amount and type of antagonist present in the formulation, and clinical parameters of the subjects.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration must be sterile. This is readily accomplished by filtration through sterile filtration membranes.

It is to be understood that any of the above articles of manufacture may include an immunoconjugate described herein in place of or in addition to an antibody, e.g., an anti-PD-L1 antibody or an anti-PD-1 antibody.

III. Examples

The following are examples of methods and compositions of the invention. It is understood that various other embodiments may be practiced, given the general description provided above.

Example 1. Generation of Anti-PD-L1 Antibodies

Figure 1:
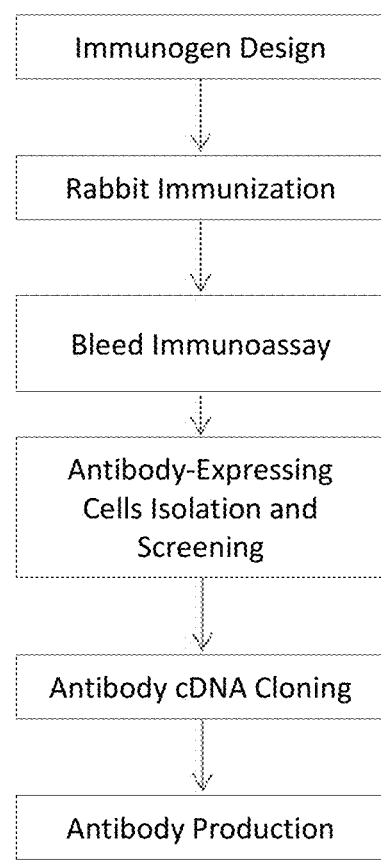
FIG. 1 is a schematic diagram showing the general antibody production process for the SP142 anti-PD-L1 antibody.
Figures 2A, 2B, 2C, 2D:
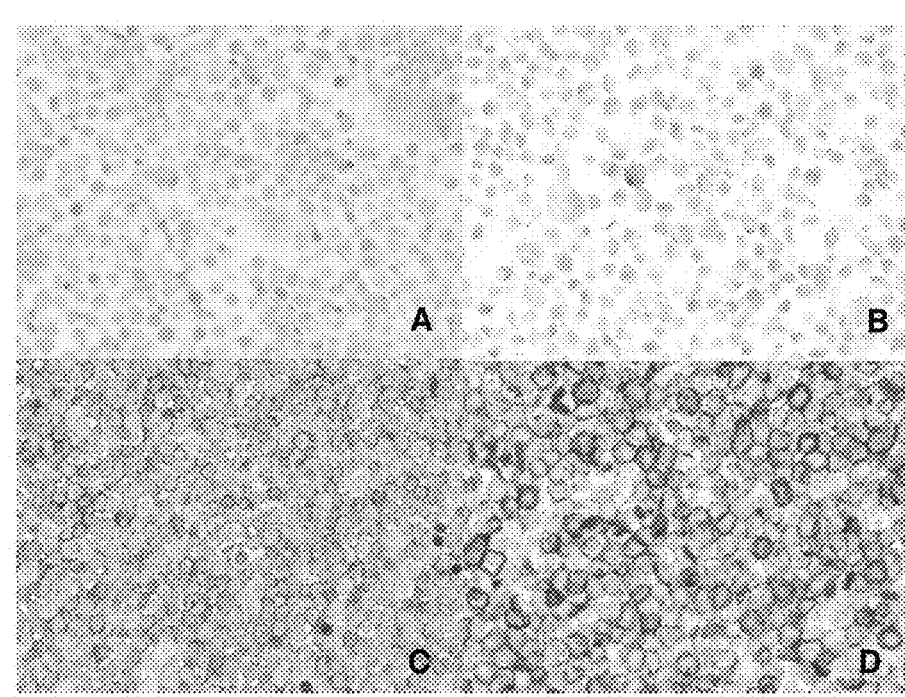
FIG. 2A is an image showing the results of immunohistochemistry (IHC) on formalin-fixed, paraffin-Embedded (FFPE) HEK-293 cells transfected with empty vector (negative control) using anti-PD-L1 antibody SP142.
FIG. 2B is an image showing the results of IHC on FFPE DOR-13 cells (low to medium expression) using anti-PD-L1 antibody SP142.
FIG. 2C is an image showing the results of IHC on FFPE colon carcinoma RKO cells (medium expression) using anti-PD-L1 antibody SP142.
FIG. 2D is an image showing the results of IHC on FFPE HEK-293 cells transfected with full-length human PD-L1 (high expression) using anti-PD-L1 antibody SP142.

Anti-PD-L1 rabbit monoclonal antibodies were generated as schematically depicted in FIG. 1. Briefly, the peptide fragment of the N-terminal cytoplasmic region (amino acid residues 279-290) of human PD-L1 (SKKQSDTHLEET; SEQ ID NO: 1) was synthesized. The 12-amino acid fragment intended for immunization was conjugated to keyhole limpet hemocyanin (KLH), an extensively used carrier protein for stimulating a substantial immune response via antibody production. Appending two amino acids (Cys-Gly) to the naturally occurring N-terminus of the sequence allowed for conjugation to the carrier protein KLH. New Zealand White rabbits were immunized with KLH conjugated PD-L1 antigen emulsified with complete Freund's adjuvant followed by a series of PD-L1 antigen booster emulsified with incomplete Freund's adjuvant. The antibody-expressing cells were screened by enzyme-linked immunoabsorbant assay (ELISA) using the PD-L1 antigen. All ELISA positive clones were further screened by immunohistochemistry (IHC), and the clone producing the antibody with the highest specificity was selected. For recombinant production of anti-PD-L1 antibodies, cDNA coding for the heavy chain and light chain sequences of the antibodies were cloned, expressed by co-transfection, and screened for binding to PD-L1 (SEQ ID NO: 1) by IHC. Anti-PD-L1 monoclonal antibody (SP142) was produced using these methods and subsequently purified by Protein A affinity chromatography. The heavy and light chain variable region sequences of the SP142 antibody are as follows.

```
Heavy chain variable region:
                             (SEQ ID NO: 16)
QSLEESGGRLVKPDETLTITCTVSGIDLSSNGLTWV
                            HVR-H1

RQAPGEGLEWIGTINKDASAYYASWAKGRLTISKP
              HVR-H2

SSTKVDLKITSPTTEDTATYFCGRIAFKTGTSIW
                        HVR-H3

GPGTLVTVSS

Light chain variable region:
                             (SEQ ID NO: 17)
AIVMTQTPSPVSAAVGGTVTINCQASESVYSNNYLSWF
                          HVR-L1

QQKPGQPPKLLIYLASTLASGVPSRFKGSGSGTQFTLT
              HVR-L2

ISGVQCDDAATYYCIGGKSSSTDGNAFGGGTEVVVR
                     HVR-L3
```

Example 2. Diagnostic Uses of Anti-PD-L1 Antibodies

Figures 3A, 3B, 3C:
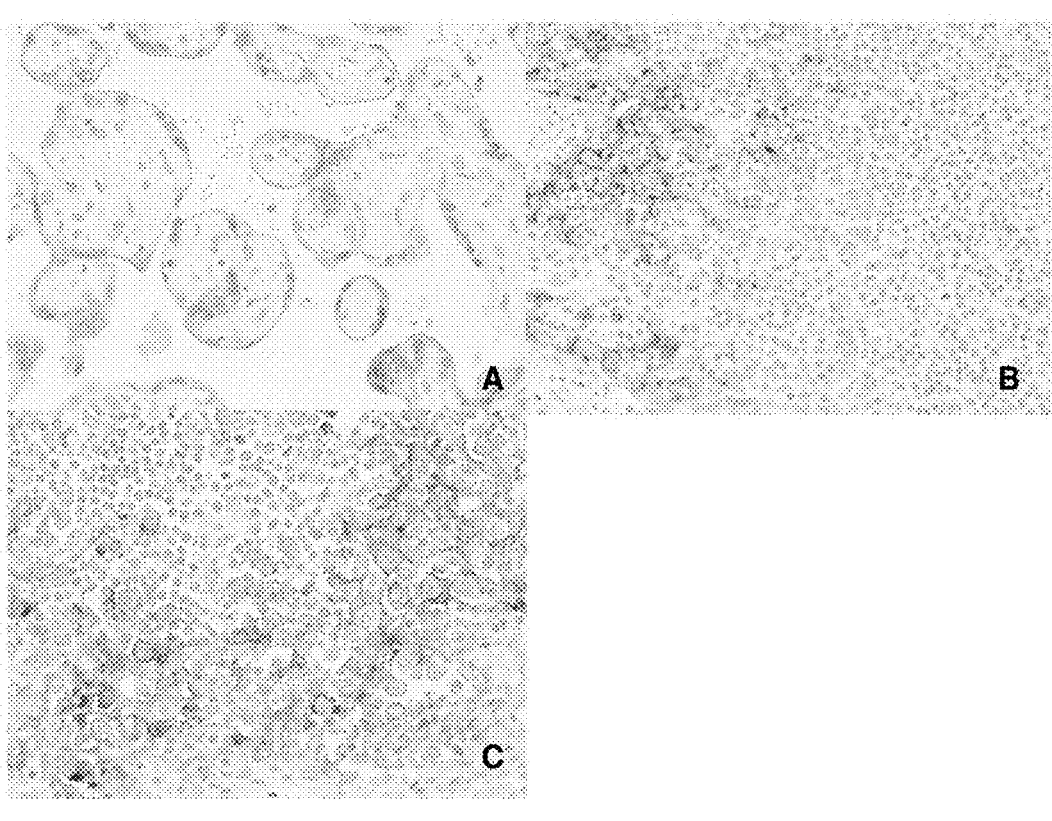
FIG. 3A is an image showing the results of IHC on a FFPE placental tissue section using anti-PD-L1 antibody SP142.
FIG. 3B is an image showing the results of IHC on a FFPE tonsil tissue section using anti-PD-L1 antibody SP142.
FIG. 3C is an image showing the results of IHC on a FFPE Hodgkin (HK) lymphoma patient tissue section using anti-PD-L1 antibody SP142.
Figure 4:
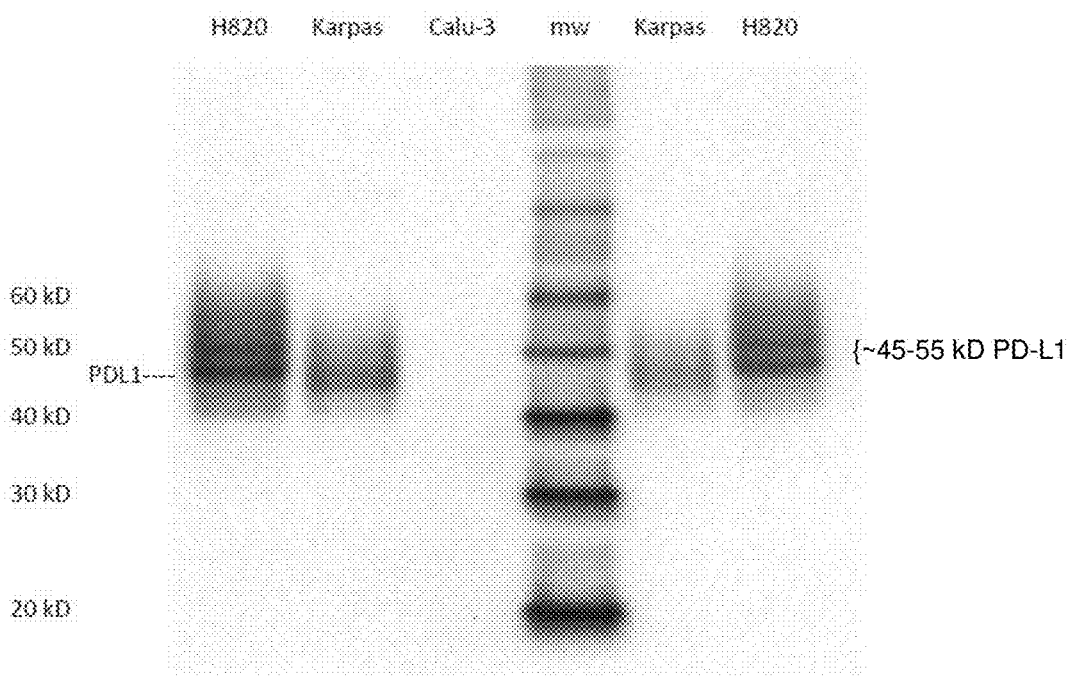
FIG. 4 is a Western blot showing PD-L1 expression in cell lysates from a FFPE NIH H820 lung adenocarcinoma cell line (high expression), a Karpas 299 T cell Lymphoma cell line (intermediate expression), and a Calu-3 lung adenocarcinoma cell line (negative control) using anti-PD-L1 antibody SP142.

The SP142 anti-PD-L1 antibody was used in further IHC and western blot analyses. For IHC analyses, tissue sections were incubated with SP142 for 16 minutes followed by standard washes and secondary detection with goat anti-rabbit biotinylated antibody. The specificity of SP142 was assessed on formalin-fixed, paraffin-embedded (FFPE) cells with different PD-L1 expression levels (human embryonic kidney HEK-293 cells transfected with empty vector as control (negative), as well as DOR-13 (low to medium expression), colon carcinoma RKO cells (medium expression), and PD-L1 transfected 293 cells (high expression); see FIGS. 2A-2D) or from different tissue types (placental tissue, tonsil tissue, and Hodgkin (HK) Lymphoma; see FIGS. 3A-3C). To further determine the specificity of SP142, western blot analysis was performed on cell lysates from cell lines with different PD-L1 expression levels (NIH H820 lung adenocarcinoma cell line (high expression), Karpas 299 T cell Lymphoma cell line (intermediate expression), and Calu-3 lung adenocarcinoma cell line (negative control); see FIG. 4).

Example 3. Comparison of SP142 Anti-PD-L1 Antibody to E1L3N Anti-PD-L1 Antibody The SP142 anti-PD-L1 antibody was compared to anti-PD-L1 antibody E1L3N (Cell Signaling Technology) in IHC analyses of normal and tumor tissue sections, including tissues from non-small cell lung carcinoma (NSCLC) patients. Briefly, for IHC experiments, both SP142 and E1L3N anti-PD-L1 antibodies were serially diluted (0.11-28 μg/ml). Slides for tissue sections were deparaffinized using xylene alternative and graded alcohol. Antigen retrieval was achieved by boiling tissue sections in EDTA buffer (pH 8.0) for 10 minutes followed by cooling at room temperature for 20 minutes. Tissue sections were incubated with either SP142 or E1L3N for 10 minutes followed by standard washes and secondary detection with goat anti-rabbit antibody for 15 minutes. A final incubation with the reporter molecule 3,3'-diaminobenzidine (DAB) was performed for 10 minutes. To assess sensitivity, different concentrations of E1L3N and SP142 were compared on FFPE tissue sections of placenta tissue (see FIGS. 5A-5J). The specificity of E1L3N and SP142 were determined using normal and tumor tissue types (stomach epithelium tissue, nerve tissue, kidney tissue, bladder transitional cell carcinoma (TCC), breast ductal carcinoma (Ca), and lung squamous cell carcinoma (Lung SCCa); see FIGS. 6A-6T and FIGS. 7A-7J). IHC analysis was also performed on sections of different FFPE tissue types stained with either E1L3N or SP142 (tonsil tissue, cervical squamous cell carcinoma (SCC), Hodgkin Lymphoma (HK lymphoma), pancreatic adenocarcinoma, prostate adenocarcinoma, and skin SCC; see FIG. 8A-8L).

Detection of PD-L1 expression with E1L3N and SP142 was then compared in FFPE tissue sections from NSCLSC patients. E1L3N detected 50 PD-L1 positive cases from 119 NSCLC samples previously undetermined for PD-L1 status, and SP142 detected 58 PD-L1-positive cases, wherein 5% or more of tumor cells stained positive was considered indicative of a PD-L1 positive case. To further assess detection of PD-L1 with these antibodies, FFPE tissue sections from NSCLC patients were sequentially stained with both E1L3N and SP142 (FIGS. 9A-9J). The extent of membrane immunoreactivity (i.e., the H score) was then calculated for the 119 NSCLC patient tissue sections stained with E1L3N or SP142. The H score for PD-L1 was calculated with the following formula: H score=3(percentage of strongly staining membrane)+2(percentage of moderately staining membrane)+1(percentage of weakly staining membrane), thereby giving an H score range of 0 to 300. The mean H score from these 119 NSCLC cases was significantly lower for E1L3N (56±8) than for SP142 (100±11). These collective data demonstrate that SP142 is more sensitive and specific than E1L3N.

Example 4. Use of the Anti-PD-L1 Antibody SP142 in IHC Analysis Demonstrates PD-L1 Staining in Immune Cells (IC) and Tumor Cells (TC)

The anti-PD-L1 antibody SP142 detected PD-L1 expression in tumor-infiltrating immune cells (ICs) and tumor cells in representative cases from all cancer types tested (approximately 28-30 types), including but not limited to non-small cell lung cancer (NSCLC), cervical squamous cell carcinoma, HK lymphoma, pancreatic adenocarcinoma, prostate adenocarcinoma, and skin squamous cell carcinoma (see, e.g., FIGS. 8A-8L, 9A-9J, 10, 11, 15A-15B, 16A-16H, and 18A-18F).

Immune Cells (ICs)

Immune cells (ICs) are tumor-infiltrating immune cells present in the intratumoral and contiguous peritumoral stroma that include a morphologically heterogeneous population of cell types, including lymphocytes, macrophages, dendritic cells, and cells with reticular morphology. IHC analyses of tumor tissue sections were performed using the SP142 antibody. In tumor tissue sections, PD-L1-positive ICs often showed a dark brown punctate or discontinuous membrane staining in association with lymphocytes (FIG. 10). PD-L1-positive ICs were typically observed as aggregates in the intratumoral and peritumoral stroma and/or as single cell or diffuse spread among the tumor cell groups (groupings of tumor cells based on location in the tumor section. PD-L1-positive IC staining was also observed at the tumor-stroma interface, and as reticular staining in tertiary lymphoid structures.

Tumor Cells (TCs)

In addition to PD-L1-positive ICs described above, PD-L1-positive tumor cells (TCs) were also determined to be present in tumor samples in IHC analyses using the SP142 antibody. PD-L1-positive TCs were typically characterized by membrane staining (FIG. 11), which was occasionally associated with cytoplasmic staining.

The results demonstrated that the SP-142 antibody can be used to obtain sensitive and specific PD-L1 staining of tumor tissue sections when used in IHC analysis of PD-L1 expression, and further revealed the presence of a PD-L1-positive ICs as well as a PD-L1-positive TCs in tumor tissue sections.

Materials and Methods

FFPE tissue sections were deparaffinized and heated in EDTA antigen retrieval buffer before the rabbit anti-human PD-L1 (SP142) monoclonal antibody was added to the tissue sections. IHC was processed with automatic staining system (BenchMark ULTRA, Roche) or semi-automatic staining system (Autostainer, Thermo Scientific). Table 2 shows the protocol used for the BenchMark ULTRA system.

TABLE 2

| IHC Protocol for BenchMark ULTRA system using SP142 | |
| --- | --- |
| Protocol Selection | BenchMark ULTRA |
| Software Tools | NexES v10.6 |
| Staining Procedure | U OptiView DAB IHC v4 |
| Deparaffinization | Selected |
| Cell Conditioning | 48 minutes CC1 |
| Pre Primary Peroxidase | Selected |
| Primary Incubation | 16 minutes, 36° C. |
| OptiView HQ Linker | 8 minutes |
| OptiView HRP Multimer | 8 minutes |
| OptiView Amplification | Selected |
| Amplifier and Amplification H2O2 | 8 minutes |
| Amplification Multimer | 8 minutes |
| Hematoxylin II | 4 minutes |
| Bluing Reagent | 4 minutes |

Example 5. Determination of PD-L1 Positivity in ICs, TCs, and Combinations Thereof Tissues stained with anti-PD-L1 antibodies (e.g., any of the anti-PD-L1 antibodies of the invention, e.g., SP142) can be scored for the presence of PD-L1-positive ICs, TCs, or combinations of ICs and TCs using different cutoffs (e.g., 1%, 5%, 10%, etc.). These different cutoffs can be used for patient stratification, for example, for selection of patients who are likely to respond to particular anti-cancer therapies (e.g., anti-cancer therapy comprising a PD-1 axis binding antagonist).

Immune Cell Scoring Method

ICs can be scored for PD-L1 expression based on the percentage of tumor area that is covered with PD-L1-positive ICs of any intensity (referred to herein as "IC %"). Tumor area as used herein refers to the area (e.g., the area of a tumor section) occupied by tumor cells as well as their associated intratumoral and contiguous peritumoral stroma (FIGS. 12A-12C). Tumor area was chosen as the denominator in this scoring approach because ICs were present not only within the stroma but also were also present in some cases as single cells or with a diffuse spread within the tumor cells. As described below, in some instances ICs were observed as aggregates within the tumor section, while in other instances ICs were observed as foci of one or a few cells which were spread across the tumor section.

An exemplary workflow for determining the IC % of a tumor sample is shown in FIG. 13. In some instances, serial sections of a tumor sample were stained with either H&E or an anti-PD-L1 antibody (e.g., SP142), as described above. The first step in the workflow was to review the H&E stained slide in order to determine the presence of a tumor, necrosis, and/or ICs. Next, the corresponding PD-L1-stained slide was examined at a low magnification power (e.g., 2× or 4× objective; 20×-40× total magnification), for example, using a microscope, and the overall PD-L1 staining pattern is assessed. For instance, a determination may be made whether the tumor tissue section exhibits PD-L1 staining in ICs, TCs, both ICs and TCs, or whether the tumor tissue section does not exhibit substantial PD-L1 staining. Next, the PD-L1-stained slide was examined at a higher magnification power (e.g., 10× or 20× objective, 100×-200× magnification) to examine stroma and tumor cell groups for IC staining. The use of a higher magnification power enabled confirmation of weak-staining ICs, as well as distinguishing ICs in the midst of strong TC staining. Finally, the PD-L1-stained slide was examined at a lower magnification power (e.g., 2× or 4× objective; 20-40× total magnification) in order to determine or estimate the PD-L1-positive IC percentage (percentage of tumor area that is covered with PD-L1-positive ICs of any intensity).

The percentage of tumor area that is covered with PD-L1-positive ICs with any intensity of PD-L1 staining can be determined at lower magnification power (e.g., 2× or 4× objective; 20-40× total magnification) following reviewing and confirming the staining at higher magnification, for example, as shown in FIG. 14. In cases where the IC staining pattern is characterized by a single cell spread, reference images for particular ranges of IC staining (e.g., 1%, 5%, 10%) may be used for comparison purposes to estimate or determine the percentage of tumor area that is covered with PD-L1-positive ICs having any intensity of PD-L1 staining (see FIGS. 15A and 15B and 16A-16H, for example).

Tumor Cell Scoring Method

Tumor cells (TCs) can be scored for PD-L1 expression based on the percentage of the total number of tumor cells showing any discernible membrane PD-L1 staining of any intensity (also referred to herein as "TC %"). TCs are readily distinguishable from ICs based on cell morphology in H&E and IHC-stained slides. See, for example, FIGS. 17A-17C. Membrane staining should be visible as a linear staining (i.e., lining up along the outline of the cell membrane) even if associated with granular quality. FIGS. 18A-18F show examples of PD-L1-stained NSCLC tumor tissue sections that exhibited particular ranges of TC PD-L1 staining (i.e., TC % of <5%, ≥5 to <50%, or ≥50%).

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated nucleic acid encoding an antibody heavy chain variable domain (VH), wherein the VH comprises the following hypervariable regions (HVR-Hs):
- (a) an HVR-H1 comprising the amino acid sequence of SNGLT (SEQ ID NO: 2);
- (b) an HVR-H2 comprising the amino acid sequence of TINKDASAYYASWAKG (SEQ ID NO: 3); and
- (c) an HVR-H3 comprising the amino acid sequence of IAFKTGTSI (SEQ ID NO: 4).

2. The isolated nucleic acid of claim 1, wherein the VH further comprises the following heavy chain variable domain framework regions (FR-Hs):
- (d) FR-H1 comprising the amino acid sequence of QSLEESGGRLVKPDETLTITCTVSGIDLS (SEQ ID NO: 5);
- (e) FR-H2 comprising the amino acid sequence of WVRQAPGEGLEWIG (SEQ ID NO: 6);
- (f) FR-H3 comprising the amino acid sequence of RLTISKPSSTKVDLKITSPTTEDTATYFCGR (SEQ ID NO: 7); and

- (g) FR-H4 comprising the amino acid sequence of WGPGTLVTVSS (SEQ ID NO: 8).

3. The isolated nucleic acid of claim 1, wherein the VH comprises an amino acid sequence having at least 95% sequence identity to the amino acid sequence of SEQ ID NO: 16.

4. The isolated nucleic acid of claim 1, wherein the VH comprises SEQ ID NO: 16.

5. A vector comprising the isolated nucleic acid of claim 1.

6. A host cell comprising the vector of claim 5.

7. An isolated nucleic acid encoding an antibody light chain variable domain (VL), wherein the VL comprises the following hypervariable regions (HVR-Ls):
- (a) an HVR-L1 comprising the amino acid sequence of QASESVYSNNYLS (SEQ ID NO: 9);
- (b) an HVR-L2 comprising the amino acid sequence of LASTLAS (SEQ ID NO: 10); and
- (c) an HVR-L3 comprising the amino acid sequence of IGGKSSSTDGNA (SEQ ID NO: 11).

8. The isolated nucleic acid of claim 7, wherein the VL further comprises light chain variable domain framework regions (FR-Ls):

(d) FR-L1 comprising the amino acid sequence of AIVMTQTPSPVSAAVGGTVTINC (SEQ ID NO: 12);

(e) FR-L2 comprising the amino acid sequence of WFQQKPGQPPKLLIY (SEQ ID NO: 13);

(f) FR-L3 comprising the amino acid sequence of GVPSRFKGSGSGTQFTLTISGVQCDDAATYYC (SEQ ID NO: 14); and (g) FR-L4 comprising the amino acid sequence of FGGGTEVVVR (SEQ ID NO: 15).

9. The isolated nucleic acid of claim 7, wherein the VL comprises an amino acid sequence having at least 95% sequence identity to SEQ ID NO: 17.

10. The isolated nucleic acid of claim 7, wherein the VL comprises SEQ ID NO: 17.

11. A vector comprising the isolated nucleic acid of claim 7.

12. A host cell comprising the vector of claim 11.

13. An isolated nucleic acid encoding an antibody heavy chain variable domain (VH) and an antibody light chain variable domain (VL), wherein:

the VH comprises the following heavy chain hypervariable regions (HVR-Hs):

(a) an HVR-H1 comprising the amino acid sequence of SNGLT (SEQ ID NO: 2);

(b) an HVR-H2 comprising the amino acid sequence of TINKDASAYYASWAKG (SEQ ID NO: 3); and (c) an HVR-H3 comprising the amino acid sequence of IAFKTGTSI (SEQ ID NO: 4); and the VL comprises the following light chain hypervariable regions (HVR-Ls):

(d) an HVR-L1 comprising the amino acid sequence of QASESVYSNNYLS (SEQ ID NO: 9);

(e) an HVR-L2 comprising the amino acid sequence of LASTLAS (SEQ ID NO: 10); and (f) an HVR-L3 comprising the amino acid sequence of IGGKSSSTDGNA (SEQ ID NO: 11).

14. The isolated nucleic acid of claim 13, wherein the VH further comprises the following heavy chain variable domain framework regions (FR-Hs):

(g) FR-H1 comprising the amino acid sequence of QSLEESGGRLVKPDETLTITCTVSGIDLS (SEQ ID NO: 5);

(h) FR-H2 comprising the amino acid sequence of WVRQAPGEGLEWIG (SEQ ID NO: 6);

(i) FR-H3 comprising the amino acid sequence of RLTISKPSSTKVDLKITSPTTEDTATYFCGR (SEQ ID NO: 7); and (j) FR-H4 comprising the amino acid sequence of WGPGTLVTVSS (SEQ ID NO: 8).

15. The isolated nucleic acid of claim 13, wherein the VH comprises an amino acid sequence having at least 95% sequence identity to the amino acid sequence of SEQ ID NO: 16.

16. The isolated nucleic acid of claim 13, wherein the VH comprises SEQ ID NO: 16.

17. The isolated nucleic acid of claim 13, wherein the VL further comprises the following light chain variable domain framework regions (FR-Ls):

(k) FR-L1 comprising the amino acid sequence of AIVMTQTPSPVSAAVGGTVTINC (SEQ ID NO: 12);

(l) FR-L2 comprising the amino acid sequence of WFQQKPGQPPKLLIY (SEQ ID NO: 13);

(m) FR-L3 comprising the amino acid sequence of GVPSRFKGSGSGTQFTLTISGVQCDDAATYYC (SEQ ID NO: 14); and (n) FR-L4 comprising the amino acid sequence of FGGGTEVVVR (SEQ ID NO: 15).

18. The isolated nucleic acid of claim 13, wherein the VL comprises an amino acid sequence having at least 95% sequence identity to SEQ ID NO: 17.

19. The isolated nucleic acid of claim 13, wherein the VL comprises SEQ ID NO: 17.

20. A vector comprising the isolated nucleic acid of claim 13.

21. A host cell comprising the vector of claim 20.

\*   \*   \*   \*   \*

SEQUENCE LISTING

```
Sequence total quantity: 18
SEQ ID NO: 1              moltype = AA  length = 12
FEATURE                   Location/Qualifiers
source                    1..12
                          mol_type = protein
                          organism = synthetic construct
SEQUENCE: 1
SKKQSDTHLE ET                                             12

SEQ ID NO: 2              moltype = AA  length = 5
FEATURE                   Location/Qualifiers
source                    1..5
                          mol_type = protein
                          organism = synthetic construct
SEQUENCE: 2
SNGLT                                                     5

SEQ ID NO: 3              moltype = AA  length = 16
FEATURE                   Location/Qualifiers
```

-continued

```
source                    1..16
                          mol_type = protein
                          organism = synthetic construct
SEQUENCE: 3
TINKDASAYY ASWAKG                                              16

SEQ ID NO: 4              moltype = AA   length = 9
FEATURE                   Location/Qualifiers
source                    1..9
                          mol_type = protein
                          organism = synthetic construct
SEQUENCE: 4
IAFKTGTSI                                                       9

SEQ ID NO: 5              moltype = AA   length = 29
FEATURE                   Location/Qualifiers
source                    1..29
                          mol_type = protein
                          organism = synthetic construct
SEQUENCE: 5
QSLEESGGRL VKPDETLTIT CTVSGIDLS                                29

SEQ ID NO: 6              moltype = AA   length = 14
FEATURE                   Location/Qualifiers
source                    1..14
                          mol_type = protein
                          organism = synthetic construct
SEQUENCE: 6
WVRQAPGEGL EWIG                                                14

SEQ ID NO: 7              moltype = AA   length = 31
FEATURE                   Location/Qualifiers
source                    1..31
                          mol_type = protein
                          organism = synthetic construct
SEQUENCE: 7
RLTISKPSST KVDLKITSPT TEDTATYFCG R                             31

SEQ ID NO: 8              moltype = AA   length = 11
FEATURE                   Location/Qualifiers
source                    1..11
                          mol_type = protein
                          organism = synthetic construct
SEQUENCE: 8
WGPGTLVTVS S                                                   11

SEQ ID NO: 9              moltype = AA   length = 13
FEATURE                   Location/Qualifiers
source                    1..13
                          mol_type = protein
                          organism = synthetic construct
SEQUENCE: 9
QASESVYSNN YLS                                                 13

SEQ ID NO: 10             moltype = AA   length = 7
FEATURE                   Location/Qualifiers
source                    1..7
                          mol_type = protein
                          organism = synthetic construct
SEQUENCE: 10
LASTLAS                                                         7

SEQ ID NO: 11             moltype = AA   length = 12
FEATURE                   Location/Qualifiers
source                    1..12
                          mol_type = protein
                          organism = synthetic construct
SEQUENCE: 11
IGGKSSSTDG NA                                                  12

SEQ ID NO: 12             moltype = AA   length = 23
FEATURE                   Location/Qualifiers
source                    1..23
                          mol_type = protein
                          organism = synthetic construct
SEQUENCE: 12
AIVMTQTPSP VSAAVGGTVT INC                                      23

SEQ ID NO: 13             moltype = AA   length = 15
```

-continued

```
FEATURE            Location/Qualifiers
source             1..15
                   mol_type = protein
                   organism = synthetic construct
SEQUENCE: 13
WFQQKPGQPP KLLIY                                              15

SEQ ID NO: 14      moltype = AA  length = 32
FEATURE            Location/Qualifiers
source             1..32
                   mol_type = protein
                   organism = synthetic construct
SEQUENCE: 14
GVPSRFKGSG SGTQFTLTIS GVQCDDAATY YC                           32

SEQ ID NO: 15      moltype = AA  length = 10
FEATURE            Location/Qualifiers
source             1..10
                   mol_type = protein
                   organism = synthetic construct
SEQUENCE: 15
FGGGTEVVVR                                                    10

SEQ ID NO: 16      moltype = AA  length = 115
FEATURE            Location/Qualifiers
source             1..115
                   mol_type = protein
                   organism = synthetic construct
SEQUENCE: 16
QSLEESGGRL VKPDETLTIT CTVSGIDLSS NGLTWVRQAP GEGLEWIGTI NKDASAYYAS  60
WAKGRLTISK PSSTKVDLKI TSPTTEDTAT YFCGRIAFKT GTSIWGPGTL VTVSS       115

SEQ ID NO: 17      moltype = AA  length = 112
FEATURE            Location/Qualifiers
source             1..112
                   mol_type = protein
                   organism = synthetic construct
SEQUENCE: 17
AIVMTQTPSP VSAAVGGTVT INCQASESVY SNNYLSWFQQ KPGQPPKLLI YLASTLASGV  60
PSRFKGSGSG TQFTLTISGV QCDDAATYYC IGGKSSSTDG NAFGGGTEVV VR          112

SEQ ID NO: 18      moltype = AA  length = 290
FEATURE            Location/Qualifiers
source             1..290
                   mol_type = protein
                   organism = Homo sapiens
SEQUENCE: 18
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET            290
```